(12) United States Patent
Lee et al.

(10) Patent No.: US 7,074,805 B2
(45) Date of Patent: Jul. 11, 2006

(54) FUSED AZABICYCLIC COMPOUNDS THAT INHIBIT VANILLOID RECEPTOR SUBTYPE 1 (VR1) RECEPTOR

(75) Inventors: Chih-Hung Lee, Vernon Hills, IL (US); Erol K. Bayburt, Gurene, IL (US); Stanley DiDomenico, Jr., Richmond, IL (US); Irene Drizin, Wadsworth, IL (US); Arthur R. Gomtsyan, Vernon Hills, IL (US); John R. Koenig, Chicago, IL (US); Richard J. Perner, Gurnee, IL (US); Robert G. Schmidt, Jr., Waukegan, IL (US); Sean C. Turner, Evanston, IL (US); Tammie K. White, Gurnee, IL (US); Guo Zhu Zheng, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 167 days.

(21) Appl. No.: 10/364,210

(22) Filed: Feb. 11, 2003

(65) Prior Publication Data

US 2003/0158198 A1 Aug. 21, 2003

(51) Int. Cl.
*A61K 31/47* (2006.01)
*C07D 217/00* (2006.01)

(52) U.S. Cl. .................................. 514/307; 546/143
(58) Field of Classification Search ................. 514/307; 546/143
See application file for complete search history.

(56) References Cited

U.S. PATENT DOCUMENTS

| | | | |
|---|---|---|---|
| 3,647,819 A | | 3/1972 | Kirchner |
| 3,711,610 A | | 1/1973 | Kirchner |
| 3,814,711 A | * | 6/1974 | Eloy et al. .................. 424/258 |
| 4,958,026 A | | 9/1990 | Schoellkopf et al. |
| 5,362,878 A | * | 11/1994 | Chang et al. ............... 546/296 |
| 5,444,038 A | | 8/1995 | James et al. |
| 5,656,634 A | * | 8/1997 | Chang et al. ............... 514/255 |
| 5,760,246 A | | 6/1998 | Biller et al. |
| 6,291,476 B1 | * | 9/2001 | Kordik et al. .............. 514/310 |
| 6,472,414 B1 | | 10/2002 | Biller et al. |
| 6,511,998 B1 | * | 1/2003 | Kordik et al. .............. 514/341 |
| 6,555,539 B1 | * | 4/2003 | Reich et al. ................ 514/252 |

FOREIGN PATENT DOCUMENTS

| | | | |
|---|---|---|---|
| EP | 0418071 A2 | * | 3/1991 |
| EP | 0609960 A1 | * | 8/1994 |
| EP | 1 403 255 | | 3/2004 |
| FR | 1 344 579 | | 10/1963 |
| GB | 2020280 A | * | 11/1979 |
| WO | WO91/13874 A1 | * | 9/1991 |
| WO | 97/26240 | | 7/1997 |
| WO | 00/50387 | | 8/2000 |
| WO | 02/08221 | | 1/2002 |
| WO | WO03/14064 A1 | * | 2/2003 |
| WO | 03/014064 | | 2/2003 |
| WO | WO03/22809 A2 | * | 3/2003 |
| WO | 03/22809 | | 3/2003 |
| WO | WO03/80578 A1 | * | 10/2003 |

OTHER PUBLICATIONS

Berge, et al., "Pharmaceutical Salts," *Journal of Pharmaceutical Sciences* 66:1–19 (1977) (Jan., 1977).
Caterina, et al., "Impaired Nociception and pain sensation in mice lacking the capsaicin receptor," *Science* 288:306–313 (2000) (Apr. 14, 2000).
Caterina, et al., "The capsaicin receptor: a heat–activated ion channel in the pain pathway," *Nature* 389:816–824 (1997) (Oct. 23, 1997).
Caterina, et al., "The Vanilloid Receptor: A Molecular gateway to the pain pathway," *Annual Review of Neuroscience* 24:487–517 (2001).
Collier, et al., Br. J. Pharmacol. Chemother. 32:295–310 (1968).
Davis, et al., "Vanilloid receptor–1 is essential for inflammatory thermal hyperalgesia," *Nature* 405:183–187 (2000) (May 11, 2000).
Fowler, "Intravesical treatment of overactive bladder," *Urology* 55(Supp 5A):60–64 (2000) (May, 2000).
Hayes, et al., "Cloning and functional expression of a human orthologue of rat vanilloid receptor–1," *Pain* 88:205–215 (2000).
Nolano, et al., "Topical capsaicin in humans: parallel loss of epidermal nerve fibers and pain sensation," *Pain* 81:135–145 (1999).

(Continued)

*Primary Examiner*—L. E. Crane
(74) *Attorney, Agent, or Firm*—Gabryleda Ferari-Dileo

(57) ABSTRACT

The isoquinoline compounds of formula (I)

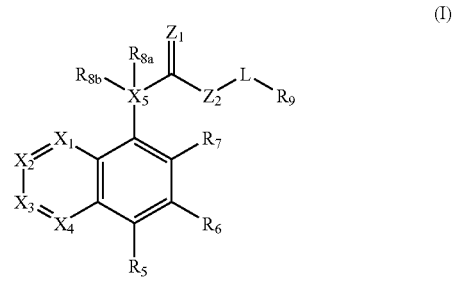

are VR1 antagonists that are useful in treating pain, inflammation, thermal hyperalgesia, urinary incontinence and bladder over activity. The "R", "Z" and "L" variables are defined in the disclosure and the "X" variables are defined as follows:

$X_1$ is $CR_1$;
$X_2$ is selected from the group consisting of N and $CR_2$;
$X_3$ is selected from the group consisting of N and $CR_3$;
$X_4$ is $CR_4$; and
$X_5$ is selected from the group consisting of N and C.

69 Claims, No Drawings

OTHER PUBLICATIONS

Poste, et al., *Methods in Cell Biology*, Academic Press, New York, N.Y. vol. 14:33–71 (1976).

Adams et al., "Dialkylaminoalkyquinolines," J. Chem. Soc. 3066–3071 (1957).

Cannon et al., "Synthesis of N–alkyl derivatives of 4–(2'–aminothyl)indole," J. Heterocyclic Chemistry 19:1195–1199 (1982) (Sep.–Oct., 1982).

Craig et al., "Derivatives of aminoisoquinolines," J. Am. Chem. Soc. 64:783–784 (1942) (Nov., 1942).

Fieser et al., "A comparison of heterocyclic systems with benzene. VI. Quinines of the quinoline and isoquinoline series," J. Amer. Chem. Soc. 57:1840–1844 (1935) (Oct., 1935).

Forbes et al., "N–(1–methyl–5–indolyl)–N'–(3–pyridyl)urea hydrochloride: the first selective 5–$HT_{1C}$ receptor antagonist," J. Med. Chem. 36:1104–1107 (1993).

Gall et al., "171. On a few derivatives of heterocyclic carbonic acids IV. Metal ions and biological action, $36^{th}$ report," Helv. Chim. Acta 38(171):1421–1423 (1955) with translation.

Honma et al., "Structure–based generation of a new class of potent Cdk4 inhibitors: New *de Novo* design strategy and library design," J. Med. Chem. 44:4615–4627 (2001).

Kawasaki et al., "A new approach to 4–(2–aminoethyl)indoles via Claisen *ortho*–amide rearrangement of 3–hydroxy–2–methoxyindolines," J. Chem. Soc. Chem. Commun. 10:781–782 (1990).

Kumar et al. "Antiparasitic agents: Part XV—Synthesis of 2–substituted 1(3)H–imidazo[4,5–f]isoquinolines as anthelmintic agents," Indian Journal of Chemistry 31B:177–182 (1992) (Mar., 1992).

Mooney et al., "Potential antitumor agens, 10. Synthesis and biochemical properties of 5–N–alkylamino–,N,N–dialkylamino–, and N–alkylacetamido–1–formylisoquinoline thiosemicarbazones," Journal of Medicinal Chemistry 17(11):1145–1150 (1974).

Naruto et al., "Photo–induced Friedel–Crafts reactions. IV>Indoleacetic acids," Chemical and Pharmaceutical Bulletin, Tokyo, JP 20(10):2163–2171 (1972).

Prijs et al. "9. On a few derivatives of heterocyclic carbonic acids I . . . Metal ions and biological action, $16^{th}$ report," Helv. Chim. Acta 37:90–94 (1954) with translation.

Sato et al., "Construction of optically pure tryptophans from serine derived aziridine–2–carboxylates," Tetrahedron Letters 30(31):4073–4076 (1989).

Taurins et al., "Thiazoloisoquinolines. IV. The synthesis and spectra of thiazolo[4,5–h]–and thiazolo[5,4–f]isoquinolines. The ultraviolet and proton magnetic resonance spectra of some substituted isoquinolines," Canadian Journal of Chemistry 49(24):4054–4061 (1971).

Warpehoski et al., "Stereoelectronic factors influencing the biological activity and DNA intereaction of synthetic antitumor agents modeled on CC–1065," J. Med. Chem. 31:590–603 (1988) (Issue No. 3).

Lichtenthaler et al., "Nucleosides. 44. Benzo–separated Pyrazolopyrimidines: Expeditions Synthesis of [3,4–g] and [3,4–h]–linked Pyrazoloquinazolinones" Tetrahedron Letters 22(44):4397–4400 (1981).

Nunn et al., "Semmler–Wolf Aromatization and Abnormal Beckmann and Schmidt Reactions of 3–Alkyl–4Oxo–1–phenyl–4,5,6,7,–tetrahydroindazoles and their oximes in polyphosphoric acid" J. Chem. Soc. Perkin Transactions 1, 1973 No. 22:2697–2703 (1973).

R. Gall: Über Einige Derivative Heterocyclischer Carbonsaüren, Helv. Chim. Acta, vol. 37 (1954), pp. 90–94 (English translation summary–last page).

* cited by examiner

FUSED AZABICYCLIC COMPOUNDS THAT INHIBIT VANILLOID RECEPTOR SUBTYPE 1 (VR1) RECEPTOR

TECHNICAL BACKGROUND

The present invention relates to compounds of formula (I), which are useful for treating disorders caused by exacerbated by or vanilloid receptor activity, pharmaceutical compositions containing compounds of formula (I) and are useful in treating pain, bladder overactivity, and urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH <6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6–7), the affinity of capsaicin for the receptor is increased, whereas the pH <6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (-/-) mice also did not show reduced sensitivity to nerve injury-induced mechanical or thermal nociceptin. However, the VR1 knock-out mice were insensitive to the noxious effects of intradermal capsaicin, exposure to intense heat (50–55° C.), and failed to develop thermal hyperalgesia following the intradermal administration of carrageenan.

The compounds of the present invention are novel VR1 antagonists and have utility in treating pain, bladder overactivity, and urinary incontinence.

SUMMARY OF THE PRESENT INVENTION

The present invention discloses fused azabicyclic compounds, a method for inhibiting the VR1 receptor in mammals using these compounds, a method for controlling pain in mammals, and pharmaceutical compositions including those compounds. More particularly, the present invention is directed to compounds of formula (I)

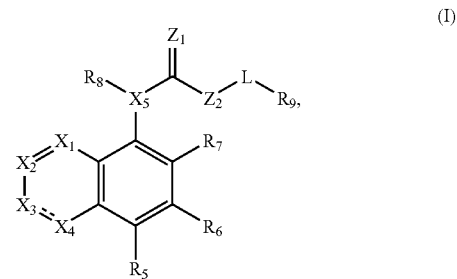

or a pharmaceutically acceptable salt or prodrug thereof, wherein

— is absent or a single bond;

$X_1$ is selected from the group consisting of N and $CR_1$;

$X_2$ is selected from the group consisting of N and $CR_2$;

$X_3$ is selected from the group consisting of N, $NR_3$, and $CR_3$;

$X_4$ is a bond or selected from the group consisting of N and $CR_4$;

$X_5$ is selected from the group consisting of N and C;

provided that at least one of $X_1$, $X_2$, $X_3$, and $X_4$ is N; and provided that when $X_4$ is a bond, one of $X_1$, $X_2$, or $X_3$ must be N—H;

$Z_1$ is selected from the group consisting of OH, NH, and S;

$Z_2$ is a bond or selected from the group consisting of NH and O;

L is selected from the group consisting of alkenylene, alkylene, alkynylene,

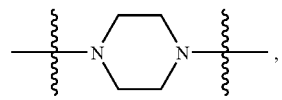

—$(CH_2)_mO(CH_2)_n$—, —N(H)O—, and —NHNH— wherein the left end of —$(CH_2)_mO(CH_2)_n$— and —N(H)O— is attached to $Z_2$ and the right end is attached to $R_9$;

provided that when $Z_2$ is NH or O then L is other than —N(H)O— or —NHNH—;

m and n are each independently 1–6;

$R_1$, $R_3$, $R_5$, $R_6$ and $R_7$ are each independently selected from hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C-$, $-NR_AS(O)_2R_B$, $-S(O)_2OR_A$, $-S(O)_2R_B$, $-NZ_{AZB}$, $(NZ_AZ_B)$alkyl, $(NZ_AZ_B)$carbonyl, $(NZ_AZ_B)$carbonylalkyl and $(NZ_AZ_B)$sulfonyl, wherein $Z_A$ and $Z_B$ are each independently selected from hydrogen, alkyl, alkylcarbonyl, formyl, aryl and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$alkylcarbonyl, $(NZ_AZ_B)$carbonyl, $(NZ_AZ_B)$carbonylalkyl, $(NZ_AZ_B)$sulfonyl, $(NZ_AZ_B)C(=NH)-$, $(NZ_AZ_B)C(=NCN)NH-$, and $(NZ_AZ_B)C(=NH)NH-$;

$R_A$ is selected from hydrogen and alkyl;

$R_B$ is selected from alkyl, aryl and arylalkyl;

$R_8$ is absent or selected from hydrogen and alkyl;

provided that $R_8$ is absent when $X_5$ is $CH_2$ and $R_8$ is selected from hydrogen and alkyl when $X_5$ is N; and $R_9$ is selected from hydrogen, aryl and heterocycle.

DETAILED DESCRIPTION OF THE PRESENT INVENTION

In the principle embodiment, compounds of formula (I) are disclosed

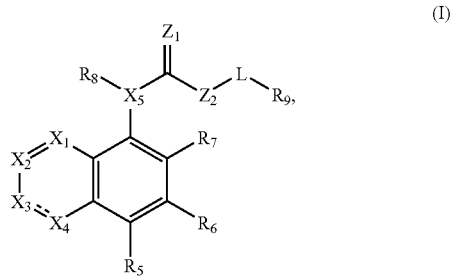

(I)

or a pharmaceutically acceptable salt or prodrug thereof, wherein

— is absent or a covalent bond;

$X_1$ is selected from the group consisting of N and $CR_1$;

$X_2$ is selected from the group consisting of N and $CR_2$;

$X_3$ is selected from the group consisting of N, $NR_3$, and $CR_3$;

$X_4$ is a bond or selected from the group consisting of N and $CR_4$;

$X_5$ is selected from the group consisting of N and C;

provided that at least one of $X_1$, $X_2$, $X_3$, and $X_4$ is N; and provided that when $X_4$ is a bond, one of $X_1$, $X_2$, or $X_3$ must be N—H;

$Z_1$ is selected from the group consisting of O, NH, and S;

$Z_2$ is a bond or selected from the group consisting of NH and O;

L is selected from the group consisting of alkenylene, alkylene, alkynylene,

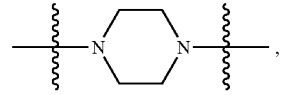

$-(CH_2)_mO(CH_2)_n-$, $-N(H)O-$, and $-NHNH-$ wherein the left end of $-(CH_2)_mO(CH_2)_n-$ and $-N(H)O-$ is attached to $Z_2$ and the right end is attached to $R_9$;

provided that when $Z_2$ is NH or O then L is other than $-N(H)O-$ or $-NHNH-$;

m and n are each independently 1–6;

$R_1$, $R_3$, $R_5$, $R_6$ and $R_7$ are each independently selected from hydrogen, alkenyl, alkoxy, alkoxyalkoxy, alkoxyalkyl, alkoxycarbonyl, alkoxycarbonylalkyl, alkyl, alkylcarbonly, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C-$, $-NR_AS(O)_2R_B$, $-S(O)_2OR_A$, $-S(O)_2R_B$, $-NZ_{AZB}$, $(NZ_AZ_B)$alkyl, $(NZ_AZ_B)$carbonyl, $(NZ_AZ_B)$carbonylalkyl and $(NZ_AZ_B)$sulfonyl, wherein $Z_A$ and $Z_B$ are each independently selected from hydrogen, alkyl, alkylcarbonyl, formyl, aryl and arylalkyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$alkylcarbonyl, $(NZ_AZ_B)$carbonyl, $(NZ_AZ_B)$carbonylalkyl, $(NZ_AZ_B)$sulfonyl, $(NZ_AZ_B)C(=NH)-$, $(NZ_AZ_B)C(=NCN)NH-$, and $(NZ_AZ_B)C(=NH)NH-$;

$R_A$ is selected from hydrogen and alkyl;

$R_B$ is selected from alkyl, aryl and arylalkyl;

$R_8$ is absent or selected from hydrogen and alkyl;

provided that $R_8$ is absent when $X_5$ is $CH_2$ and $R_8$ is selected from hydrogen and alkyl when $X_5$ is N; and $R_9$ is selected from hydrogen, aryl and heterocycle.

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $R_1$, $R_2$, $R_4$, $R_5$, $R_6$, $R_7$, $R_8$, $R_9$, $X_5$, $Z_1$, $Z_2$, and L are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is N; L is alkylene; $R_9$ is aryl; and $R_1$, $R_2$, $R_4$, $R_5$, $R_6$, $R_7$, and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is substituted with aryloxy; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is phenyl substituted with aryloxy wherein said aryloxy is phenoxy substituted with 1, 2, or 3 substituents selected from the group consisting of hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is substituted with heterocycle; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is phenyl substituted with heterocycle wherein said heterocycle is selected from 2,6-dimethylmorpholinyl, morpholinyl, and thiomorpholinyl; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is aryl wherein said aryl is napthyl; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is N; $R_9$ is hydrogen; and $R_1$, $R_2$, $R_4$, $R_5$, $R_6$, $R_7$, $R_8$, and L are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is alkylene; $R_9$ is hydrogen; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is N; L is cycloalkylene; $R_9$ is aryl; and $R_1$, $R_2$, $R_4$, $R_5$, $R_6$, $R_7$, and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$, and $R_7$ are each hydrogen; $Z_1$ is O; $Z_2$ is N; L is cycloalkylene; $R_9$ is aryl wherein said aryl is phenyl substituted 1, 2, or 3 substituents selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is N; L is —$(CH_2)_mO(CH_2)_n$—; $R_9$ is aryl; and $R_1$, $R_2$, $R_4$, $R_5$, $R_6$, $R_7$, $R_8$, m and n are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $Z_1$ is O; $Z_2$ is N; L is —$(CH_2)_mO(CH_2)_n$— wherein the left end is attached to $Z_2$ and the right end is attached to $R_9$; m is 2–4; n is 0; $R_9$ is aryl wherein said aryl is phenyl substituted 1, 2, or 3 substituents selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is N; L is

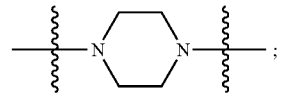

$R_9$ aryl; and $R_1$, $R_2$, $R_4$, $R_5$, $R_6$, $R_7$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $Z_1$ is O; $Z_2$ is N; L is

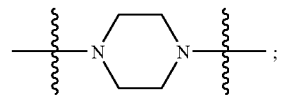

$R_9$ is aryl wherein said aryl is phenyl substituted 1, 2, or 3 substituents selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_4$, $R_5$, $R_6$ and $R_7$ are each hydrogen; $R_2$ is selected from alkoxycarbonyl, alkyl and halogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_5$, $R_6$ and $R_7$ are each hydrogen; $R_4$ is selected from alkyl and halogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$ and $R_6$ are each hydrogen; $R_5$ is hydrogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$ and $R_6$ are each hydrogen; $R_7$ is $(CF_3)_2(HO)C—$; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_5$, and $R_7$ are each hydrogen; $R_4$ is selected from $(NZ_AZ_B)$alkylcarbonyl, $(NZ_AZ_B)$carbonyl, $(NZ_AZ_B)C(=NH)—$, $(NZ_AZ_B)C(=NCN)NH—$, and $(NZ_AZ_B)C(=NH)NH—$; $Z_1$ is O; $Z_2$ is N; L is alkylene; and $Z_A$, $Z_B$, $R_8$, and $R_9$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_5$, $R_6$, and $R_7$ are each hydrogen; $R_4$ is selected from $(NZ_AZ_B)$alkylcarbonyl, $(NZ_AZ_B)$carbonyl, $(NZ_AZ_B)C(=NH)—$, $(NZ_AZ_B)C(=NCN)NH—$, and $(NZ_AZ_B)C(=NH)NH—$; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_4$, $R_5$, $R_6$ and $R_7$ are each hydrogen; $R_2$ is selected from $(NZ_AZ_B)$alkylcarbonyl, $(NZ_AZ_B)$carbonyl, $(NZ_AZ_B)C(=NH)—$, $(NZ_AZ_B)C(=NCN)NH—$, and $(NZ_AZ_B)C(=NH)NH—$; $Z_1$ is O; $Z_2$ is N; L is alkylene; and $Z_A$, $Z_B$, $R_8$, and $R_9$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_4$, $R_5$, $R_6$, and $R_7$ are each hydrogen; $R_2$ is selected from $(NZ_AZ_B)$alkylcarbonyl, $(NZ_AZ_B)$carbonyl, $(NZ_AZ_B)C(=NH)—$, $(NZ_AZ_B)C(=NCN)NH—$, and $(NZ_AZ_B)C(=NH)NH—$; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $Z_1$ is O; $Z_2$ is O; L is alkylene; $R_9$ is aryl; and $R_1$, $R_2$, $R_4$, $R_5$, $R_6$, $R_7$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $Z_1$ is O; $Z_2$ is O; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is N; $R_1$, $R_2$, $R_4$, $R_5$, $R_6$ and $R_7$ are each hydrogen; $Z_1$ is O; $Z_2$ is O; L is alkylene; $R_9$ is aryl wherein said aryl is naphthyl; and $R_8$ is as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is $CH_2$; $Z_1$ is O; $Z_2$ is N; L is alkylene; $R_9$ is aryl; $R_8$ is absent; and $R_1$, $R_2$, $R_4$, $R_5$, $R_6$, and $R_7$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is $CR_4$; $X_5$ is $CH_2$; $R_1$, $R_2$, $R_4$, $R_5$, $R_6$ and $R_7$ are each hydrogen; $Z_1$ is O; $Z_2$ is N; L is alkylene; $R_9$ is aryl wherein said aryl is phenyl substituted with 1, 2, or 3 substituents independently selected hydrogen, alkoxy, alkyl, alkylsulfonyl, cyano, haloalkoxy, haloalkyl, haloalkylthio, halogen, methylenedioxy, and —$NZ_AZ_B$; $R_8$ is absent; and $Z_A$ and $Z_B$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is N; and $R_1$, $R_2$, $R_5$, $R_6$, $R_7$, $R_8$, $R_9$, $X_5$, $Z_1$, $Z_2$ and L are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is N; $X_5$ is N; $Z_1$ is O; $Z_2$ is N; L is alkylene; $R_9$ is aryl; and $R_1$, $R_2$, $R_5$, $R_6$, $R_7$ and $R_8$ are as defined in formula (I).

In another embodiment of the present invention, compounds of formula (I) are disclosed wherein — is a covalent bond; $X_1$ is $CR_1$; $X_2$ is $CR_2$; $X_3$ is N; $X_4$ is N; $X_5$ is N; $R_1$, $R_5$, $R_6$ and $R_7$ are each hydrogen; $R_2$ is selected from alkyl and halogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is a covalent bond; $X_1$ is $CR_1$; $X_2$ is N; $X_3$ is $CR_3$; $X_4$ is $CR_4$; and $R_1$, $R_3$, $R_4$, $R_5$, $R_6$, $R_7$, $R_8$, $R_9$, $X_5$, $Z_1$, $Z_2$ and L are as defined in formula (I).

In another embodiment of the present invention, compounds of formula (I) are disclosed wherein — is a covalent bond; $X_1$ is $CR_1$; $X_2$ is N; $X_3$ is $CR_3$; $X_4$ is $CR_4$; $X_5$ is N; $Z_1$ is O; $Z_2$ is N; L is alkylene; $R_9$ is aryl; and $R_1$, $R_3$, $R_4$, $R_5$, $R_6$, $R_7$ and $R_8$ are as defined in formula (I).

In another embodiment of the present invention, compounds of formula (I) are disclosed wherein — is a covalent bond; $X_1$ is $CR_1$; $X_2$ is N; $X_3$ is $CR_3$; $X_4$ is $CR_4$; $X_5$ is N; $R_1$, $R_3$, $R_4$, $R_5$, $R_6$ and $R_7$ are each hydrogen; $Z_1$ is O; $Z_2$ is N; L is alkylene; $R_9$ is aryl wherein said aryl is phenyl substituted with 1, 2, or 3, substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; and $R_1$, $R_2$, $R_5$, $R_6$, $R_7$, $R_8$, $R_9$, $X_5$, $Z_1$, $Z_2$ and L are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $Z_1$ is O; $Z_2$ is N; L is alkylene; $R_9$ is aryl; and $R_1$, $R_2$, $R_5$, $R_6$, $R_7$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $R_1$, $R_2$, $R_5$, $R_6$ and $R_7$ are each hydrogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $R_5$, $R_6$ and $R_7$ are each hydrogen; $R_1$ and $R_2$ are each independently alkyl; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $R_5$, $R_6$ and $R_7$ are each hydrogen; $R_1$ and $R_2$ are each independently alkyl wherein said alkyl is methyl; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $Z_1$ is O; $Z_2$ is O; L is alkylene; $R_9$ is aryl; and $R_1$, $R_2$, $R_5$, $R_6$, $R_7$ and $R_8$ are as defined in formula (I).

In another embodiment of the present invention, compounds of formula (I) are disclosed wherein — is absent; $X_1$ is $CR_1$; $X_2$ is $CR_2$; $X_3$ is N; $X_4$ is absent; $X_5$ is N; $R_1$, $R_2$, $R_5$, $R_6$ and $R_7$ are each hydrogen; $Z_1$ is O; $Z_2$ is O; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

In another embodiment of the present invention, compounds of formula (I) are disclosed wherein — is absent; $X_1$ is $CR_1$; $X_2$ is N; $X_3$ is N; $X_4$ is absent; and $R_1$, $R_5$, $R_6$, $R_7$, $R_8$, $R_9$, $X_5$, $Z_1$, $Z_2$ and L are as defined in formula (I).

In another embodiment of the present invention, compounds of formula (I) are disclosed wherein — is absent; $X_1$ is $CR_1$; $X_2$ is N; $X_3$ is N; $X_4$ is absent; $X_5$ is N; $Z_1$ is O; $Z_2$ is N; L is alkylene; $R_9$ is aryl; and $R_1$, $R_5$, $R_6$, $R_7$, and $R_8$ are as defined in formula (I).

In another embodiment of the present invention, compounds of formula (I) are disclosed wherein — is absent; $X_1$ is $CR_1$; $X_2$ is N; $X_3$ is N; $X_4$ is absent; $X_5$ is N; $R_1$, $R_5$, $R_6$ and $R_7$ are each hydrogen; $Z_1$ is O; $Z_2$ is N; L is alkylene; $R_9$ is aryl wherein said aryl is phenyl substituted with 1, 2, or 3 substituents independently selected from hydrogen, alkoxy, alkyl, alkylsulfonyl, cyano, haloalkoxy, haloalkyl, haloalkylthio, halogen, methylenedioxy, and —$NZ_AZ_B$; and $Z_A$, $Z_B$ and $R_8$ are as defined in formula (I).

Another embodiment of the present invention relates to pharmaceutical compositions comprising a therapeutically effective amount of a compound of formula (I) or a pharmaceutically acceptable salt thereof.

Another embodiment of the present invention relates to a method of treating a disorder wherein the disorder is ameliorated by inhibiting vanilloid receptor subtype 1 (VR1) receptor in a host mammal in need of such treatment comprising administering a therapeutically effective amount of a compound of formula (I) or a pharmaceutically acceptable salt thereof.

Another embodiment of the present invention relates to a method for controlling pain in a host mammal in need of such treatment comprising administering a therapeutically effective amount of a compound of formula (I) or a pharmaceutically acceptable salt thereof.

Another embodiment of the present invention relates to a method of treating urinary incontinence in a host mammal in need of such treatment comprising administering a therapeutically effective amount of a compound of formula (I) or a pharmaceutically acceptable salt thereof.

Another embodiment of the present invention relates to a method of treating bladder overactivity in a host mammal in need of such treatment comprising administering a therapeutically effective amount of a compound of formula (I) or a pharmaceutically acceptable salt thereof.

Another embodiment of the present invention relates to a method of treating inflammatory thermal hyperalgesia in a host mammal in need of such treatment comprising administering a therapeutically effective amount of a compound of formula (I) or a pharmaceutically acceptable salt thereof.

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of the alkyl include, but are not limited to, methyl, ethyl, n-propyl, iso-propyl, n-butyl, sec-butyl, ios-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "akylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —$CH_2$CH≡C, —CH($CH_3$)$CH_2$C≡C, —C≡CCH$_2$—, and —C≡CCH($CH_3$)$CH_2$—.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_AZ_B$, ($NZ_AZ_B$)alkyl, ($NZ_AZ_B$) carbonyl, ($NZ_AZ_B$)carbonylalkyl, ($NZ_AZ_B$)sulfonyl, —$NR_AS(O)_2R_B$, —$S(O)_2OR_A$ and —$S(O)_2R_A$ wherein $R_A$ and $R_B$ are as defined herein. The aryl groups of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_AZ_B$, ($NZ_AZ_B$)alkyl, ($NZ_AZ_B$) carbonyl, ($NZ_AZ_B$)carbonylalkyl, ($NZ_AZ_B$)sulfonyl, —$NR_AS(O)_2R_B$, —$S(O)_2OR_A$ and —$S(O)_2R_A$ wherein $R_A$ and $R_B$ are as defined herein.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylsulfanyl, napth-2-ylsulfanyl, and 5-phenylhexylsulfanyl.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylene" as used herein, means a divalent group derived from a cycloalkyl group, as defined herein. Representative examples of cycloalkylene include, but are not limited to

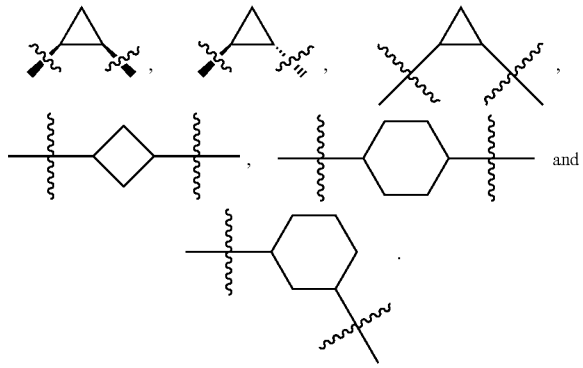

and

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furna, naphtho[2,3-b]thienyl, phenazinyl, phenothiazinyl, phenoxazinyl, thianthrenyl, thioxanthenyl and xanthenyl.

The heterocycles of this invention can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, arylalkyl, aryloxy, arylthio, carboxy, carboxyalkyl, cyano, cyanoalkyl, cycloalkyl, cycloalkylalkyl, formyl, formylalkyl, haloalkoxy, haloalkoxy, haloalkyl, haloalkylthio, halogen, heterocyclealkyl, heterocycleoxy, heterocyclethio, hydroxy, hydroxyalkyl, mercapto, mercaptoalkyl, nitro, oxo, —NZ$_A$Z$_B$, (NZ$_A$Z$_B$)alkyl, (NZ$_A$Z$_B$)carbonyl, (NZ$_A$Z$_B$)carbonylalkyl, (NZ$_A$Z$_B$) sulfonyl, —NR$_A$S(O)$_2$R$_B$, —S(O)$_2$OR$_A$ and —S(O)$_2$R$_A$ wherein R$_A$ and R$_B$ are as defined herein. The heterocycles of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —$NZ_AZ_B$, $(NZ_AZ_B)$alkyl, $(NZ_AZ_B)$carbonyl, $(NZ_AZ_B)$carbonylalkyl, $(NZ_AZ_B)$sulfonyl, —$NR_AS(O)_2R_B$, —$S(O)_2OR_A$ and —$S(O)_2R_A$ wherein $R_A$ and $R_B$ are as defined herein.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocyclethio" as used herein, means a heterocycle group, as defined herein, appended to the parent molecular moiety although a sulfur atom. Representative examples of heterocyclethio include, but are not limited to, pyridin-3-ylsulfanyl and quinolin-3-ylsulfanyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "1-azepanyl" as used herein, means a 7-membered ring wherein one of the atoms is nitrogen.

The term "1-azocanyl" as used herein, means a 8-membered ring wherein one of the atoms is nitrogen.

The term "methylenedioxy" as used herein, means a —$OCH_2O$— group wherein the oxygen atoms of the methylenedioxy are attached to the parent molecular moiety through two adjacent carbon atoms.

The term "nitro" as used herein, means a —$NO_2$ group.

The term "—$NZ_AZ_B$" as used herein, means two groups, $Z_A$ and $Z_B$, which are appended to the parent molecular moiety through a nitrogen atom. $Z_A$ and $Z_B$ are each independently selected from hydrogen, alkyl, alkylcarbonyl, formyl, aryl and arylalkyl. Representative examples of —$NZ_AZ_B$ include, but are not limited to, amino, methylamino, acetylamino, benzylamino, phenylamino, and acetylmethylamino.

The term "$(NZ_AZ_B)$alkyl" as used herein, means a $NZ_AZ_B$ group, as defined herein, appended to the parent molecular moiety through an alkyl group, as defined herein. Representative examples of $(NZ_AZ_B)$alkyl include, but are not limited to, aminomethyl, 2-(methylamino)ethyl, 2-(dimethylamino)ethyl and (ethylmethylamino)methyl.

The term "$(NZ_AZ_B)$carbonyl" as used herein, means a $NZ_AZ_B$ group, as defined herein, appended to the parent molecular moiety through a carbonyl group, as defined herein. Representative examples of $(NZ_AZ_B)$carbonyl include, but are not limited to, aminocarbonyl, (methylamino)carbonyl, (dimethylamino)carbonyl and (ethylmethylamino)carbonyl.

The term "$(NZ_AZ_B)$carbonylalkyl" as used herein, means a $(NZ_AZ_B)$carbonyl group, as defined herein, appended to the parent molecular moiety through an alkyl group, as defined herein. Representative examples of $(NZ_AZ_B)$carbonylalkyl include, but are not limited to, (aminocarbonyl)methyl, 2-((methylamino)carbonyl)ethyl and ((dimethylamino)carbonyl)methyl.

The term "$(NZ_AZ_B)$sulfonyl" as used herein, means a $NZ_AZ_B$ group, as defined herein, appended to the parent molecular moiety through a sulfonyl group, as defined herein. Representative examples of $(NZ_AZ_B)$sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —$S(O)_2$— group.

In Vitro Data

Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 ml/l Na pyruvate) (without phenol red), L-glutamine, hygromycin B, and Lipfectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxoethyl]amino]-5-methylphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88:205–215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with grown medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1–2 hours at 23° C. Washing of the cells were performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration) (final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from 1000 nM to 0.1 nM. In a preferred range, compounds tested had $IC_{50s}$ from 500 nM to 0.1 nM. In a more preferred range, compounds tested had $IC_{50s}$ from 50 nM to 0.1 nM.

In Vivo Data
Determination of Antinociceptive Effect

Experiments were performed on 400 adult male 129J mice (Jackson laboratories, Bar Harbor, Me.), weighing 20–25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the copeltin of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295–310. Each animal received an intraperitoneal (i.p.) injection of 0.3 mL of 0.6% acetic acid in normal saline to evoke writing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constriction was recorded from 5 to 20 minutes after acetic acid injection. The $ED_{50s}$ were determined based on the i.p. injection.

The compounds of the present invention tested were found to have antinociceptive effects with $ED_{50s}$ from 1 mg/kg to 500 mg/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, inflammatory thermal hyperalgesia, bladder overactivity, and urinary incontinence.

Compounds of the present invention, including but not limited to those specified in the examples, can be used to treat pain as demonstrated by Nolan, M. et al., Pain 81 (1999) 135; Caterina, M. J. and Julius, D., Annu. Rev. Neurosci. 24, (2001) 487–517; Caterina, M. J. et al., Science 288 (2000) 306–313; Caterina, M. J. et al., Nature 389 (1997) 816–824.

Compounds of the present invention, including but not limited to those specified in the examples, can be used to treat bladder overactivity and/or urinary incontinence as demonstrated by Fowler, C. Urology 55 (2000) 60.

Compounds of the present invention, including but not limited to those specified in the examples, can be used to treat inflammatory thermal hyperalgesia as demonstrated by Davis, J. et al., Nature 405 (2000) 183–187.

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parentally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin, talc; excipients such as, but not limited to, coca butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramsucular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parentally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor and sesame oils), glycerol, tetrahydrofurfuryl alcohol, polyethylene glycols and fatty acid esters of sorbitan and mixtures thereof.

Besides insert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compounds of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and the like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The slats can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation of a prodrug.

The compounds of the invention can exist in unsolvated as well as solvated forms, including hydrated forms, such as hemi-hydrates. In general, the solvated forms, the pharmaceutically acceptable solvents such as water and ethanol among others are equivalent to the unsolvated forms for the purposes of the invention.

The total daily dose of the compounds of this invention administered to a human of lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dosage.

Compounds of the present invention were named by ACD/ChemSketch version 5.0 (developed by Advanced Chemistry Development, Inc., Toronto, ON, Canada) or were given names which appeared to be consistent with ACD nomenclature.

Abbreviations

Abbreviations which have been used in the descriptions of the Schemes and the Examples that follow are: DBU for 1,8-diazabicyclo[5.4.0]undec-7-ene; DCC for 1,3-dicyclohexylcarbodiimide; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; HPLC high pressure liquid chromatography; NBS for N-bromosuccinimide; psi for pounds per square inch; and THF for tetrahydrofuran.

Preparation of Compounds of the Present Invention

The compounds and processes of the present invention will be better understood in connection with the following synthetic Schemes and Examples which illustrate a means by which the compounds of the present invention can be prepared.

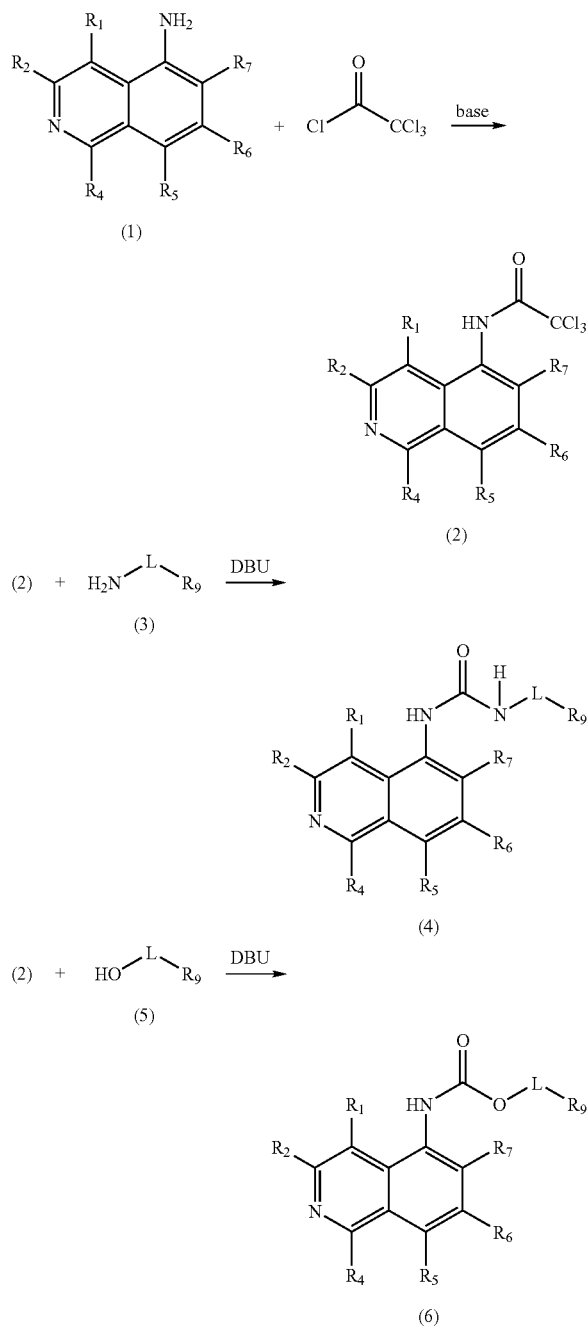

romethane to provide trichloroacetamides of general formula (2). Trichloroacetamides of general formula (2) can be treated with amines of general formula (3) and a non-nucleophilic base such as, but not limited to, DBU in a solvent such as, but not limited to, acetonitrile to provide ureas of general formula (4).

Carbamates of general formula (6), wherein $R_1$, $R_2$, $R_4$, $R_5$, $R_6$, $R_7$, $R_9$ and L are as defined in formula (I), may also be prepared as described in Scheme 1. Trichloroacetamides of general formula (2) can be treated with alcohols of general formula (5) and a non-nucleophilic base such as, but not limited to, DBU in a solvent such as, but not limited to, acetonitrile to provide carbamates of general formula (6).

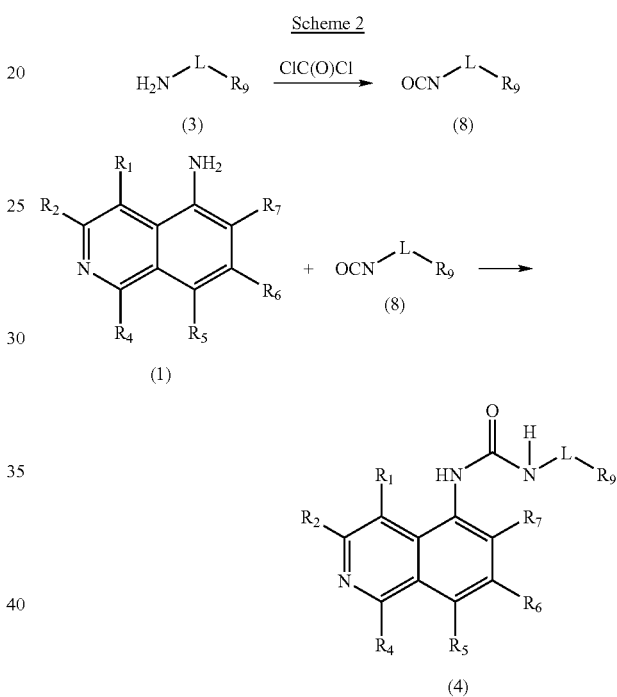

Ureas of general formula (4), wherein $R_1$, $R_2$, $R_4$, $R_5$, $R_6$, $R_7$, $R_9$, and L are as defined in formula (I), may be prepared as described in Scheme 2. Amines of general formula (3) can be treated with phosgene or triphosgene and DMAP in a solvent such as, but not limited to, dichloromethane to provide isocyanates of general formula (8). 5-Aminoisoquinolines of general formula (1) can be treated with isocyanates of general formula (8) in a solvent such as, but not limited to, toluene or THF or a combination thereof to provide ureas of general formula (4).

Ureas of general formula (4), wherein $R_1$, $R_2$, $R_4$, $R_5$, $R_6$, $R_7$, $R_9$, and L are as defined in formula (I), may be prepared as described in Scheme 1. 5-Aminoisoquinolines of general formula (1), purchased commercially or prepared using standard chemistry known to those in the art, can be treated with trichloroacetyl chloride and a base such as, but not limited to, triethylamine in a solvent such as dichlo- Scheme 3

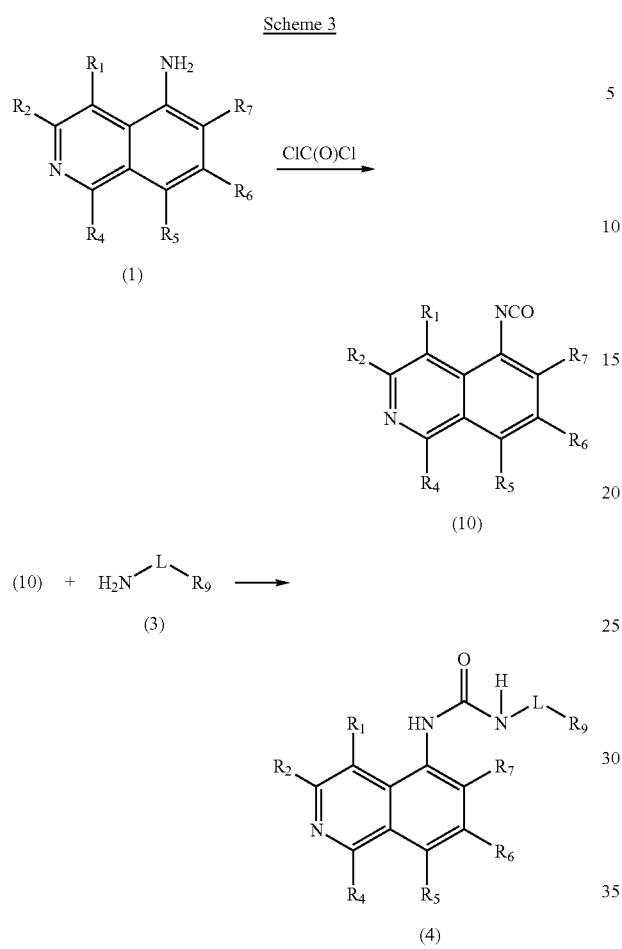

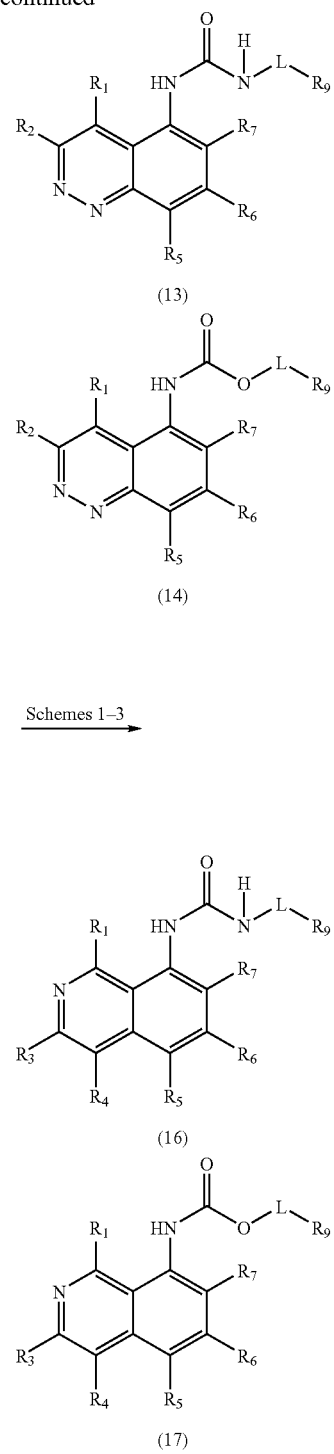

Ureas of general formula (4), wherein $R_1$, $R_2$, $R_4$, $R_5$, $R_6$, $R_7$, $R_9$, and L are as defined in formula (I), may be prepared as described in Scheme 3. 5-Aminoisoquinolines of general formula (1) can be treated with phosgene or triphosgene and DMAP in a solvent such as, but not limited to, dichloromethane to provide isocyanates of general formula (10). Isocyanates of general formula (10) can be treated with amines of general formula (3) in a solvent such as, but not limited to, toluene or THF or a combination thereof to provide ureas of general formula (4).

Scheme 4

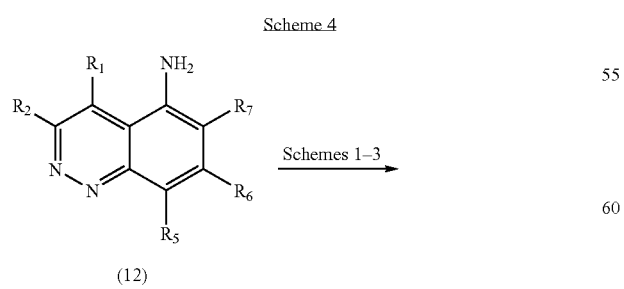

Ureas of general formula (13), wherein $R_1$, $R_2$, $R_5$, $R_6$, $R_7$, $R_9$, and L are as defined in formula (I), and carbamates of general formula (14), wherein $R_1$, $R_2$, $R_5$, $R_6$, $R_7$, $R_9$ and L are as defined in formula (I), may be prepared as described in Scheme 4. 5-Aminocinnolines of general formula (12), purchased commercially or prepared using standard chemistry known to those in the art, may be processed as described in Schemes 1–3 to provide ureas of general formula (13) and carbamates of general formula (14).

Ureas of general formula (16), wherein $R_1$, $R_3$, $R_4$, $R_5$, $R_6$, $R_7$, $R_9$ and L are as defined in formula (I), and carbamates of general formula (17), wherein $R_1$, $R_3$, $R_4$, $R_5$, $R_6$, $R_7$, $R_9$ and L are as defined in formula (I), may be prepared as described in Scheme 4. 8-Aminoisoquinolines of general formula (15), purchased commercially or prepared using standard chemistry known to those in the art, may be processed as described in Schemes 1–3 to provide ureas of general formula (16) and carbamates of general formula (17).

Scheme 5

(19)

(20)

(21)

(22)

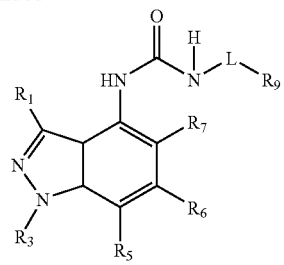

(23)

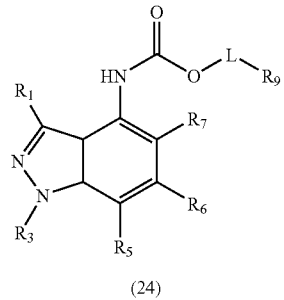

(24)

Ureas of general formula (20), wherein $R_1$, $R_2$, $R_3$, $R_5$, $R_6$, $R_7$, $R_9$, and L are as defined in formula (I), and carbamates of general formula (21), wherein $R_1$, $R_2$, $R_3$, $R_5$, $R_6$, $R_7$, $R_9$, and L are as defined in formula (I), may be prepared as described in Scheme 5. 4-Aminoindoles of general formula (19), purchased commercially or prepared using standard chemistry known to those in the art, may be processed as described in Schemes 1–3 to provide ureas of general formula (20) and carbamates of general formula (21).

Ureas of general formula (23), wherein $R_1$, $R_3$, $R_5$, $R_6$, $R_7$, $R_9$ and L are as defined in formula (I), and carbamates of general formula (24), wherein $R_1$, $R_3$, $R_5$, $R_6$, $R_7$, $R_9$, and L are as defined in formula (I), may be prepared as described in Scheme 5. -Aminoindazoles of general formula (22), purchased commercially or prepared using standard chemistry known to those in the art, may be processed as described in Schemes 1–3 to provide ureas of general formula (23) and carbamates of general formula (24).

Scheme 6

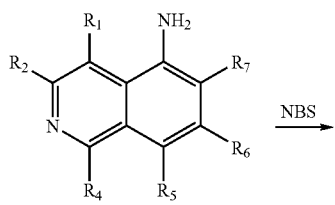

(1)

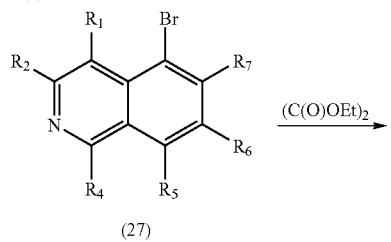

(27)

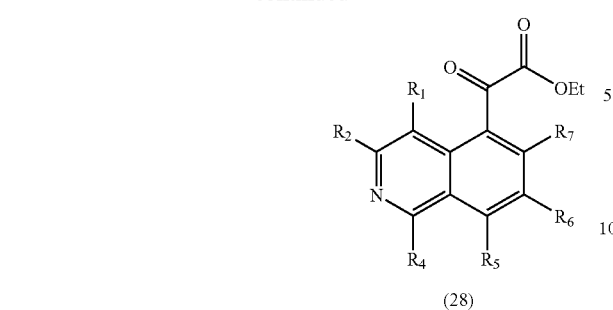

Amides of general formula (32), wherein $R_1$, $R_2$, $R_4$, $R_5$, $R_6$, $R_7$, $R_9$, and L are as defined in formula (I), can be prepared as described in Scheme 6. Amines of general formula (1) can be treated with an acid such as, but not limited to, concentrated sulfuric acid and N-bromosuccinimide to provide bromides of general formula (27). Bromides of general formula (27) can be treated with an organolithium reagent such as, but not limited to, n-butyllithium and diethyl oxalate in a solvent such as, but not limited to, THF to provide keto esters of general formula (28). Keto esters of general formula (28) can be treated with a reducing agent such as, but not limited to, 10% Pd/C under a hydrogen atmosphere (50 psi) in a solvent such as, but not limited to, ethanol to provide hydroxy esters of general formula (29). Hydroxy esters of general formula (29) can be treated with an acid chloride such as, but not limited to, acetyl chloride in a solvent such as, but not limited to, pyridine to provide diesters of general formula (30). Diesters of general formula (30) can be treated with 10% Pd/C and a base such as, but not limited to, triethylamine under a hydrogen atmosphere (60 psi) in a solvent such as, but not limited to, ethanol to provide esters of general formula (31). Esters of general formula (31) can be treated with amines of general formula (3) to provide amides of general formula (32). Alternatively, esters of general formula (31) can be treated with aqueous base such as, but not limited to, aqueous sodium hydroxide or aqueous potassium hydroxide to provide the acids which can be then be converted into amides of general formula (32) by treatment with amines of general formula (3) under standard DCC or EDCI coupling procedures that are well known in the art.

Esters of general formula (33), wherein $R_1$, $R_2$, $R_4$, $R_5$, $R_6$, $R_7$, $R_9$ and L are as defined in formula (I), can be prepared as described in Scheme 6. Esters of general formula (31) can be treated with alcohols of general formula (5) under standard transesterification conditions well known to those of skill in the art to provide esters of general formula (33).

The following Examples are intended as an illustration of and not a limitation upon the scope of the invention as defined in the appended claims.

EXAMPLE 1

N-[2-(3-fluorophenyl)ethyl]-N'-isoquinolin-5-ylurea

EXAMPLE 1A 2,2,2-trichloro-N-isoquinolin-5-ylacetamide

A solution of 5-aminoisoquinoline (1.0 g, 6.9 mmol) in dichloromethane (40 mL) and Et$_3$N (1 mL) at 5° C. was treated with trichloroacetyl chloride (1.38 g, 7.6 mmol) dropwise. The reaction mixture was stirred at ambient temperature for 14 hours, concentrated, diluted with ethyl acetate and washed with 1N HCl. The aqueous layer was treated with aqueous $NaHCO_3$ and extracted with ethyl acetate. The organic layer the was washed with water and concentrated. The solid residue was suspended in ethyl acetate (5 mL) and filtered to obtain 1.3 g (65%) of the title compound as a tan solid. $^1H$ NMR (300 MHz, $d_6$-DMSO) δ 11.20 (broad s, 1H), 9.41, (s, 1H), 8.60 (d, 1H), 8.18 (m, 1H), 7.77 (m, 2H), 7.66 (d, 1H); MS (DCI/$NH_3$) m/z 289 $(M+H)^+$.

EXAMPLE 1B

N-[2-(3-fluorophenyl)ethyl]-N'-isoquinolin-5-ylurea

The product from Example 1A (0.65 g, 2.25 mmol), DBU (0.85 g, 5.6 mmol) and 2-(3-fluorophenyl)ethylamine (0.35 g, 2.5 mmol) in acetonitrile (50 mL) were refluxed for 10 hours. The mixture was cooled, concentrated, diluted with ethyl acetate, washed twice with aqueous ammonium chloride and concentrated to dryness. The solid obtained was suspended in ethyl acetate and filtered to obtain 0.45 g (65%) of the title compound as a tan solid. $^1H$ NMR (300 MHz, $d_6$-DMSO) δ 9.27 (s, 1H), 8.63 (s, 1H), 8.51 (d, 1H), 8.26 (d, 1H), 7.89 (d, 1H), 7.71 (d, 1H), 7.59 (m, 1H), 7.35 (m, 1H), 7.18–7.0 (m, 3H), 6.60 (t, 1H), 3.42 (m, 2H), 2.72 (m, 2H); MS (DCI/$NH_3$) m/z 310 $(M+H)^+$; Anal. Calcd. For $C_{18}H_{16}N_3FO$. $0.1H_2O$: C 69.48; H 5.25; N 13.51. Found: C 69.31; H 5.25; N 13.46.

EXAMPLE 2

N-[2-(3-bromophenyl)ethyl]-N'-isoquinolin-5-ylurea

The title compound was prepared using 2-(3-bromophenyl)ethylamine, DBU, the product from Example 1A and the procedure described in Example 1B. $^1H$ NMR (300 MHz, $d_6$-DMSO) δ 9.26 (s, 1H), 8.63 (s, 1H), 8.51 (d, 1H), 8.23 (d, 1H), 7.90 (d, 1H), 7.71 (d, 1H), 7.59 (m, 1H), 7.40 (m, 2H), 7.29 (m, 2H), 6.60 (t, 1H), 3.42 (m, 2H), 2.80 (m, 2H); MS (DCI/$NH_3$) m/z 370 $(M+H)^+$; Anal. Calcd. For $C_{18}H_{16}N_3BrO$: C 58.39; H 4.36; N 11.35. Found: C 58.17; H 4.46; N 11.28.

EXAMPLE 3

N-isoquinolin-5-yl-N'-[4-(trifluoromethyl)benzyl]urea

The title compound was prepared using 4-(trifluoromethyl)benzylamine, DBU, the product from Example 1A and the procedure described in Example 1B. $^1H$ NMR (300 MHz, $d_6$-DMSO) 9.26 (s, 1H), 8.82 (s, 1H), 8.52 (d, 1H), 8.26 (d, 1H), 7.94 (d, 1H), 7.71 (m, 3H), 7.58 (m, 3H), 7.20 (t, 1H), 4.48 (d, 2H); MS (DCI/$MH_3$) m/z 346 $(M+H)^+$; Anal. Calcd. For $C_{18}H_{14}N_3F_3O$. $0.05H_2O$: C 62.63; H 4.19; N 12.04. Found: C 62.41; H 4.58; N 11.44.

EXAMPLE 4

N-isoquinolin-5-yl-N'-(4-phenoxybenzyl)urea

The title compound was prepared using 4-phenoxybenzylamine, DBU, the product from Example 1A and the procedure described in Example 1B. $^1H$ NMR (300 MHz, $d_6$-DMSO) δ 9.30 (s, 1H), 8.75 (s, 1H), 8.58 (d, 1H), 8.31 (d, 1H), 7.92 (d, 1H), 7.75 (d, 1H), 7.60 (t, 1H), 7.40 (m, 4H), 7.18–6.95 (m, 6H), 4.38 (d, 2H); MS (DCI/$MH_3$) m/z 369 $(M+H)^+$.

EXAMPLE 5

N-[3-fluoro-5-(trifluoromethyl)benzyl]-N'-isoquinolin-5-ylurea

The title compound was prepared using 3-fluoro-5-(trifluoromethyl)benzylamine, DBU, the product from Example 1A and the procedure described in Example 1B. $^1H$ NMR (300 MHz, $d_6$-DMSO) δ 9.28 (s, 1H), 8.88 (s, 1H), 8.53 (d, 1H), 8.22 (d, 1H), 7.90 (d, 1H), 7.77 (d, 1H), 7.55 (m, 4H), 7.20 t, 1H), 4.45 (d, 2H); MS (DCI/$NH_3$) m/z 364 $(M+H)^+$.

EXAMPLE 6

N-(2,5-dichlorobenzyl)-N'-isoquinolin-5-ylurea

The title compound was prepared using 2,5-dichlorobenzylamine, DBU, the product from Example 1A and the procedure described in Example 1B. $^1H$ NMR (300 MHz, $d_6$-DMSO) δ 9.30 (s, 1H), 8.90 (broad s, 1H), 8.55 (d, 1H), 8.36 (d, 1H), 7.97 (d, 1H), 7.76 (d, 1H), 7.61–7.13 (m, 5H), 4.43 (d, 2H); MS (DCI/$MH_3$) m/z 345 $(M+H)^+$; Anal. Calcd. For $C_{17}H_{13}N_3Cl_2O$. C 58.07; H 3.90; N 11.95. Found: C 57.76; H 3.84; N 11.64.

EXAMPLE 7

N-(1,3-benzodioxol-5-ylmethyl)-N'-isoquinolin-5-ylurea

The title compound was prepared using 1,3-benzodioxol-5-ylmethylamine, DBU, the product from Example 1A and the procedure described in Example 1B. $^1H$ NMR (300 MHz, $d_6$-DMSO) δ 9.27 (s, 1H), 8.85 (broad s, 1H), 8.50 (d, 1H), 8.30 (d, 1H), 8.00 (d, 1H), 7.73 (d, 1H), 7.60 t, 1H), 7.15 (m, 2H), 6.00 (s, 2H), 4.28 (d, 2H); MS (DCI/$NH_3$) m/z 322 $(M+H)^+$; Anal. Calcd. For $C_{17}H_{13}N_3O$. $0.5H_2O.0.8NH_4Cl$: C 57.94; H 5.19; N 14.26. Found: C 57.63; H 5.14; N 14.41.

EXAMPLE 8

N-[4-(4-fluorophenyl)ethyl]-N'-isoquinolin-5-ylurea the title compound was prepared using 2-(4-fluorophenyl)ethylamine, DBU, the product from Example 1A and the procedure described in Example 1B. $^1H$ NMR (300 MHz, $d_6$-DMSO) δ 9.25 (s, 1H), 8.70 (broad s, 1H), 8.50 (d, 1H), 8.27 (d, 1H), 7.93 (d, 1H), 7.71 (d, 1H), 7.60 (t, 1H), 7.30 (m, 2H), 7.13 (m, 2H), 6.70 (t, 1H), 3.40 (m, 2H), 2.80 (m, 2H); MS (DCI/$NH_3$) m/z 310 $(M+H)^+$; Anal. Calcd. For $C_{17}H_{13}N_3FO$. $0.1H_2O.0.2NH_4Cl$: C 67.18; H 5.32; N 13.93. Found: C 66.86; H 5.41; N 13.75.

EXAMPLE 9

N-(3-bromobenzyl)-N'-isoquinolin-5-ylurea

The title compound was prepared using 3-bromobenzylamine, DBU, the product from Example 1A and the procedure described in Example 1B. $^1H$ NMR (300 MHz, $d_6$-DMSO) δ 9.29 (s, 1H), 8.80 (broad s, 1H), 8.53 (d, 1H), 8.25 (d, 1H), 7.93 (d, 1H), 7.77 (d, 1H), 7.58 (m, 2H), 7.48 (m, 1H), 7.30 (m, 2H), 7.10 (t, 1H), 4.39 (d, 2H); MS (DCI/$NH_3$) m/z 356 $(M+H)^+$; Anal. Calcd. For $C_{17}H_{14}N_3BrO$: C 57.32; H 3.96; N 11.80. Found: C 57.06; H 3.90; N 11.45.

EXAMPLE 10

N-[2-(3,4-dimethylphenyl)ethyl]-N'-isoquinolin-5-ylurea

The title compound was prepared using 2-(3,4-dimethylphenyl)ethylamine, DBU, the product from Example 1A and the procedure described in Example 1B. $^1$H NMR (300 MHz, d$_6$-DMSO) δ 9.25 (s, 1H), 8.50 (d, 1H), 8.28 (d, 1H), 7.90 (d, 1H), 7.70 (d, 1H), 7.57 (t, 1H), 7.00 (m, 3H), 6.60 (t, 1H), 3.40 m, 2H), 2.71 (m, 2H), 2.19 (s, 3H), 2.16 (s, 3H); MS (DCI/NH$_3$) m/z 320 (M+H)$^+$; Anal. Calcd. For C$_{20}$H$_{21}$N$_3$O.0.3 H$_2$O; C 73.96; H 6.70; N 12.94. Found: C 73.80; H 6.32; N 12.98.

EXAMPLE 11

N-[1-(4-bromophenyl)ethyl]-N'-isoquinolin-5-ylurea

5-Aminoisoquinoline (0.64 g, 4.42 mmol) in dichloromethane (20 mL) was treated with 1-bromo-4-(1-isocyanatoethyl)benzene (1.0 g, 4.42 mmol) in toluene (10 mL). The mixture was stirred 14 hours at ambient temperature and filtered to obtain 1.2 g (74%) of the product as light grey solid. $^1$H NMR (300 MHz, d$_6$-DMSO) δ 9.28 (s, 1H), 8.68 (broad s, 1H), 8.56 (d, 1H); 8.28 (d, 1H), 7.90 (d, 1H), 7.72 (d, 1H), 7.59 (m, 2H), 7.35 (m, 2H), 7.10 (d, 1H), 4.85 (m, 1H), 1.40 (d, 3H); MS (DCI/NH$_3$) m/z 370 (M+H)$^+$; Anal. Calcd. For C$_{18}$H$_{16}$N$_3$BrO.0.1H$_2$O: C 58.11; H 4.39; N 11.29. Found: C 57.79; H 4.21; N 11.16.

EXAMPLE 12

4-(trifluoromethyl)benzyl isoquinolin-5-ylcarbamate

The title compound was prepared using [4-(trifluoromethyl)phenyl]methanol, DBU, the product from Example 1A and the procedure described in Example 1B. $^1$H NMR (300 MHz, d$_6$-DMSO) δ 9.90 (broad s, 1H), 9.30 (s, 1H), 8.52 (d, 1H), 7.94 (m, 3H), 7.80 d, 2H), 7.70 (m, 3H), 5.30 (s, 2H); MS (DCI/NH$_3$) m/z 347 (M+H)$^+$; Anal. Calcd. For C$_{18}$H$_{13}$N$_2$O$_2$F$_3$: C 62.43; H 3.78; N 8.09. Found: C 62.23; H 3.83; N 7.99.

EXAMPLE 13

2-(3-bromophenyl)ethyl isoquinolin-5-ylcarbamate

The title compound was prepared using 2-(3-bromophenyl)ethanol, DBU, the product from Example 1A and the procedure described in Example 1B. $^1$H NMR (300 MHz, d$_6$-DMSO) δ 9.70 (broad s, 1H), 9.30 (s, 1H), 8.50 (d, 1H), 7.88 (m, 3H), 7.64 (t, 1H), 7.56 (s, 1H), 7.45 (m, 1H), 7.30 (m, 2H), 4.34 (t, 2H), 3.00 (t, 2H); MS (DCI/MH$_3$) m/z 371 (M+H)$^+$; Anal. Calcd. For C$_{18}$H$_{15}$N$_2$O$_2$Br: C 58.24; H4.07; N 7.55. Found: C 58.35; H 4.07; N7.51.

EXAMPLE 14

1-naphthylmethyl isoquinolin-5-ylcarbamate

The title compound was prepared using 1-naphthylmethanol DBU, the product from Example 1A and the procedure described in Example 1B. $^1$H NMR (DMSO-d$_6$) δ 9.85 (s, 1H), 9.31 (s, 1H), 8.48 (d, 1H), 8.15 (d, 1H), 8.04–7.91 (m, 5N), 7.72–7.52 (m, 5H), 5.69 (s, 2H), MS (ESI+) m/z 328 (M+H)$^+$; Anal Calcd. For C$_{21}$H$_{16}$N$_2$O$_2$: C 76.81, H 4.91, N 8.53; Found: C 76.64, H 4.73, N 8.29.

EXAMPLE 15

N-isoquinolin-5-yl-N'-[4-(trifluoromethoxy)benzyl]urea

The title compound was prepared using 4-(trifluoromethyl)benzylamine, DBU, the product from Example 1A and the procedure described in Example 1B. MS (ESI+) m/z 362 (M+H)$^+$; $^1$H NMR (DMSO-d$_6$) δ 4.41 (d, 2H), 7.14 (t, 1H), 7.35 (d, 2H), 7.48 (d, 2H), 7.60 (t, 1H), 7.75 (d, 1H), 7.95 (d, 1H), 8.28 (d, 1H), 8.53 (d, 1H), 8.79 (s, 1H), 9.27 (s, 1H).

EXAMPLE 16

N-(3,4-dichlorobenzyl)-N'-(3-methylcinnolin-5-yl)urea

EXAMPLE 16A 2,2,2-trichloro-N-(3-methylcinnolin-5-yl)acetamide

The title compound was prepared using 3-methylcinnolin-5-amine (commercially available Maybridge), triethylamine, trichloroacetyl chloride and the procedure described in Example 1A.

EXAMPLE 16B

N-(3,4-dichlorobenzyl)-N'-(3-methylcinnolin-5-yl)urea

The title compound was prepared using 3,4-dichlorobenzylamine, the product from Example 16A, DBU and the procedure described in Example 1B. MS (ESI+) m/z 362 (M+)$^+$; $^1$H NMR (DMSO-d$_6$) δ 2.88 (s, 3H), 4.36 (d, 2H), 7.10 (t, 1H), 7.34 (dd, 1H), 7.59 (m, 2H), 7.76 (t, 1H), 8.04 (d, 2H), 8.19 (d, 1H), 8.93 (s, 1H).

EXAMPLE 17

N-isoquinolin-5-yl-N'-(4-methylbenzyl)urea

The title compound was prepared using 4-methylbenzylamine, the product from Example 1A, DBU and the procedure described in Example 1B, MS (ESI+) m/z 292 (M+H)$^+$; $^1$H NMR (DMSO-d$_6$) δ 2.29 (s, 3H), 4.33 (d, 2H), 7.00 (t, 1H), 7.17 (d, 2H), 7.24 (d, 2H), 7.60 (t, 1H), 7.73 (d, 1H), 7.93 (d, 1H), 8.30 (d, 1H), 8.53 (d, 1H), 8.70 (s, 1H), 9.26 (s, 1H).

EXAMPLE 18

N-(4-fluorobenzyl)-N'-isoquinolin-5-ylurea

The title compound was prepared using 4-fluorobenzylamine, the product from Example 1A, DBU and the procedure described in Example 1B. MS (APCI+) m/z 296 (M+H)$^+$; $^1$H NMR (DMSO-d$_6$) δ 4.37 (d, 2H), 7.07 (t, 1H), 7.18 (t, 2H), 7.40 (dd, 2H), 7.60 (t, 1H), 7.74 (d, 1H), 7.94 (d, 1H), 8.28 (d, 1H), 8.54 (d, 1H), 8.74 (s, 1H), 9.27 (s, 1H).

EXAMPLE 19

N-isoquinolin-5-yl-N'-[(trans)-2-phenylcyclopropyl]urea

The title compound was prepared using trans 2-phenylcyclopropylamine hydrochloride, the product from Example 1A, DBU and the procedure described in Example 1B. MS (ESI+) m/z 304 (M+H)$^+$; $^1$H NMR (DMSO-d$_6$) δ 1.21 (m, 2H), 2.05 (m, 1H), 2.82 (m, 1H), 7.00 (d, 1H), 7.17 (t, 3H), 7.27 (t, 2H), 7.60 (t, 1H), 7.74 (d, 1H), 7.88 (d, 1H), 8.26 (d, 1H), 8.53 (d, 1H), 8.57 (s, 1H), 9.27 (s, 1H).

EXAMPLE 20

N-[2-(3,4-dichlorophenyl)ethyl]-N'-isoquinolin-5-ylurea

The title compound was prepared using 2-(3,4-dichlorophenyl)ethylamine, the product from Example 1A, DBU and the procedure described in Example 1B MS (ESI+) m/z 361 (M+H)$^+$; $^1$H NMR (DMSO-d$_6$) δ 2.82 (t, 2H), 3.43 (q, 2H), 6.63 (t, 1H), 7.29 (dd, 1H), 7.59 (m, 3H), 7.73 (d, 1H), 7.88 (d, 1H), 8.23 (d, 1H), 8.52 (d, 1H), 8.65 (s, 1H), 9.26 (s, 1H).

EXAMPLE 21

N-[2-(3,5-dimethoxyphenyl)ethyl]-N'-isoquinolin-5-ylurea

The title compound was prepared using 2-(3,5-dimethyoxyphenyl)ethylamine, the product from Example 1A, DBU and the procedure described in Example 1B. MS (ESI+) m/z 352 (M+H)$^+$; $^1$H NMR (DMSO-d$_6$) δ 2.74 (t, 2H), 3.42 (q, 2H), 3.73 (s, 6H), 6.36 (t, 1H), 6.44 (d, 2H), 6.59 (t, 1H), 7.59 (t, 1H), 7.72 (d, 1H), 7.91 (d, 1H), 8.27 (d, 1H), 8.52 (d, 1H), 8.66 (s, 1H), 9.26 (s, 1H).

EXAMPLE 22

N-(4-chlorobenzyl)-N'-isoquinolin-5-ylurea

The title compound was prepared using 4-chlorobenzylamine, the product from Example 1A, DBU and the procedure described in Example 1B. MS (ESI+) m/z 313 (M+H)$^+$; $^1$H NMR (DMSO-d$_6$) δ 4.37 (d, 2H), 7.14 (t, 1H), 7.40 (q, 4H), 7.60 (t, 1H), 7.74 (d, 1H), 7.95 (d, 1H), 8.28 (dd, 1H), 8.53 (d, 1H), 8.80 (s, 1H), 9.27 (s, 1H).

EXAMPLE 23

N-isoquinolin-5-yl-N'-{2-[3-(trifluoromethyl)pheyl]ethyl}urea

The title compound was prepared using 2-[3-(trifluoromethyl)phenyl]ethylamine, the product from Example 1A, DBU and the procedure described in Example 1B. MS (ESI+) m/z 360 (M+H)$^+$; $^1$H NMR (DMSO-d$_6$) δ 2.91 (t, 2H), 3.46 (q, 2H), 6.62 (t, 1H), 7.59 (m, 4H), 7.64 (s, 1H), 7.73 (d, 1H), 7.87 (d, 1H), 8.23 (d, 1H), 8.51 (d, 1H), 8.64 (s, 1H), 9.26 (s, 1H).

EXAMPLE 24

N-[2-(2,6-dichlorophenyl)ethyl]-N'-isoquinolin-5-ylurea

The title compound was prepared using 2-(2,6-dichlorophenyl)ethylamine, the product from Example 1A, DBU and the procedure described in Example 1B. MS (ESI+) m/z 361 (M+H)$^+$; $^1$H NMR (DMSO-d$_6$) δ 3.12 (t, 2H), 3.40 (q, 2H), 6.72 (t, 1H), 7.28 (t, 1H), 7.46 (d, 2H), 7.58 (t, 1H), 7.72 (d, 1H), 7.87 (d, 1H), 8.19 (d, 1H), 8.51 (d, 1H), 8.60 (s, 1H), 9.25 (s, 1H).

EXAMPLE 25

N-[2-(2,3-dichlorophenyl)ethyl]-N'-isoquinolin-5-ylurea

The title compound was prepared using 2-(2,3-dichlorophenyl)ethylamine, the product from Example 1A, DBU and the procedure described in Example 1B. MS (ESI+) m/z 361 (M+H)$^+$; $^1$H NMR (DMSO-d$_6$) δ 3.01 (t, 2H), 3.46 (q, 2H), 6.67 (t, 1H), 7.34 (t, 1H), 7.38 (dd, 1H), 7.53 (dd, 1H), 7.59 (t, 1H), 7.74 (d, 1H), 7.87 (d, 1H), 8.21 (d, 1H), 8.52 (d, 1H), 8.64 (s, 1H), 9.26 (s, 1H).

EXAMPLE 26

N-isoquinolin-5-yl-N'-[3-(trifluoromethoxy)benzyl]urea

The title compound was prepared using 3-(trifluoromethoxy)benzylamine, the product from Example 1A, DBU and the procedure described in Example 1B. MS (ESI+) m/z 362 (M+H)$^+$; $^1$H NMR (DMSO-d$_6$) δ 4.44 (d, 2H), 7.15 (t, 1H), 7.26 (d, 1H), 7.34 (s, 1H), 7.40 (d, 1H), 7.50 (t, 1H), 7.61 (t, 1H), 7.76 (d, 1H), 7.95 (d, 1H), 8.25 (d, 1H), 8.53 (d, 1H), 8.80 (s, 1H), 9.28 (s, 1H).

EXAMPLE 27

N-[2-(4-ethoxy-3-methoxyphenyl)ethyl]-N'-isoquinolin-5-ylurea

The title compound was prepared using 2-(4-ethoxy-3-methoxyphenyl)ethylamine, the product from Example 1A. DBU and the procedure described in Example 1B. MS (ESI+) m/z 366 (M+H)$^+$; $^1$H NMR (DMSO-d$_6$) δ 1.31 (t, 3H), 2.73 (t, 2H), 2.73 (t, 2H), 3.40 (q, 2H), 3.76 (s, 3H), 3.97 (q, 2H), 6.62 (t, 1H), 6.76 (dd, 1H), 6.87 (d, 2H), 7.59 (t, 1H), 7.72 (d, 1H), 7.93 (d, 1H), 8.28 (d, 1H), 8.52 (d, 1H), 8.69 (s, 1H), 9.26 (s, 1H).

EXAMPLE 28

N-[2-(2,4-dichlorophenyl)ethyl]-N'-isoquinolin-5-ylurea

The title compound was prepared using 2-(2,4-dichlorophenyl)ethylamine, the product from Example 1A, DBU and the procedure described in Example 1B. $^1$H NMR (DMSO-d$_6$) δ 9.26 (s, 1H); 8.62 (s, 1H); 8.53 (d, 1H); 8.22 (dd, 1H); 7.88 (d, 1H); 7.74 (d, 1H); 7.61 (m, 1H); 7.57 (d, 1H); 7.42 (m, 2H); 6.64 (t, 1H); 3.43 (q, 2H); 2.93 (t, 2H).

EXAMPLE 29

N-(3-bromo-4-fluorobenzyl)-N'-isoquinolin-5-ylurea

The title compound was prepared using 3-bromo-4-fluorobenzylamine, the product from Example 1A, DBU and the procedure described in Example 1B. MS (ESI+) m/z 376 (M+H)$^+$; $^1$H NMR (DMSO-d$_6$) δ 9.55 (s, 1H); 9.06 (s, 1H); 8.64 (d, 1H); 8.64 (d, 1H); 8.42 (d, 1H); 8.25 (d, 1H); 7.95 (d, 1H); 7.76 (t, 1H); 7.70 (dd, 1H); 7.38 (m, 2H); 7.15 (m, 2H); 4.35 (d, 2H).

EXAMPLE 30

N-(3,4-dimethylbenzyl)-N'-isoquinolin-5-ylurea

The title compound was prepared using 3,4-dimethylbenzylamine, the product from Example 1A, DBU and the procedure described in Example 1B. MS (ESI+) m/z 307 M+H)$^+$; $^1$H NMR (DMSO-d$_6$) δ 9.55 (s, 1H), 8.98 (s, 1H); 8.62 (d, 1H), 8.46 (d, 1H); 8.25 (d, 1H); 7.94 (d, 1H); 7.78 (t, 1H); 7.08 (m, 3H); 6.95 (m, 2H); 4.30 (d, 2H); 2.20 (s, 3H); 2.18 (s, 3H).

EXAMPLE 31

N-isoquinolin-5-yl-N'-(3phenylpropyl)urea

The title compound was prepared using 3-phenylpropylamine, the product from Example 1A, DBU and the procedure described in Example 1B, MS (ESI+) m/z 306 (M+H)$^+$; $^1$H NMR (DMSO-d$_6$) δ 9.61 (s, 1H); 9.05 (s, 1H); 8.65 (d, 1H); 8.50 (d, 1H); 8.40 (d, 1H); 7.96 (d, 1H); 7.80 (t, 1H); 7.21 (m, 6H); 6.92 (t, 1H); 3.18 (q, 2H); 2.65 (t, 2H); 1.78 (m, 2H).

EXAMPLE 32

N-(3,5-dichlorobenzyl)-N'-isoquinolin-5-ylurea

The title compound was prepared using 3,5-dichlorobenzylamine, the product from Example 1A, DBU and the procedure described in Example 1B. MS (ESI+) m/z 347 (M+H)+; $^1$H NMR (DMSO-d$_6$) δ 9.60 (s, 1H); 9.18 (s, 1H); 8.65 (d, 1H); 8.44 (d, 1H); 8.35 (d, 1H); 7.96 (d, 1H); 7.80 (t, 1H); 7.43 (dt, 1H); 7.40 (m, 2H); 7.35 (m, 1H); 7.25 (d, 1H); 4.40 (d, 2H).

EXAMPLE 33

N-(3-chloro-4-methylbenzyl)-N'-isoquinolin-5-ylurea

The title compound was prepared using 3-chloro-4-methylbenzylamine, the product from Example 1A, DBU and the procedure described in Example 1B. MS (ESI+) m/z 326 (M+H)+; $^1$H NMR (DMSO-d$_6$) δ 9.65 (s, 1H); 9.20 (s, 1H); 8.65 (d, 1H); 8.50 (d, 1H); 8.40 (d, 1H); 8.00 (d, 1H); 7.80 (t, 1H); 7.30 (m, 5H); 4.35 (d, 2H); 2.30 (s, 3H).

EXAMPLE 34

N-isoquinolin-5-yl-N'-(2-phenoxyethyl)urea

The title compound was prepared using 2-phenoxyethylamine, the product from Example 1A, DBU and the procedure described in Example 1B. MS (ESI+) m/z 308 (M+H)+; $^1$H NMR (DMSO-d$_6$) δ 9.50 (s, 1H); 8.98 (s, 1H); 8.61 (d, 1H); 8.45 (d, 1H); 8.20 (d, 1H); 7.90 (d, 1H); 7.75 (t, 1H); 7.26 (m, 3H); 6.95 (m, 4H); 4.00 (t, 2H); 3.50 (m, 2H).

EXAMPLE 35

N-(3,4-dichlorobenzyl)-N'-isoquinolin-5-ylurea

The title compound was prepared using 3,4-dichlorobenzylamine, the product from Example 1A, DBU and the procedure described in Example 1B. MS (ESI−) m/z 344 (M−H)−; $^1$H NMR (300 MHz, DMSO-d$_6$) δ 9.27 (s, 1H), 8.82 (bs, 1H), 8.54 (d, 1H), 8.25 (m, 1H), 7.94 (d, 1H), 7.76 (d, 1H), 7.56–7.65 (m, 3H), 7.35 (m, 1H), 7.15 (t, 1H), 4.38 (d, 2H); Anal. Calcd for C$_{17}$H$_{13}$Cl$_2$N$_3$O: C, 58.98; H, 3.78; N, 12.14. Found: C, 59.02; H, 3.70; N, 12.10.

EXAMPLE 36

N-(3-fluorobenzyl)-N'-isoquinolin-5-ylurea

The title compound was prepared using 3-fluorobenzylamine, the product from Example 1A, DBU and the procedure described in Example 1B. MS (ESI−) m/z 294 (M−H)−; $^1$H NMR (300 MHz, DMSO-d$_6$) δ 9.28 (s, 1H), 8.80 (bs, 1H), 8.54 (d, 1H), 8.28 (m, 1H), 7.95 (d, 1H), 7.76 (d, 1H), 7.60 (t, 1H), 7.35–7.45 (m, 1H), 7.05–7.15 (m, 4H), 4.40 (d, 2H); Anal. Calcd for C$_{17}$H$_{14}$FN$_3$O: C, 69.14; H, 4.78; N, 14.23 Found: C, 68.98; H, 4.83; N, 14.27.

EXAMPLE 37

N-(4-tert-butylbenzyl)-N'-isoquinolin-5-ylurea

The title compound was prepared using 4-tert-butylbenzylamine, the product from Example 1A, DBU and the procedure described in Example 1B. MS (ESI+) m/z 324 (M+H)+; $^1$H NMR (300 MHz, DMSO-d$_6$) δ 9.26 (s, 1H), 8.70 (bs, 1H), 8.53 (d, 1H), 8.31 (dd, 1H), 7.92 (d, 1H), 7.73 (d, 1H), 7.60 (t, 1H), 7.38 (m, 2H), 7.28 (m, 2H), 7.01 (t, 1H), 4.32 (d, 2H), 1.27 (s, 9H). Anal. Calcd for C$_{21}$H$_{23}$N$_3$O•0.3 H$_2$O: C, 74.44; H, 7.02; N, 12.40. Found: C, 74.19; H, 6.88; N, 12.33.

EXAMPLE 38

N-isoquinolin-5-yl-N'-[2-(3-methylphenyl)ethyl]urea

The title compound was prepared using 2-(3-methylphenyl)ethylamine, the product from Example 1A, DBU and the procedure described in Example 1B. MS (ESI+) m/z 306 (M+H)+; $^1$H NMR (300 MHz, DMSO-d$_6$) δ 9.26 (m, 1H), 8.66 (bs, 1H), 8.52 (d, 1H), 8.28 (dd, 1H), 7.90 (d, 1H), 7.72 (d, 1H), 7.59 (t, 1H), 7.21 (t, 1H), 7.00–7.11 (m, 3H), 6.60 (t, 1H), 3.41 (m, 2H), 2.76 (t, 2H), 2.30 (s, 3H); Anal. Calcd for C$_{19}$H$_{19}$N$_3$O•0.1 H$_2$O: C, 74.29; H, 6.30; N, 13.68. Found: C, 74.06; H, 6.43; N, 13.76.

EXAMPLE 39

N-isoquinolin-5-yl-N'-[2-(4-methylphenyl)ethyl]urea

The title compound was prepared using 2(3-methylphenyl)ethylamine, the product from Example 1A, DBU and the procedure described in Example 1B. MS (ESI+) m/z 306 (M+H)+; $^1$H NMR (300 MHz, DMSO-d$_6$) δ 9.26 (s, 1H), 8.66 (bs, 1H), 8.52 (d, 1H), 8.28 (m, 1H), 7.90 (d, 1H), 7.72 (d, 1H), 7.59 (t, 1H), 7.10–7.20 (m, 4H), 6.58 (t, 1H), 3.40 (m, 2H), 2.75 (t, 2H), 2.28 (s, 3H); Anal. Calcd for C$_{19}$H$_{19}$N$_3$O•0.2 H$_2$O: C, 73.86; H, 6.33; N, 13.60. Found: C, 73.69; H, 6.53; N, 13.51.

EXAMPLE 40

N-[2-(2,4-dimethylphenyl)ethyl]-N'-isoquinolin-5-ylurea

The title compound was prepared using 2-(2,4-dimethylphenyl)ethylamine, the product from Example 1A, DBU and the procedure described in Example 1B. MS (ESI+) m/z 320 (M+H)+; $^1$H NMR (300 MHz, DMSO-d$_6$) δ 9.26 (s, 1H), 8.66 (bs, 1H), 8.53 (d, 1H), 8.28 (m, 1H), 7.90 (d, 1H), 7.73 (d, 1H), 7.59 (t, 1H), 7.08 (d, 1H), 6.92–7.02 (m, 2H), 6.63 (t, 1H), 3.34 (m, 2H), 2.75 (t, 2H), 2.29 (s, 3H), 2.24 (s, 3H); Anal. Calcd for C$_{20}$H$_{21}$N$_3$O•0.45 H$_2$O: C, 73.35; H, 6.74; N, 12.83. Found: C, 73.70; H, 6.53; N, 12.45.

EXAMPLE 41

N-isoquinolin-5-yl-N'-[2-(2-methylphenyl)ethyl]urea

The title compound was prepared using 2-(2-methylphenyl)ethylamine, the product from Example 1A, DBU and the procedure described in Example 1B. MS (ESI−) m/z 324 (M−H)−; $^1$H NMR (300 MHz, DMSO-d$_6$) δ 9.26 (s, 1H), 8.64 (bs, 1H), 8.53 (d, 1H), 8.25 (m, 1H), 7.89 (d, 1H), 7.73 (d, 1H), 7.59 (t, 1H), 7.46 (dd, 1H), 7.40 (dd, 1H), 7.23–7.36 (m, 2H), 6.67 (t, 1H), 3.44 (m, 2H), 2.94 (t, 2H); Anal. Calcd for C$_{18}$H$_{16}$ClN$_3$O: C, 66.36; H, 4.95; N, 12.90. Found: C, 66.19; H, 4.87; N, 12.91.

EXAMPLE 42

N-isoquinolin-5-yl-N'-{4-[(trifluoromethyl)thio]benzyl}urea

The title compound was prepared using 4-[(trifluoromethyl)thio]benzylamine, the product from Example 1A, DBU and the procedure described in Example 1B. MS (ESI−) m/z 376 (M−H)−; $^1$H NMR (300 MHz, DMSO-d$_6$) δ 9.27 (s, 1H), 8.82 (bs, 1H), 8.54 (d, 1H), 8.27 (dd, 1H), 7.95 (d, 1H), 7.68–7.78 (m, 3H), 7.60 (t, 1H), 7.51 (d, 2H), 7.17 (t, 1H), 4.45 (d, 2H); Anal. Calcd for C$_{18}$H$_{14}$F$_3$N$_3$OS: C, 57.29; H, 3.74; N, 11.13. Found: C, 57.00; H, 3.73; N, 11.04.

EXAMPLE 42

N-isoquinolin-5-yl-N'-[3-(trifluoromethyl)benzyl]urea

The title compound was prepared using 3-(trifluoromethyl)benzylamine, the product from Example 1A, DBU and the procedure described in Example 1B. MS (ESI−) m/z 344 (M−H)⁻; ¹H NMR (300 MHz, DMSO-$d_6$) δ 9.27 (s, 1H), 8.82 (bs, 1H), 8.53 (d, 1H), 8.25 (dd, 1H), 7.94 (d, 1H), 7.55–7.79 (m, 6H), 7.18 (t, 1H), 4.47 (d, 2H); Anal. Calcd for $C_{18}H_{14}F_3N_3O$: C, 62.61; H, 4.09; N, 12.17. Found: C, 62.39; H, 3.87; N, 12.28.

EXAMPLE 43

N-isoquinolin-5-yl-N'-(4-methoxybenzyl)urea

The title compound was prepared using 4-methoxybenzylamine, the product from Example 1A, DBU and the procedure described in Example 1B. MS (ESI−) m/z 306 (M−H)⁻; ¹H NMR (300 MHz, DMSO-$d_6$) δ 9.26 (s, 1H), 8.70 (bs, 1H), 8.53 (d, 1H), 8.31 (dd, 1H), 7.92 (d, 1H), 7.73 (d, 1H), 7.60 (t, 1H), 7.29 (m, 2H), 6.88–7.03 (m, 3H), 4.30 (d, 2H), 3.74 (s, 3H), Anal. Calcd. for $C_{18}H_{17}N_3O_2$: C, 70.34; H, 5.58; N, 13.67. Found: C, 70.21; H, 5.47; N, 13.46.

EXAMPLE 44

N-[4-chloro-3-(trifluoromethyl)benzyl]-N'-isoquinolin-5-ylurea

The title compound was prepared using 4-chloro-3-(trifluoromethyl)benzylamine, the product from Example 1A, DBU and the procedure described in Example 1B. MS (ESI−) m/z 378 (M−H)⁻; ¹H NMR (300 MHz, DMSO-$d_6$) δ 9.73 (s, 1H), 9.53 (s, 1H), 8.69 (d, 1H), 8.61 (d, 1H), 8.54 (d, 1H), 8.07 (d, 1H), 7.82–7.92 (m, 2H), 7.63–7.75 (m, 3H), 4.47 (d, 2H); Anal. Calcd for $C_{18}H_{13}ClF_3N_3O \cdot 1.2$ HCl: C, 51.05; H, 3.38; N, 9.92. Found: C, 51.26; H, 3.68; N, 9.50.

EXAMPLE 45

N-(3,5-dimethylbenzyl)-N'-isoquinolin-5-ylurea

The title compound was prepared using 3,4-dimethylbenzylamine, the product from Example 1A, DBU and the procedure described in Example 1B. MS (ESI−) m/z 304 (M−H)⁻; ¹H NMR (300 MHz, DMSO-$d_6$) δ 9.74 (s, 1H), 8.69 (d, 1H), 8.62 (d, 2H), 8.05 (d, 1H), 7.88 (t, 1H), 7.44 (t, 1H), 6.96 (bs, 2H), 6.89 (bs, 1H), 4.31 (d, 2H), 2.26 (s, 6H); Anal. Calcd for $C_{19}H_{19}N_3O*1.1$ HCl: C, 66.05; H, 5.86; N, 12.16. Found: C, 66.09; H, 5.38; N, 12.14.

EXAMPLE 46

N-(3,5-difluorobenzyl)-N'-isoquinolin-5-ylurea

The title compound was prepared using 3,5-difluorobenzylamine, the product from Example 1A, DBU and the procedure described in Example 1B. MS (ESI+) m/z 312 (M−H)⁻; ¹H NMR (300 MHz, DMSO-$d_6$) δ 9.76 (s, 1H), 9.66 (bs, 1H), 8.65–8.79 (m, 2H), 8.60 (d, 1H), 8.08 (d, 1H), 7.89 (t, 1H), 7.77 (t, 1H), 7.02–7.18 (m, 3H), 4.43 (d, 2H); Anal. Calcd for $C_{17}H_{13}F_2N_3O*0.3$ $H_2O$: C, 57.49; H, 4.14; N, 11.83. Found: C, 57.76; H, 4.59; N, 11.76.

EXAMPLE 47

N-hexyl-N'-isoquinolin-5-ylurea

The title compound was prepared using hexylamine, the product from Example 1A, DBU and the procedure described in Example 1B. MS (ESI−) m/z 270 (M−H)⁻; ¹H NMR (DMSO-$d_6$) δ 9.25 (s, 1H, 8.60 (s, 1H), 8.55 (d, 1H), 8.39 (d, 1H), 7.93 (d, 1H), 7.71 (d, 1H), 7.59 (t, 1H), 6.60 (t, 1H), 3.15 (q, 2H), 1.49 (m, 2H), 1.32 (m, 6H), 0.90 (m, 3H).

EXAMPLE 48

N-(4-bromobenzyl)-N'-isoquinolin-5-ylurea

The title compound was prepared using 4-bromobenzylamine, the produce from Example 1A, DBU and the procedure described in Example 1B. MS (ESI−) m/z 355 (M−H)⁻; ¹H NMR (DMSO-$d_6$) δ 9.27 (s, 1H), 8.78 (s, 1H), 8.53 (d, 1H), 8.27 (d, 1H), 7.93 (d, 1H, 7.74 (d, 1H), 7.61 (d, 1H), 7.55 (d, 2H), 7.42 (d, 2H) 7.10 (t, 1H); Anal. Calcd for $C_{17}H_{14}BrN_3O$: C, 57.32; H, 3.96; N, 11.80. Found C, 57.05; H, 3.79; N, 11.64.

EXAMPLE 49

N-(3,5-dimethoxybenzyl)-N'-isoquinolin-5-ylurea

The title compound was prepared using 3,5-dimethoxybenzylamine, the product from Example 1A, DBU and the procedure described in Example 1B. MS (ESI−) m/z 336 (M−H)³¹; ¹H NMR (DMSO-$d_6$) δ 9.70 (s, 1H), 9.32 (s, 1H), 8.69 (d, 1H), 8.55 (dd, 2H), 8.10 (d, 1H), 7.85 (t, 1H), 7.39 (t, 1H), 6.54 (s, 2H), 6.41 (s, 1H) 4.35 (d, 2H), 3.75 (s, 6H); Anal. Calcd for $C_{19}H_{19}N_3O_3$ 1.25 HCl C, 59.59; H, 5.33; N, 10.97. Found C, 59.22; H, 5.41; N, 10.84.

EXAMPLE 50

N-isoquinolin-5-yl-N'-(3,4,5-trimethoxybenzyl)urea

The title compound was prepared using 3,4,5-trimethoxybenzylamine, the product from Example 1A, DBU and the procedure described in Example 1B. MS (ESI−) m/z 366 M−H)⁻; ¹H NMR (DMSO-$d_6$) δ 9.79 (s, 1H), 9.50 (s, 1H), 8.69 (d, 1H), 8.80 (d, 1H), 8.65 (dd, 2H), 8.08 (d, 1H), 7.90 (d, 1H), 7.68 (m, 1H), 6.71 (s, 2H), 4.53 (d, 2H) 3.79 (s, 6H), 3.53 (s, 3H). Anal. Calcd for $C_{20}H_{21}N_3O_4$ 1.3 HCl: C, 57.91; H, 5.42; N, 10.13. Found C, 57.65; H, 5.60; N, 10.09.

EXAMPLE 51

N-isoquinolin-5-yl-N'-[4-(methylsulfonyl)benzyl]urea

The title compound was prepared using 4-(methylsulfonyl)benzylamine, the product from Example 1A, DBU and the procedure described in Example 1B. MS (ESI−) m/z 354 (M−H)⁻; ¹H NMR (DMSO-$d_6$) δ 9.65 (s, 1H), 9.30 (s, 1H), 8.65 (d, 1H), 8.49 (d, 1H), 8.42 (d, 1H), 8.00 (d, 1H), 7.91 (d, 2H), 7.82 (t, 1H), 7.61 (d, 2H), 7.47 (t, 1H), 4.50 (d, 2H), 3.20 (s, 3H); Anal. Calcd for $C_{20}H_{21}N_3O_4$ 1.0 HCl: C, 55.17; H, 4.63; N, 10.72. Found C, 54.92; H, 4.54; N, 10.42.

EXAMPLE 52

N-(3,4-dimethoxybenzyl)-N'-isoquinolin-5-ylurea

The title compound was prepared using 3,4-dimethoxybenzylamine, the product from Example 1A, DBU and the procedure described in Example 1B. MS (ESI−) m/z (M−H)⁻336; ¹H NMR (DMSO-$d_6$) δ 9.78 (s, 1H), 9.50 (s, 1H), 8.70 (s, 2H), 8.62 (d, 1H), 8.05 (d, 1H), 7.87 (t, 1H), 7.51 (t, 1H), 6.99 (s, 1H), 6.79 (ds, 2H), 4.32 (d, 2H), 3.75 (s, 3H), 3.71 (s, 3H); Anal. Calcd for $C_{19}H_{19}N_3O_3$ 1.0 HCl: C, 61.04; H, 5.39; N, 11.24. Found C, 60.82; H, 5.38; N, 11.19.

EXAMPLE 53

N-isoquinolin-5-yl-N'-(3-phenoxybenzyl)urea

The title compound was prepared using 3,4-dimethoxybenzylamine, the product from Example 1A, DBU and the procedure described in Example 1B. MS (ESI−) m/z 368 (M−H)⁻; $^1$H NMR (DMSO-$d_6$) δ 9.65 (s, 1H), 9.25 (s, 1H), 8.65 (d, 1H), 8.52 (d 1H), 8.48 (d, 1H), 8.03 (d, 1H), 7.82 (t, 1H), 7.35 (m, 4H), 7.15 (d, 2H), 7.05 (s, 2H), 7.00 (s, 1H), 6.84 (d, 1H), 2.37 (d, 2H); Anal. Calcd for $C_{23}H_{19}N_3O_2 \cdot 1.25$ HCl: C, 66.57; H, 4.92; N, 10.13. Found C, 66.49; H, 5.02; N, 10.14.

EXAMPLE 54

N-isoquinolin-5-yl-N'-(1-naphthylmethyl)urea

The title compound was prepared using 1-naphthylmethylamine, the product from Example 1A, DBU and the procedure described in Example 1B. MS (ESI+) m/z 328 (M+H)⁺; HRMS (FAB): Calculated for $C_{21}H_{18}N_O$ 328.1450; observed 328.1438 (M+H)⁺; $^1$H NMR (DMSO-$d_6$) δ 9.25 (s, 1H), 8.48, (d, 1H), 8.39 (d, 1H), 8.22 (d, 1H), 8.19 (d, 1H), 7.97 (d, 1H), 7.87 (d, 1H), 7.78–7.71 (m, 2H), 7.63–7.49 (m, 6H), 4.85 (d, 2H).

EXAMPLE 55

N-(2,4-dimethylbenzyl)-N'-isoquinolin-5-ylurea

The title compound was prepared using 2,4-dimethylbenzylamine, the product from Example 1A, DBU and the procedure described in Example 1B, MS (ESI+) m/z 306 (M+H)⁺; $^1$H NMR (DMSO-$d_6$) δ 9.26 (s, 1H), 8.67 (s, 1H), 8.53 (d, 1H), 8.32 (d, 1H), 7.92 (d, 1H), 7.72 (d, 1H), 7.60 (t, 1H), 7.19 (d, 1H), 7.03–6.95 (m, 2H), 9.90 (t, 1H), 4.31 (d, 2H), 2.30 (s, 3H), 2.26 (s, 3H); Anal. Calcd for $C_{19}H_{19}N_3O*0.2\ H_2O$: C, 73.86, H 6.33, N 13.60. Found: C 73.75, H 6.49, N 13.49.

EXAMPLE 56

N-[4-(dimethylamino)benzyl]-N'-isoquinolin-5-ylurea

The title compound was prepared using 4-(aminomethyl)-N,N-dimethylaniline, the product from Example 1A, DBU and the procedure described in Example 1B. MS (ESI+) m/z 321 (M+H)⁺; $^1$H NMR (DMSO-$d_6$) δ 9.26 (s, 1H), 8.71 (s, 1H), 8.52 (d, 1H), 8.32 (d, 1H), 7.93 (d, 1H), 7.72 (d, 1H), 7.59 (t, 1H), 7.18 (d, 2H), 6.96 (t, 1H), 6.71 (d, 2H), 4.23 (d, 2H), 2.86 (s, 6H); Anal. Calcd for $C_{19}H_{20}N_4O*0.7\ H_2O$: C, 68.53, H 6.48, N 16.82. Found: C 68.59, H 6.48, N 16.60.

EXAMPLE 57

N-isoquinolin-8-yl-N'-[4-(trifluoromethyl)benzyl]urea

EXAMPLE 57A 5-bromoisoquinoline

Concentrated $H_2SO_4$ (260 mL) was cooled to −25° C. while stirring with a mechanical stirrer. Isoquinoline (30 mL, 0.25 mol) was added slowly so the temperature did not exceed 0° C. After the addition was complete, the red solution was recooled to −25° C. and treated with N-bromosuccinimide (55.49 g, 0.31 mol) in small portions so that the temperature did not exceed −20° C. The reaction mixture was stirred for 5 hours keeping the temperature between −30° C. and −18° C. The reaction mixture was then allowed to warm to −10° C. and was poured carefully over 600 g of ice. The resulting slurry was adjusted to pH 10 using 25% $NH_4OH$. The mixture was then extracted with diethyl ether (3×600 mL). The ether fractions were combined, filtered through a celite plug and the filtrate concentrated under reduced pressure. The residue was suspended in hot heptane (600 mL). The heptane was decanted. This procedure was repeated with hexane (2×200 mL). The combined heptane and hexane fractions were concentrated under reduced pressure to give a mustard yellow solid. The title compound was obtained by recrystallization from heptane (26.37 g, 50%). mp 78°–80° C.; MS (ESI+) m/z 209 (M+H)⁺; $^1$H NMR (DMSO, 300 MHz) δ 7.65 (t, J 7.9, 1H), 7.94 (d, J 8.1, 1H), 8.17 (dd, J 1.0, 7.4, 1H), 8.22 (d, J 8.1, 1H), 8.68 (d, J 6.1, 1H), 9.37 (s, 1H); Anal. Calcd for $C_9H_6BrN$: C, 51.96; H, 2.91; N, 6.73; Br, 38.41. Found: C, 51.24; H, 2.79; N, 6.52; Br, 38.81.

EXAMPLE 57B 5-bromo-8-nitroisoquinoline

The diethyl ether solution from Example 57A was treated with potassium nitrate (10.1 g, 100 mmol). After stirring for one hour, The mixture was poured onto ice and neutralized with concentrated ammonium hydroxide (~300 ml). The crude product was collected by filtration, dried, and recrystalization from methanol to provide the title compound (8.83 g).

EXAMPLE 57C isoquinolin-8-amine

The product from Example 57B was treated with Pd/C under a hydrogen atmosphere to provide the title compound.

EXAMPLE 57D 2,2,2-trichloro-N-isoquinolin-8-ylacetamide

The product from Example 57C and trichloroacetylchloride were processed as described in Example 1A to provide the title compound.

EXAMPLE 57E

N-isoquinolin-8-yl-N'-[4-(trifluoromethyl)benzyl]urea

The title compound was prepared using 4-(trifluoromethyl)benzylamine, the product from Example 57D, DBU and the procedure described in Example 1B. MS (ESI+) m/z 346 (M+H)⁺; $^1$H NMR (DMSO-$d_6$) δ 9.58 (s, 1H), 9.10 (s, 1H), 8.49 (d, 1H), 8.12 (d, 1H), 7.81–7.54 (m, 7H), 7.20 (t, 1H), 4.47 (d, 2H); Anal. Calcd for $C_{18}H_{14}F_3N_3O*0.2\ H_2O$: C, 61.96, H 4.16, N 12.04. Found: C 62.06, H 4.23, N 11.91.

EXAMPLE 58

N-(4-bromobenzyl)-N'-isoquinolin-8-ylurea

The title compound was prepared using 4-bromobenzylamine, the product from Example 57D, DBU and the procedure described in Example 1B. MS (ESI+) m/z 356 (M+H)⁺; $^1$H NMR (DMSO-$d_6$) δ 9.52 (s, 1H), 9.15 (s, 1H), 8.49 (d, 1H), 8.11 (d, 1H), 7.77 (d, 1H), 7.67 (t, 1H), 7.55 (m, 3H) 7.32 (d, 2H), 7.25 (t, 1H), 4.34 (d, 2H); Anal. Calcd for $C_{17}H_{14}BrN_3O*0.25\ H_2O*0.16$ MeOH: C 56.34, H 4.17, N 11.49. Found C, 56.32, H 4.45, N 11.70.

EXAMPLE 60

N-(4-bromobenzyl)-N'-(3-chloroisoquinolin-5-yl)urea

EXAMPLE 60A

Isoquinoline-1,3(2H,4H)-dione 2-(Carboxymethyl)benzoic acid (10 g, 55.6 mmol) was dissolved in concentrated $NH_4OH$ (15 mL) and then was evaporated to dryness under reduced pressure. The process was repeated with additional NH₄OH (5 mL). The resulting residue was treated with 1,2-dichlorobenzene (20 mL) and heated with stirring at 200° C. without a condenser allowing the solvent to evaporate. The concentrated mixture was allowed to cool to room temperature, diluted with methanol (20 mL), and allowed to stand overnight. The precipitate was collected by filtration, washed with methanol, and dried under reduced pressure to provide the title compound as tan needles (6.6 g, 74%).

EXAMPLE 60B 1,3-dichloroisoquinoline

The product from Example 60A (6.5 g, 40.4 mmol) was treated with phenylphosphonic dichloride (11.5 mL, 81.1 mmol) and heated at 160° C. for 3 hours. The reaction was allowed to cool to room temperature and stand overnight. The resulting waxy orange material was dissolved in tetrahydrofuran (200 mL), treated with water (60 mL), and then concentrated under reduced to remove the tetrahydrofuran. The remaining aqueous material was neutralized with concentrated NH₄OH and extracted with ethyl acetate. The ethyl acetate phases were combined, washed with water, brine, dried over Na₂SO₄ and concentrated under reduced pressure to provide the title compound as yellow flakes (6.92 g, 74%).

EXAMPLE 60C 3-chloroisoquinoline

The product from Example 60B (6.73 g, 33.8 mmol) was suspended in glacial acetic acid (37 mL) and concentrated HCl (13 mL), treated with tin powder (12.1 g, 101.9 mmol), and heated at 55–60° C. for 3 hours with stirring. The mixture was allowed to cool to room temperature and the precipitated tin salts were removed by filtration through Celite. The filtrate was basified to pH 9 with concentrated NH₄OH and then extracted with ethyl acetate. The organic extracts were combined, washed with saturated NaHCO₃ solution, dried over Na₂SO₄, and concentrated under reduced pressure to provide the title compound as a gummy yellow residue (1.28 g, 23%).

EXAMPLE 60D 3-chloro-5-nitroisoquinoline

The product from Example 60C (1.28 g, 7.85 mmol) in concentrated H₂SO₄ (30 mL) at 0° C. was treated with a solution of KNO₃ (0.84 g, 8.32 mmol) in concentrated H₂SO₄ (5 mL) dropwise over 5 minutes. The mixture was stirred at 0° C. for 10 minutes, allowed to warm to room temperature, and stirred overnight. The mixture was poured onto 65 g of ice and the precipitated yellow solid was collected by filtration. The solid was slurried in water, collected by filtration, washed with water, and allowed to air-dry to provide the title compound as a pale yellow solid (0.45 g, 28%).

EXAMPLE 60E 3-chloroisoquinolin-5-amine

The product from Example 60D (0.45 g, 2.16 mmol) was suspended in glacial acetic acid (4 mL) and warmed to 60° C. while adding water (4 mL). The heated mixture was treated with powdered iron (0.33 g, 5.91 mmol) in three portions over about 2 minutes. The reaction mixture stirred at 60° C. for 2 hours, allowed to cool to room temperature and stir overnight. The mixture was basified with 25% aqueous NaOH, diluted with a little water, and the brown precipitate was collected by filtration and dried overnight at 50° C. in a vacuum oven. The filter cake was then broken up and extracted with boiling ethyl acetate. The extracts were combined, dried over Na₂SO₄, filtered, and the filtrate was concentrated under reduced pressure to provide the title compound as a gold-orange solid (200 mg, 52%).

EXAMPLE 60F

N-(4-bromobenzyl)-N'-(3-chloroisoquinolin-5-yl) urea

The product from Example 60E (250 mg, 1.4 mmol) and 1-bromo-4-(isocyanatomethyl)benzene (0.22 mL, 1.57 mmol) were heated in toluene (5 mL) at 80° C. for 3 hours. The mixture was allowed to cool to room temperature, filtered, the filter cake was washed with toluene, and air-dried to provide the title compound (335 mg, 61%). $^1$H NMR (300 MHz, DMSO-$d_6$) δ 9.18 (s, 1H), 8.81 (s, 1H), 8.32 (dd, J=7.8 Hz, 0.7 Hz, 1H), 8.09 (s, 1H), 7.80 (d, J=8.2 Hz, 1H), 7.53–7.65 (m, 3H), 7.32 (m, 2H), 7.05 (t, J=5.7 Hz, 1H), 4.35 (d, J=5.7 Hz, 2H); MS (EST⁺) m/z 391/393 (M+H⁺, $^{35}$Cl/$^{37}$Cl).

EXAMPLE 61

4-cyanobenzyl isoquinolin-5-ylcarbamate

EXAMPLE 61A 5-isocyanatoisoquinoline

Phosgene (20 ml, 20% in toluene from Fluka) in CH₂Cl₂ (300 mL) at 0° C. was treated with DMAP (10 g) in CH₂Cl₂ (100 mL) slowly. After complete addition, the mixture was treated with 5-aminoisoquinoline (5 g) in CH₂Cl₂ (100 mL) dropwise. The mixture was allowed to warm to room temperature and then stirred overnight. The solvent was removed under reduced pressure. The solid residue was extracted with diethyl ether (400 mL). The diethyl ether was filtered to provide the title compound in diethyl ether as a pale yellow solution. The diethyl ether solution was used in subsequent reactions without further purification.

EXAMPLE 61B 4-cyanobenzyl isoquinolin-5-ylcarbamate

4-Cyanobenzyl alcohol (150 mg, 1.13 mmol) diethyl ether (10 mL) was treated with the product from Example 61A as an ethereal solution. The mixture was stirred for 2 hours, filtered, and the filter cake was washed with diethyl ether to provide the title compound as an off-white solid (150 mg, 44%). $^1$H HMR (300 MHz, DMSO-$d_6$) δ 9.95 (s, 1H), 9.32 (d, J=1.0 Hz, 1H), 8.52 (d, J=6.1 Hz, 1H), 7.88–7.99 (m, 5H), 7.65–7.70 (m, 3H), 5.31 (s, 2H); MS (ESI⁺) m/z 304 (M+H)⁺.

EXAMPLE 62

N-[(4-cyanophenyl)methyl]-N'-isoquinolin-5-ylurea

N, N-bis(tert-butoxycarbonyl)-4-cyanobenzyl amine (0.75 g, 2.25 mmol, prepared according to Synth. Comm. (1998) 28, 4419) in CH₂Cl₂ (15 mL) was treated with trifluoroacetic acid (8 mL), and the resulting mixture was stirred at room temperature for 3 hours. The mixture was concentrated under reduced pressure and then azeotroped with diethyl ether. The residue was taken up in diethyl ether (10 mL) and treated with N,N-diisopropylethylamine (5 mL) and the product from Example 61A. After stirring for 1 hour, the mixture was filtered and the filter was purified by chromatography (95:5 $CH_2Cl_2$—MeOH) to provide the title compound as a white solid (65 mg). The corresponding hydrochloride salt was prepared using methanolic HCl. $^1$H NMR (300 MHz, DMSO-$d_6$) δ9.75 (s, 1H), 9.62 (s, 1H), 8.69 (s, 2H), 8.58 (dd, J=7.8 Hz, 1.0 Hz, 1H), 8.07 (d, J=7.4 Hz, 1H), 7.90 (d, J=8.1 Hz, 1H), 7.81–7.85 (m, 2H), 7.74 (t, J=6.1 Hz, 1H), 7.54–7.57 (m, 2H), 4.48 (d, J=6.1 Hz, 2H); MS (ESI$^+$) m/z 303 (M+H)$^+$.

EXAMPLE 63

N-[(4-bromophenyl)methyl]-N'-(3-methylisoquinolin-5-yl)urea

EXAMPLE 63A 3-methylisoquinolin-5-amine

3-Methylisoquinoline was processed as described in Examples 60D and 60E to provide the title compound.

EXAMPLE 63B

N-[(4-bromophenyl)methyl]-N'-(3-methylisoquinolin-5-yl)urea

The product from Example 63A (500 mg, 3.1 mmol) in toluene (10 mL) was treated with 1-bromo-4-(isocyanatomethyl)benzene (0.5 mL, 3.57 mmol) with stirring and then the mixture was heated at 80° C. overnight. The mixture was allowed to cool to room temperature, filtered, the filter cake was washed with toluene, and allowed to air-dry to provide the title compound. The corresponding hydrochloride salt was prepared using methanolic HCl to afford a tan solid (919 mg, 73%). $^1$H NMR (300 MHz, DMSO-$d_6$) δ 9.70 (s, 1H), 9.54 (s, 1H), 8.63 (s, 1H), 8.57 (dd, J=7.8 Hz, 1.0 Hz, 1H), 8.02 (d, J=8.2 Hz, 1H), 7.78–7.83 (m, 1H), 7.67–7.71 (m, 1H), 7.52–7.57 (m, 2H), 7.30–7.35 (m, 2H), 4.36 (d, J=5.7 Hz, 2H), 2.78 (s, 3H); MS (ESI$^+$) m/z 370/372 (M+H, $^{79}$Br/$^{81}$Br).

EXAMPLE 64

N-[(4-bromophenyl)methyl]-N'-(1-chloroisoquinolin-5-yl)urea

EXAMPLE 64A 1-chloroisoquinolin-5-amine

1-Chloroisoquinoline was processed as described in Examples 60D and 60E to provide the title compound.

EXAMPLE 64B

N-[(4-bromophenyl)methyl]-N'-(1-chloroisoquinolin-5-yl)urea

The product from Example 64A (520 mg, 2.91 mmol) in toluene (8 mL) was treated with 1-bromo-4-(isocyanatomethyl)benzene (0.41 mL, 2.93 mmol) with stirring and then the mixture was heated at 90° C. for 2 hours. The mixture was allowed to cool to room temperature, filtered, the filter cake washed with toluene, and air-dried to provide the title compound as an off-white solid (717 mg, 63%). $^1$H NMR (300 MHz, DMSO-$d_6$) δ 8.89 (s, 1H), 8.34–8.37 (m, 2H), 8.00 (dd, J=6.1 Hz, 0.7 Hz, 1H), 7.92–7.95 (m, 1H), 7.73 (t, J=8.1, 1H, 7.53–7.56 (m, 2H), 7.30–7.33 (m, 2H), 7.12 (t, J=5.8 Hz, 1H), 4.35 (d, J=5.8 Hz, 2H); MS (ESI$^+$) m/z 390/392 (M+H$^+$, $^{35}$Cl/$^{37}$Cl).

EXAMPLE 65

N-[(4-bromophenyl)methyl]-N'-(1-methylisoquinolin-5-yl)urea

EXAMPLE 65A 1-methylisoquinolin-5-amine

1-Methylisoquinoline was processed as described in Examples 60D and 60E to provide the title compound.

EXAMPLE 65B

N-[(4-bromophenyl)methyl]-N'-(1-methylisoquinolin-5-yl)urea

The product from Example 65A (480 mg, 3.04 mmol) in toluene (9 mL) was treated with 1-bromo-4-(isocyanatomethyl)benzene (0.43, 3.07 mmol) with stirring. After heating the mixture at 90° C. for 1 hour, the mixture was allowed to cool to room temperature, filtered, and the filter cake washed with toluene to provide the title compound. The corresponding di-hydrochloride salt was prepared using methanolic HCl (680 mg, 50%). $^1$H NMR (300 MHz, DMSO-$d_6$) δ 8.74 (s, 1H), 8.38 (d, J=6.1 Hz, 1H), 8.25 (d, J=7.8 Hz, 1H), 7.78–7.85 (m, 2H), 7.53–7.61 (m, 3H), 7.32 (d, J=8.5 Hz, 2H), 7.11 (t, J=6.1 Hz, 1H), 4.34 (d, J=6.1 Hz, 2H), 2.88 (s, 3H); MS (ESI$^+$) m/z 370/372 (M+H$^+$, $^{79}$Br/$^{81}$Br).

EXAMPLE 66

N-isoquinolin-5-yl-N'-[(4-morpholin-4-ylphenyl)methyl]urea

EXAMPLE 66A 4-morpholin-4-ylbenzonitrile

4-Fluorobenzonitrile (1 g, 8.26 mmol) and morpholine (2.2 mL, 25.2 mmol) were combined in DMSO (25 mL) and heated at 100° C. for 2.5 hours. The mixture was allowed to cool to room temperature, poured into water, and extracted with diethyl ether. The organic extracts were combined, washed with water and brine, dried over $Na_2SO_4$, and concentrated under reduced pressure to provide the title compound as a white solid (1.24 g, 80%).

EXAMPLE 66B (4-morpholin-4-ylphenyl)methylamine

The product from Example 66A (1.24 g, 6.6 mmol) in THF (25 mL) was treated with LiAlH$_4$ (2.5 g, 65.9 mmol) at 0° C. The mixture was allowed to warm to room temperature and then refluxed for 1 hour. The mixture was allowed to cool to room temperature and then treated with 1N NaOH carefully followed by water. The mixture was concentrated under reduced pressure and the resulting aqueous mixture was extracted with diethyl ether. The organic extracts were combined, washed with saturated NaHCO$_3$ solution, dried over $Na_2SO_4$, filtered, and the filtrate concentrated under reduced pressure to provide the title compound as a yellow oil (286 mg, 23%).

EXAMPLE 66C

N-isoquinolin-5-yl-N'-[(4-morpholin-4-ylphenyl) methyl]urea

The product from Example 66B (285 mg, 1.48 mmol) in diethyl ether (10 mL) was treated with the product from Example 61A. The mixture was filtered and the filter cake purified by chromatography (95:5 $CH_2Cl_2$—MeOH, eluant) to provide that title compound as a white solid. The corresponding di-hydrochloride salt was prepared using methanolic HCl to afford a yellow solid (505 mg, 78%). $^1$H NMR (300 MHz, DMSO-$d_6$) δ 9.26 (s, 1H), 8.67 (s, 1H), 8.52–8.55 (m, 1H), 8.32 (dd, J=7.8 Hz, 1.1 Hz, 1H), 7.92 (d, J=6.1 Hz, 1H0, 7.73 (d, J=8.2 Hz, 1H), 7.60 (m, 1H), 7.23 (d, J=8.8 Hz, 1H), 6.92–6.96 (m, 3H), 4.26 (d, 5.4 Hz, 2H), 3.72–3.75 (m, 4H), 3.06–3.12 (m, 4H); MS (ESI$^+$) m/z 363 (M+H)$^+$.

EXAMPLE 67

N-{[4-(2,6-dimethylmorpholin-4-yl)phenyl]methyl}-N'-Isoquinolin-5-ylurea

EXAMPLE 67A

[4-(2,6-dimethylmorpholin-4-yl)phenyl] methylamine

4-Fluorobenzonitrile and 2,6-dimethylmorpholine were processed as described in Examples 66A and 66B to provide the title compound.

EXAMPLE 67B

N-{[4-(2,6-dimethylmorpholin-4-yl)phenyl]methyl}-N'-isoquinolin-5-ylurea

The product from Example 67A and the product from Example 61A were processed as described in Example 66C to provide a waxy material which was purified by chromatography (95:5 $CH_2Cl_2$—MeOH, eluant) to provide the title compound as a white solid. The corresponding di-hydrochloride salt was prepared using methanolic HCl. $^1$H HMR (300 MHz, DMSO-$d_6$) δ 9.26 (s, 1H), 8.67 (s, 1H), 8.53 (d, J=6.1 Hz, 1H), 8.31 (dd, J=7.6 Hz, 1.1 Hz, 1H), 7.92 (d, J=6.1 Hz, 1H), 7.73 (d, J=8.1 Hz, 1H), 7.57–7.62 (m, 1H), 7.22 (d, J=8.8 Hz, 2H), 6.92–6.95 (m, 3H), 4.26 (d, J=5.7 Hz, 2H), 3.68 (m, 2H), 3.54–3.57 (m, 2H), 2.21 (m, 2H), 1.16 (s, 3H), 1.14 (s, 3H); MS (ESI$^+$) m/z 391 (M+H).

EXAMPLE 68

N-isoquinolin-5-yl-N'-[(4-thiomorpholin-4-ylphenyl) methyl]urea

EXAMPLE 68A (4-thiomorpholin-4-ylphenyl)methylamine

4-Fluorobenzonitrile and thiomorpholine were processed as described in Examples 66A and 66B to provide the title compound.

EXAMPLE 68B

N-isoquinolin-5-yl-N'-[(4-thiomorpholin-4-ylphenyl) methyl]urea

The product from Example 68A and the product from Example 61A were processed as described in Example 66C to provide the title compound. The free base was treated with methanolic HCl to form the corresponding di-hydrochloride salt. $^1$H NMR (300 MHz, DMSO-$d_6$) δ 9.26 (s, 1H), 8.67 (s, 1H), 8.53 (d, J=6.1 Hz, 1H), 8.32 (dd, J=7.8 Hz, 1.1 Hz, 1H), 7.92 (d, J=6.1 Hz, 1H), 7.73 (d, J=8.2 Hz, 1H), 7.60 (m, 1H), 7.20–7.23 (m, 2H), 6.90–6.96 (m, 3H), 4.25 (d, J=5.8 Hz, 2H), 3.45–3.51 (m, 4H), 2.64–2.67 (m, 4H); MS (ESI$^+$) m/z 379 (M+H)$^+$.

EXAMPLE 69

4-(3,4-dichlorophenyl)-N-isoquinolin-5-ylpiperazine-1-carboxamide 1-(3,4-Dichlorophenyl)piperazine (1280 mg, 5.55 mmol) in diethyl ether (30 mL) was treated with the product from Example 61A (~40 mL). The mixture was filtered, the filter cake washed with diethyl ether, and dried under reduced pressure to provide the title compound as a white solid (1.78 g, 80%). $^1$H NMR (300 MHz, DMSO-$d_6$) δ 9.29 (d, J=1.0 Hz, 1H), 8.84 (s, 1H), 8.49 (d, J=5.8 Hz, 1H), 7.92 (d, J=7.8 Hz, 1H), 7.78 (m, 1H), 7.61–7.71 (m, 2H), 7.44 (d, J=8.8 Hz, 1H), 7.22 (d, J=3.1 Hz, 1H), 7.01 (dd, J=9.1, 2.7 Hz, 1H), 3.68 (M, 4H), 3.30 (m, 4H); MS (EST$^+$) m/z 401/403 (M+H)$^+$, $^{35}Cl/^{37}Cl$).

EXAMPLE 70

2-isoquinolin-5-yl-N-[4-(trifluoromethyl)benzyl] acetamide

EXAMPLE 70A ethyl isoquinolin-5-yl(oxo)acetate

The product from Example 57A (11.80 g, 56.6 mmol) in THF (200 mL) at −78° C. was treated with n-butyllithium (30 mL, 75.0 mmol, 2.5M in hexanes) dropwise. After 30 minutes, the mixture was treated with diethyl oxalate (25.0 mL, 184 mmol). After 20 minutes, the solution was allowed to warm to room temperature and was treated with saturated NH$_4$Cl (150 mL). The mixture was concentrated under reduced pressure. The residue was treated with dichloromethane (100 mL) filtered, and the filtrate concentrated under reduced pressure. The residue was purified by column chromatography (20% ethyl acetate/hexanes) to provide the title compound as light brown oil (4.57 g, 35%). MS (ESI+) m/z 248 (100), 230 (M+H)$^+$, (ESI−) m/z 200 (M−Et$^-$; $^1$H NMR (DMSO-$d_6$, 300 MHz) rotomers δ 1.26 (t, J 7.1, 0.6H), 1.37 (t, J 7.1, 2.4H), 4.21 (q, J 7.1, 0.4H), 4.47 (q, J 7.1, 1.6H), 7.89 (t, J 7.5, 1H), 8.41 (dd, J 1.0, 7.5, 1H), 8.57 (d, J 8.1, 1H), 8.64 (d, J 5.7, 1H), 8.73 (d, J 6.3, 1H), 9.50 (s, 1H).

EXAMPLE 70B ethyl hydroxy(isoquinolin-5-yl)acetate

The product of Example 70A (1.11 g, 4.83 mmol) in absolute ethanol (20 mL) was added to 10% Pd/C (115.5 mg) under an argon atmosphere. The reaction mixture was stirred under H$_2$ (50 psi) for 5 hours at which time an additional 105.9 mg of catalyst was added as a suspension in ethanol. After 3 additional hours, the reaction mixture was filtered though a nylon membrane and the filtrate concentrated under reduced pressure to provide the title compound as dark brown oil (1.02 g, 91%). MS (ESI+) m/z 232 (M+H)$^+$, (ESI−) m/z 202 (M−Et)$^-$; $^1$H NMR (DMSO-$d_6$, 300 MHz) δ 1.05 (t, J 7.1, 3H), 4.07 (m, 2H), 5.77 (d, J 4.7, 1H), 6.36 (d, J 4.7, 1H), 7.68 (dd, J 7.3, 8.1, 1H), 7.85 (d, J 7.0, 1H), 8.09 (t, J 7.5, 2H), 8.53 (d, J 6.2, 1H), 9.33 (s, 1H).

EXAMPLE 70C ethyl (acetyloxy)(isoquinolin-5-yl)acetate

The product of Example 70B (1.0202 g, 4.41 mmol) in pyridine (15 mL) was treated with acetyl chloride (0.35 mL, 4.92 mmol) dropwise. The solution was stirred at room temperature for 4 hours and concentrated under reduced pressure. The residue was purified by column chromatography (2% methanol/$CH_2CH_2$) to provide the title compound as yellow oil (0.8100 g, 67%). MS (ESI+) m/z 274 (M+H)$^+$; $^1$H NMR (DMSO-$d_6$, 300 MHz) δ 1.07 (t, J 7.1, 3H), 2.17 (s, 3H), 4.13 (m, 2H), 6.62 (s, 1H), 7.74 (m, 1H), 7.94 (d, J 7.1, 1H), 8.03 (d, J 6.1, 1H), 8.22 (d, J 7.6, 1H), 8.60 (d, J 5.7, 1H), 9.39 (s, 1H).

EXAMPLE 70D ethyl isoquinolin-5-ylacetate

The product of Example 70C (1.43 g, 5.23 mmol) in absolute ethanol (200 mL) was treated with dry 10% Pd/C (0.122 g) and triethylamine (10.4 mL). The reaction mixture was stirred at 60° C. for 6 hours under $H_2$ (60 psi), filtered and the filtrate concentrated under reduced pressure. The residue was purified by column chromatography (5% methanol/$CH_2Cl_2$) to provide the title compound as light brown oil (0.93 g, 67%). MS (ESI+) m/z 216 (M+H)$^+$, (ESI–) m/z 214 (M–H)$^-$; $^1$H NMR (DMSO-$d_6$, 300 MHz) δ 1.17 (t, J 7.1, 3H), 4.09 (q, J 7.1, 2H), 4.17 (s, 2H), 7.64 (m, 1H), 7.72 (d, J 6.2, 1H), 7.81 (d, J 5.7, 1H), 8.07 (d, J 7.9, 1H), 8.54 (d, J 6.1, 1H), 9.33 (s, 1H).

EXAMPLE 70E 2-isoquinolin-5-yl-N-[4-(trifluoromethyl)benzyl]acetamide

The product from Example 70D (0.207 g, 0.96 mmol) in dichloromethane (10 mL) was treated with trimethylaluminum (1 mL, 2.0 mmol, 2M in toluene) dropwise. After 30 minutes, the mixture was teated with 4-(trifluoromethyl)benzylamine (0.350 g, 2.0 mmol) in dichloromethane (2 mL) and then refluxed for 16 hours. The reaction mixture was allowed to cool to room temperature, treated with 1M HCl (3 mL), basified to between pH 9 and 10 with concentrated $NH_4OH$, treated with water and $CH_2Cl_2$ and the phases separated. The organic layer was washed with water (1×10 mL), brine (1×10 mL), dried ($MgSO_4$), and the filtrate was concentrated under reduced pressure. The residue was purified by column chromatography (5% methanol/$CH_2Cl_2$) to provide a yellow residue which was triturated with diethyl ether to provide the title compound as a white solid (0.122 g, 37%). MS (ESI+) m/z 345 (M+H)$^+$; MS (ESI–) m/z 343 (M–H)$^-$; $^1$H NMR (DMSO, 300 MHz) δ 4.00 (s, 2H), 4.37 (d, J 5.7, 2H), 7.46 (d, J 7.8, 2H), 7.67 (m, 4H), 7.93 (d, J 5.4, 1H), 8.03 (d, J 7.8, 1H), 8.52 (d, J 5.8, 1H), 8.80 (t, J 5.7, 1H), 9.31 (s, 1H); Anal. Calcd for $C_{19}H_{15}F_3N_2O$: C, 66.28; H, 4.39; N, 8.14. Found: C, 66.16; H, 4.27; N, 7.96.

EXAMPLE 71 methyl 5-({[(4-bromobenzyl)amino]carbonyl}amino)isoquinoline-3-carboxylate

EXAMPLE 71A methyl 5-nitroisoquinoline-3-carboxylate

Methyl isoquinoline-3-carboxylate (9.58 g, 51.2 mmol) in concentrated $H_2SO_4$ (100 mL) at 0° C. was treated with sodium nitrate (4.79 g, 56.4 mmol) in small portions such that the temperature was maintained below 5° C. Ten minutes after addition was complete, the reaction mixture was allowed to warm to room temperature and stirred for 2 hours. The mixture was poured over ice and adjusted to pH between 7 and 8 and filtered to afford the title compound as a bright yellow solid (11.44 g, 96%). MS (ESI+) m/z 233 (M+H)$^+$; $^1$H NMR (DMSO, 300 MHz) δ 3.97 (s, 3H), 8.06 (t, J 8.2, 1H), 8.72 (dt, J 1.0, 8.2, 1H), 8.78 (dd, J 1.0, 7.8, 1H), 9.11 (s, 1H), 9.65 (s, 1H).

EXAMPLE 71B methyl 5-aminoisoquinoline-3-carboxylate

The product of Example 71A (10.33 g, 44.5 mmol) in acetic acid/water (3/1) (320 mL) was treated with iron powder (5.06 g, 90.7 mmol). After stirring for 16 hours at room temperature, the reaction mixture was filtered the filtrate concentrated under reduced pressure to approximately half the original volume. The mixture was then extracted with dichloromethane (3×200 mL). The organic fractions were combined, dried ($MgSO_4$), and the filtrate concentrated under reduced pressure to afford crude material. A precipitate formed in the aqueous phase after sitting for several hours. This was filtered to afford additional crude material. The crude material was purfidied by column chromatography (2% methanol/$CH_2Cl_2$) to provide the title compound. MS (ESI+) m/z 203 (M+H)$^+$; MS (ESI–) m/z 201 (M–H)$^-$; $^1$H NMR (DMSO-$d_6$, 300 MHz) δ 3.92 (s, 3H), 6.34 (s, 2H), 6.96 (dd, J 1.0, 7.8, 1H), 7.31 (d, J 8.1, 1H), 7.51 (t, J 7.9, 1H), 8.82 (s, 1H), 9.15 (s, 1H); Anal. Calcd for $C_{11}H_{10}N_2O_2$: C, 65.34; H, 4.99; N, 13.85. Found: C, 65.03; H, 4.95; N, 13.65.

EXAMPLE 71C methyl 5-({[(4-bromobenzyl)amino]carbonyl}amino)isoquinoline-3-carboxylate The product of Example 71B (0.156 g, 0.77 mmol) in THF:toluene (10 mL, 1:1) was treated with a solution of 1-bromo-4-(isocyanatomethyl)benzene (0.201 g, 0.95 mmol) in THF (1.0 mL). After stirring for 16 hours at room temperature, the reaction mixture was concentrated under reduced pressure and the residue was triturated with diethyl ether to provide the title compound as a tan solid (0.272 g, 85%). MS (ESI+) m/z 4.15 (M+H)$^+$; MS (ESI–) m/z 413 (M–H)$^-$; $^1$H NMR (DMSO-$d_6$, 300 MHz) δ 3.95 (s, 3H), 4.36 (d, J 5.6, 2H), 7.23 (t, J 5.6, 1H), 7.33 (m, 2H), 7.56 (m, 2H), 7.76 (t, J 7.8, 1H), 7.85 (d, J 8.3, 1H), 8.41 (dd, J 1.5, 7.8, 1H), 8.82 (s, 1H), 9.06 (s, 1H), 9.35 (s, 1H); Anal. Calcd for $Cl9H_{16}BrN_3O_3$: C, 55.09; H, 3.89; N, 10.14. Found: C, 55.06; H, 3.56; N, 9.84.

EXAMPLE 72 methyl 5-({[(2,4-dichlorobenzyl)amino]carbonyl}amino)Isoquinoline-3-carboxylate

The product of Example 71B (0.156 g, 0.77 mmol) in THF:toluene (10 mL, 1:1) was treated with a solution of 2,4-dichloro-1-(isocyanatomethyl)benzene (0.195 g, 0.97 mmol) in THF (1.0 mL). After stirring for 16 hours at room temperature, the reaction mixture was concentrated under reduced pressure and the residue was triturated with diethyl ether to provide the title compound as a tan solid (0.226 g, 73%). MS (ESI+) m/z 404 (M+H)$^+$; MS (ESI–) m/z 402 (M–H)$^-$; $^1$H NMR (DMSO-$d_6$, 300 MHz) δ 3.96 (s, 3H), 4.44 (d, J 6.0, 2H), 7.29 (m, 1H), 7.48 (m, 1H), 7.65 (d, J 1.7, 1H), 7.76 (t, J 7.8, 1H), 7.86 (d, J 7.8, 1H), 8.41 (dd, J 1.0, 7.8, 1H), 8.84 (s, 1H), 9.15 (s, 1H), 9.35 (s, 1H); Anal. Calcd for $C_{19}H_{15}Cl_2N_3O_3$; C, 56.45; H, 3.74; N, 10.39. Found: C, 56.08; H, 3.67; N, 10.03.

EXAMPLE 73

N-(8-bromoisoquinolin-5-yl)-N'-(2,4-dichlorobenzyl)urea

EXAMPLE 73A 8-bromoisoquinolin-5-amine

5-Aminoisoquinoline (5.50 g, 38.1 mmol) and aluminium trichloride (15.1 g, 113 mmol) were combined and heated at 80° C. in a 3-necked flask equipped with a dropping funnel, stirrer bar, needle and sintered glass tube. Bromine (3.04 g, 19.05 mmol) was dripped onto the sintered glass funnel and the vapour diffused onto the complex over a period of 2 hours. Heating was continued for 2 hours. The suspension was added portionwise to crushed ice and the solution basified with concentrated NaOH solution. The aqueous layer was extracted with ethyl acetate (4×100 mL) and the layers were separated. The organic layers were combined, dried ($Na_2SO_4$), filtered and the filtrate was concentrated to give a grey solid. The grey solid was subjected to column chromatography (hexanes:ethyl acetate, 3:1) to provide the title compound (2.96 g, 35%). MS (ESI+) m/z 225 (M+H)$^+$; MS (ESI−) m/z 223 (M−H)$^-$; $^1$H NMR (CDCl$_3$, 300 MHz) δ 4.22 (br s, 2H), 6.83 (d, J 8.1, 1H), 7.25 (s, 1H), 7.54 (d, J 5.8, 1H), 7.61 (d, J 8.1, 1H), 8.59 (d, J 5.8, 1H), 9.56 (s, 1H).

EXAMPLE 73B

N-(8-bromoisoquinolin-5-yl)-N'-(2,4-dichlorobenzyl)urea

The product from Example 73A (120 mg, 0.52 mmol) in THF:toluene (1.4, 5 mL) was treated with a solution of 2,4-dichloro-1-(isocyanatomethyl)benzene (108 mg, 0.52 mmol) in THF (0.5 mL). After stirring for 16 hours at room temperature, the mixture was filtered and the filter cake dried under reduced pressure to provide the title compound as a white solid (178 mg, 78%). The hydrochloride salt was obtained by dissolving the product in hot THF and adding HCl in diethyl ether (2M). The yellow precipitate was collected by filtration and dried under reduced pressure. MS (ESI+) m/z 426 (M+H)$^+$; MS (ESI−) m/z 424 (M−H)$^-$; $^1$H NMR (DMSO-d$_6$, 300 MHz) δ 4.42 (d, 5.8, 2H), 7.22 (t, J 5.8, 1H), 7.65 (m, 1H), 7.91 (d, J 8.5, 1H), 8.02 (d, J 6.1, 1H), 8.22 (d, J 8.5, 1H), 8.69 (d, J 5.8, 1H), 9.01 (s, 1H), 9.44 (s, 1H); Anal. Calcd for $C_{17}H_{12}BrCl_2N_3O$ HCl 0.25 EtOH: C, 44.41; H, 3.14; N, 8.88. Found: C, 44.80; H, 2.76; N, 8.84.

EXAMPLE 74

N-(8-bromoisoquinolin-5-yl)-N'-(4-fluorobenzyl)urea

The title compound was prepared using 1-fluoro-4-(isocyanatomethyl)benzene, the product of Example 73A and the procedure described in Example 73B (white solid, 108 mg, 65%) MS (ESI+) m/z 376 (M+H)$^+$; MS (ESI−) m/z 374 (M−H)$^-$; $^1$H NMR (DMSO-d$_6$, 300 MHz) δ 4.35 (d, 5.8, 2H), 7.12 (m, 1H), 7.18 (m, 2H), 7.40 (m, 1H), 7.91 (d, J 8.5, 1H), 7.99 (d, J 6.1, 1H), 8.24 (d, J 8.5, 1H), 8.69 (d, J 5.8, 1H), 8.88 (s, 1H), 9.44 (s, 1H); Anal. Calcd for $C_{17}H_{13}BrFN_3O$: C, 54.56; H, 3.50; N, 11.23. Found: C, 54.61; H, 3.35; N, 11.14.

EXAMPLE 75

N-(8-bromoisoquinolin-5-yl)-N'-(3-fluorobenzyl)urea

The title compound was prepared using 1-fluoro-3-(isocyanatomethyl)benzene, the product of Example 73A and the procedure described in Example 73 (white solid, 108 mg, 65%). MS (ESI+) m/z 376 (M+H)$^+$; MS (ESI−) m/z 374 (M−H)$^-$; $^1$H NMR (DMSO-d$_6$, 300 MHz) δ 4.39 (d, 5.8, 2H), 7.09 (m, 1H), 7.17 (m, 2H), 7.40 (m, 1H), 7.91 (d, J 8.5, 1H), 8.01 (d, J 6.1, 1H), 8.23 (d, J 8.5, 1H), 8.69 (d, J 5.8, 1H), 8.93 (s, 1H), 9.44 (s, 1H); Anal. Calcd for $C_{17}H_{13}BrFN_3O$: C, 54.56; H, 3.50; N, 11.23. Found: C, 54.64; H, 3.33; N, 11.19.

EXAMPLE 76

N-[1-(4-chlorophenyl)-1-methylethyl]-N'-isoquinolin-5-ylurea

EXAMPLE 76A 2-(4-chlorophenyl)-2-methylpropanoyl chloride 2-(4-Chlorophenyl)-2-methylpropanoic acid (3.85 g, 19.4 mmol) in toluene (5 mL) was treated with thionyl chloride (5.00 g, 3.1 mL) and heated at 80° C. for 2 hours. The cooled solution was concentrated under reduced pressure to provide a yellow oil containing a crystalline residue. The mixture was dissolved in hexane, filtered and the filtrate concentrated to provide the compound as a pale yellow oil (4.10 g, 98%).

EXAMPLE 76B 1-chloro-4-(1-isocyanato-1-methylethyl)benzene

The product of Example 76A (4.00 g, 19.4 mmol) in acetone (9 mL) at 0° C. was treated with a solution of sodium azide (1.27 g) in water (9 mL) dropwise over 15 minutes. After stirring for 30 minutes at 0° C., the mixture was extracted with toluene (20 mL). The organic extract was dried with MgSO$_4$, filtered, and the filtrate heated at reflux for 1 hour. The mixture was allowed to cool to room temperature and was concentrated under reduced pressure to provide the title compound as a pale yellow oil (3.45 g, 96%).

EXAMPLE 76C

N-[1-(4-chlorophenyl)-1-methylethyl]-N'-isoquinolin-5-ylurea

The title compound was prepared using 5-aminoisoquinoline, the product of Example 76B and the procedure described in Example 73B except that THF was used as solvent. The product was recrystallized from ethyl acetate to provide the title compound as a white solid (840 mg, 34%). MS (ESI+) m/z 355 (M+H)$^+$; MS (ESI−) m/z 353 (M−H)$^-$; $^1$H NMR (DMSO-d$_6$, 300 MHz) δ 1.63 (s, 6H), 7.23 (s, 1H), 7.37 (d, J 8.8, 2H), 7.47 (d, J 8.8, 2H), 7.73 (t, J 9.2, 1H), 7.93 (d, J 8.1, 1H), 8.25 (d, J 6.4, 1H), 8.39 (d, J 8.1, 1H), 8.67 (d, J 6.4, 1H), 8.87 (s, 1H), 9.58 (s, 1H); Anal. Calcd for $C_{19}H_{18}ClN_3O$ HCl 0.25 EtOH: C, 60.40; H, 5.33; N, 10.54. Found: C, 60.82; H, 5.23; N, 1045.

EXAMPLE 77

N-(4-bromobenzyl)-N'-{6-[2,2,2-trifluoro-1-hydroxy-1-(trifluoromethyl)ethyl]isoquinolin-5-yl}urea

EXAMPLE 77A 2-(5-aminoisoquinolin-6-yl)-1,1,1,3,3,3-hexafluoropropan-2-ol

5-Aminoisoquinoline (288 mg, 2.00 mmol) and p-toluenesulfonic acid (5 mg) were combined and treated with hexafluoroacetone hexahydrate (0.29 mL, 462 mg, 2.10 mmol). The mixture was stirred in a sealed pressure tube and heated to 150° C. for 18 hours. The reaction was allowed to cool to room temperature and partitioned between $CH_2Cl_2$ (20 mL) and water (10 mL). The organic layer was passed thru $Na_2SO_4$ and then filtered through activated charcoal. The charcoal was washed with methanol (3×10 mL) and the filtrate and washings were collected and concentrated under reduced pressure to provide the title compound (130 mg, 30%) as a yellow solid. MS (ESI+) m/z 311 (M+H)$^+$; MS (ESI–) m/z 309 (M–H)$^-$; $^1$H NMR (DMSO, 300 MHz) δ 6.64 (br s, 2H), 7.30 (d, J 8.7, 1H), 7.40 (d, J 8.7, 1H), 8.09 (d, J 6.1, 1H), 8.49 (d, J 6.1, 1H), 9.14 (s, 1H); $^{13}$C NMR (DMSO, 100 MHz) δ 107.02, 110.60, 113.95 (1), 115.46 (1), 122.03, 124.92, 124.92, 125.94, 126.98 (1), 128.17, 142.43 (1), 144.82, 151.85 (1).

EXAMPLE 77B

N-(4-bromobenzyl)-N'-{6-[2,2,2-trifluoro-1-hydroxy-1-(trifluoromethyl)ethyl]Isoquinolin-5-yl}urea The title compound was prepared using 1-bromo-4-(isocyanatomethyl)benzene, the product of Example 77A and the procedure described in Example 73B except that THF was used as solvent (white solid, 840 mg, 34%). MS (ESI+) m/z 376 (M+H)$^+$; MS (ESI–) m/z 374 (M–H)$^-$; $^1$H NMR (DMSO-d$_6$, 300 MHz) δ 4.35 (d, 5.8, 2H), 7.12 (m, 1H), 7.18 (m, 2H), 7.40 (m, 1H), 7.91 (d, J 8.5, 1H), 7.99 (d, J 6.1, 1H), 8.24 (d, J 8.5, 1H), 8.69 (d, J 5.8, 1H), 8.88 (s, 1H), 9.44 (s, 1H); Anal. Calcd for $C_{20}H_{14}BrF_6N_3O_2$: C, 46.00; H, 3.50; N, 11.23. Found: C, 54.61; H, 3.35; N, 11.14.

EXAMPLE 78

N-(4-bromobenzyl)-N'-1H-indol-4-ylurea 4-aminoindole (0.13 g, 1 mmol) in THF (3 mL) was treated with 1-bromo-4-(isocyanatomethyl)benzene (0.23 g, 1.1 mmol) for 3 hours at ambient temperature. Hexane was added to the reaction mixture to precipitate 0.26 g of the title compound as a tan solid. mp 198° C.; $^1$H NMR (300 MHz, DMSO-d$_6$) δ 4.30 (d, 2H), 6.51 (t, 1H), 6.89 (t, 1H), 6.95 (d, 2H), 7.29 (t, 1H), 7.31 (d, 2H), 7.55 (d, 2H), 7.62 (dd, 1H), 8.3 (s, 1H), 11.04 (s, 1H); MS (DCI+) m/z 346 (M+H); Anal. Calcd. For $C_{16}H_{14}N_3BrO$: C, 55.83; H, 4.10; N, 12.21. Found: C, 55.71, H, 4.12; N, 12.01.

EXAMPLE 79

N-(3,4-dichlorobenzyl)-N'-1H-indol-4-ylurea

4-Aminoindole (0.13 g, 1 mmol) in THF (3 mL) was treated with 1,2-dichloro-4-(isocyanatomethyl)benzene (0.22 g, 1.1 mmol) for 3 h at ambient temperature. Hexane was added to the reaction mixture to precipitate 0.25 g of the title compound as a tan solid. mp 201° C.; $^1$H NMR (300 MHz, DMSO-d$_6$) δ 4.23 (d, 2H), 6.36 (s, 1H), 6.54 (t, 1H), 7.0 (dd, 1H), 7.25 (m, 2H), 7.30 (d, 2H), 7.45 (d, 1H), 7.6 (m, 2H), 8.31 (s, 1H), 10.87 (s, 1H) MS (DCI+) m/z 336 (M+H); Anal. Calcd. For $C_{16}H_{15}N_3Cl_2O$: C, 57.50; H, 3.92; N, 12.57. Found: C, 56.94, H, 3.68; N, 11.97.

EXAMPLE 80

N-1H-indol-4-yl-N'-[4-(trifluoromethyl)benzyl]urea

EXAMPLE 80A 4-isocyanato-1H-indole

4-Aminoindole (0.5 g, 3.78 mmol) in toluene (50 mL) was treated with triphosgene (0.4 g, 1.35 mmol) and heated at reflux for 5 hours. The reaction mixture was allowed to cool to room temperature and concentrated under reduced pressure. The residue was taken up in diethyl ether, filtered, and the filtrate was concentrated under reduced pressure to provide title compound as yellow oil (0.4 g). $^1$H NMR (300 MHz, CDCl$_3$-d$_6$) δ 6.62 (m, 1H), 6.84 (d, 1H), 7.1 (t, 1H), 7.23 (m, 2H), 8.3 (s, 1H).

EXAMPLE 80B

N-1H-indol-4-yl-N'-[4-(trifluoromethyl)benzyl]urea

The product of Example 80A (0.15 g, 1 mmol) in THF (3 mL) was treated with 4-(trifluoromethyl)benzylamine (0.19 g, 1.1 mmol) at ambient temperature. After stirring for 3 hours, hexane was added to the reaction mixture to precipitate the title compound as a solid. mp 178° C. $^1$H NMR (300 MHz, DMSO-d$_6$) δ 4.43 (d, 2H), 6.53 (t, 1H), (6.98 m, 3H), 7.26 (t, 1H), 7.57 (d, 2H), 7.62 (d, 1H), 7.71 (d, 2H), 8.37 (s, 1H), 11.04 (s, 1H); MS (DCI+) m/z 334 (M+H); Anal. Calcd. For $C_{17}H_{14}N_3F_3O$: C, 61.26; H, 4.23; N, 12.61. Found: C, 61.28, H, 3.83: N, 12.31.

EXAMPLE 81

N-1H-indol-4-yl-N'-[4-(trifluoromethoxy)benzyl]urea 4-(Trifluoromethoxy)benzylamine (0.21 g, 1.1 mmol) and the product of Example 80A (0.16 g, 1 mmol) were treated as described in Example 80B to provide the title compound (0.23 g). mp 177° C.; $^1$H NMR (300 MHz, DMSO-d$_6$) δ 4.36 (d, 2H), 6.52 (m, 1H), 6.95 (m, 3H), 7.24 (t, 1H), 7.36 (d, 2H), 7.48 (d, 2H), 7.63 (dd, 1H), 8.32 (1H), 11.06 (s, 1H), 12.07. Found: C, 58.51, H, 3.98, N, 12.03.

EXAMPLE 82

N-[3-fluoro-4-(trifluoromethyl)benzyl]-N'-1H-indol-4-ylurea

3-Fluoro-4-(trifluoromethyl)benzylamine (0.22 g, 1.1 mmol) and the product of Example 80A (0.16 g, 1 mmol) were treated as described in Example 80B to provide the title compound (0.24 g). mp 198° C.; $^1$H NMR (300 MHz, DMSO-d$_6$) δ 4.43 (d, 2H), 6.52 (m, 1H), 6.98 (m, 3H), 7.26 (m, 1H), 7.39 (m, 2H), 7.57 (dd, 1H), 7.77 (t, 1H), 8.40 (s, 1H), 11.05 (s, 1H); MS (DCI+) m/z 349.9 (M+H)$^+$. Anal. Calcd. for $C_{17}H_{13}N_3F_4O$: C, 58.12; H, 3.73; N, 11.96. Found C, 58.52; H, 3.99; N, 11.55.

EXAMPLE 83

1-(4-chloro-3-trifluoromethyl-benzyl)-3-(1H-indol-4-yl)-urea

4-Chloro-3-(trifluoromethyl)benzylamine (0.27 g, 1.1 mmol) and the product of Example 80A (0.16 g, 1 mmol)

were treated as described in Example 80B to provide the title compound. mp 197° C.; ¹H NMR (300 MHz, DMSO-d₆) δ 4.42 (d, 2H), 6.52 (m, 1H), 6.96 (m, 3H), 7.25 (m, 1H), 7.56 (dd, 1H), 7.67 (dd, 1H), 7.70 (t, 1H), 7.81 (s, 1H), 8.37 (s, 1H), 11.06 (s, 1H); MS (DCI+) m/z 368 (M+H). Anal. Calcd. for $C_{17}H_{13}N_3ClF_3O$: C, 55.52, H, 3.56; N, 11.43. Found C, 55.46; H, 3.65; N, 11.58.

EXAMPLE 84

1-(4-chloro-3-trifluoromethyl)-3-(1H-indol-4-yl)-urea

4-Chlorobenzylamine (0.2 g, 1.4 mmol) and the product of Example 80A (0.2 g, 127 mmol) were treated as described in Example 80B to provide the title compound. mp 205° C. ¹H NMR (300 MHz, DMSO-d₆) δ 4.32 (d, 2H), 6.52 (m, 1H), 6.87 (m, 1H), 6.97 (m, 2H), 7.25 (m, 1H), 7.37 (m, 4H), 7.6 (m, 1H), 8.30 (s, 1H), 11.06 (s, 1H). MS (DCI+) m/z 300 (M+H). Anal. Calcd. for $C_{16}H_{14}N_3Cl_3O$: C, 64.11; H, 4.71; N, 14.02. Found: C, 63.99; H, 4.70; N, 13.77.

EXAMPLE 85

N-[2-(2,4-dichlorophenyl)ethyl]-N'-1H-indol-4-ylurea 2-(2,4-Dichlorophenyl)ethylamine (0.21 g, 1.1 mmol) and the product of Example 80A (0.16 g, 1. mmol) were treated as described in Example 80B to provide the title compound. mp 170° C.; ¹H NMR (300 MHz, DMSO-d₆) δ 2.90 (m, 2H), 3.31 (m, 2H), 6.47 (m, 2H), 6.93 (m, 2H), 7.23 (m, 1H), 7.40 (m, 2H), 7.60 (m, 2H), 8.15 (s, 1H), 11.02 (s, 1H). MS (DCI+) m/z 347 (M+H). Anal. Calcd. for $C_{17}H_{15}N_3Cl_2O$: C, 58.63; H, 4.34; N, 12.07. Found: C, 58.49; H, 4.49; N, 12.38.

EXAMPLE 86

4-(trifluoromethyl)benzyl 1H-indol-4-ylcarbamate

[4-(Trifluoromethyl)phenyl]methanol (0.09 g, 0.55 mmol) and the product of Example 80A (0.08 g, 0.5 mmol) in THF (5 mL) were heated at reflux for 16 hours with a catalytic amount of triethylamine. The reaction mixture was concentrated under reduced pressure and the residue was purified by chromatography on silica gel eluting with 50% hexane:ethylacetate to provide the title compound as an oil (0.09 g). ¹H NMR (300 MHz, DMSO-d₆) δ 5.32 (s, 2H), 6.73 (s, 1H), 7.0 (t, 1H), 7.11 (d, 1H), 7.23 (t, 1H), 7.38 (d, 1H), 7.66 (d, 2H), 7.78 (d, 2H), 9.52 (s, 1H), 11.08 (s, 1H). Anal. Calcd. for $C_{17}H_{13}N_2F_3O_2$; C, 61.08; H, 3.92; N, 8.38. Found: C, 60.97; H, 4.21; N, 8.17.

EXAMPLE 87

4-(trifluoromethoxy)benzyl 1H-indol-4-ylcarbamate

[4-(Trifluoromethoxy)pheny]methanol (0.13 g, 0.7 mmol) and the product of Example 80A (0.1 g, 0.63 mmol) in THF (5 mL) were heated at reflux for 16 hours with a catalytic amount of triethylamine. The reaction mixture was concentrated under reduced pressure and the residue was triturated with diethyl ether/hexane to provide the title compound as tan crystals (0.12 g). ¹H NMR (300 MHz, DMSO-d₆) δ 5.21 (s, 2H), 6.73 (s, 1H), 7.01 (t, 1H), 7.1 (d, 1H), 7.23 (t, 1H), 7.38 (dd, 1H), 7.4 (d, 2H), 7.6 (d, 2H), 9.5 (s, 1H), 11.06 (s, 1H). Anal. Calcd. for $C_{17}H_{13}N_2F_3O_3$. 0.25 $H_2O$: C, 57.55; H, 3.84; N, 7.90. Found: C, 57.42; H, 3.81; N, 7.32.

EXAMPLE 88

N-(4-bromobenzyl)-N'-(2,3-dimethyl-1H-indol-4-yl)urea 2,3-Dimethyl-4-aminoindole (0.11 g, 0.7 mmol) in THF (3 mL) was treated with 1-bromo-4-(isocyanatomethyl) benzene (0.17 g, 0.8 mmol) at ambient temperature. After stirring for 3 hours at ambient temperature, hexane was added to the reaction mixture to precipitate the title compound as a tan solid (0.12 g). mp 190° C. ¹H NMR (300 MHz, DMSO-d₆) δ 2.24 (s, 3H), 2.25 (s, 3H), 4.25 (d, 2H), 6.51 (t, 1H), 6.82 (t, 1H), 6.85 (d, 2H), 6.95 (m, 2H), 7.25 (d, 2H), 7.53 (d, 2H), 7.78 (s, 1H), 11.04 (s, 1H); MS (DCI+) m/z 346 (M+H)⁺; Anal. Calcd. for $C_{18}H_{18}N_3BrO$: C, 58.08; H, 4.87; N, 11.29. Found: C, 57.97, H, 4.92; N, 11.30.

EXAMPLE 89

N-(4-bromobenzyl)-N'-1H-indazol-4-ylurea

EXAMPLE 89A 1H-indazol-4-amine

4-Nitro-1H-indazole (1.63 g, 10 mmol) in ethanol (100 mL) was treated with $BiCl_3$ (3.46 g, 11 mmol) followed by a portionwise addition of $NaBH_4$. The reaction mixture was stirred at ambient temperature for 20 minutes and filtered through Celite. The filtrate was evaporated under reduced pressure and the residue was partitioned between ethyl acetate/dilute $NaHCO_3$ solution. The organic layer was dried over $MgSO_4$, filtered, and the filtrate concentrated under reduced pressure to provide the title compound as a tan solid (1.0 g). ¹H NMR (300 MHz, DMSO-d₆) δ 5.64 (s, 2H), 6.1 (d, 1H), 6.6 (d, 1H), 6.98 (t, 1H), 8.03 (s, 1H), 12.6 (s, 1H).

EXAMPLE 89B

N-(4-bromobenzyl)-N'-1H-indazol-4-ylurea hydrochloride salt

The product of Example 89A (0.16 g, 1.2 mmol) in THF (10 mL) was treated with 1-bromo-4-(isocyanatomethyl) benzene (0.52 g, 2.4 mmol) at room temperature. After stirring for 16 hours, the reaction mixture was concentrated and the residue was treated with methanol (20 mL) and 3N HCl (10 mL) and heated at reflux for 3 hours. The reaction mixture was allowed to cool to room temperature, evaporated under reduced pressure, and the residue was treated with water and the pH adjusted to 5. The obtained compound was purified by chromatography eluting with 5% of ethanol:methylene chloride and converted to HCl salt mp 126° C. ¹H NMR (300 MHz, DMSO-d₆) δ 4.32 (d, 2H), 7.0 (t, 1H), 7.05 (d, 1H), 7.18 (t, 1H), 7.3 (d, 2H), 7.55 (d, 2H), 7.61 (d, 1H), 8.16 (s, 1H), 8.92 (s, 1H); Analysis Calcd for $C_{15}H_{13}N_4BrO$ HCl: C, 47.21; H, 3.70; N, 14.68. Found C, 46.99; H, 4.08; N, 14.13.

EXAMPLE 90

N-(3,4-dichlorobenzyl)-N'-1H-indazol-4-ylurea

EXAMPLE 90A methyl 4-nitro-1H-indazole-1-carboxylate

Sodium hydride (0.3 g, 12.5 mmol) suspended in DMF (5 mL) at 0° C. was treated with 4-nitro-1H-indazole (1.33 g, 10 mmol). After stirring at room temperature for 1 hours, the mixture was treated with methylchloroformate (0.9 mL). After stirring at room temperature for 3 hours, the mixture was carefully treated with water and filtered to provide the title compound (1.2 g). ¹H NMR (300 MHz, DMSO-d₆) δ 4.19 (s, 3H), 7.9 (t, 1H), 8.38 (d, 1H), 8.62 (d, 1H), 8.85 (s, 1H).

EXAMPLE 90B methyl 4-amino-1H-indazole-1-carboxylate

The product of Example 90A (1.66 g, 7.5 mmol) in ethanol (20 mL) was treated with $BiCl_3$ (8.2 g, 2.6 mmol)

followed by the addition of NaBH$_4$ (1.13 g, 30.5 mmol). The reaction mixture was stirred at room temperature for 20 minutes, filtered through Celite, and the filtrate was evaporated under reduced pressure. The residue was partitioned between ethyl acetate/dilute NaHCO$_3$ solution. The organic phase was separated, dried over MgSO$_4$, filtered and the filtrate concentrated under reduced pressure to provide the title compound (1.2 g). $^1$H NMR (300 MHz, DMSO-d$_6$) δ 6.1 (s, 2H), 6.41 (dd, 1H), 7.21 (m, 2H), 8.42 (s, 1H).

EXAMPLE 90C methyl 4-({[(3,4-dichlorobenzyl)amino]carbonyl}amino)-1H-indazole-1-carboxylate The product of Example 90B (0.19 g, 1 mmol) in THF (3 mL) was treated with 1,2-dichloro-4-(isocyanatomethyl)benzene (0.22 g, 1.1 mmol) at ambient temperature. After stirring for 3 hours, hexane was added to the reaction mixture to precipitate the title compound as a tan solid (0.25 g). $^1$H NMR (300 MHz, DMSO-d$_6$) δ 4.38 (d, 2H), 6.97 (t, 1H), 7.36 (dd, 1H), 7.48 (t, 1H), 7.6 (m, 2H), 7.7 (d, 1H), 7.8 (d, 1H), 8.45 (s, 1H), 9.16 (s, 1H).

EXAMPLE 90D

N-(3,4-dichlorobenzyl)-N'-1H-indazol-4-ylurea

The product of Example 90C (0.25 g, 0.6 mmol) was heated at reflux in methanol (5 mL) and 0.5N KOH (1 mL) for 0.5 hours. The reaction mixture was allowed to cool to ambient temperature, pH was adjusted to 5, and volume was reduced under reduced pressure. Methylene chloride and water was added, the phases were separated, and the organic phase concentrated under reduced pressure to provide the title compound. $^1$H NMR (300 MHz, DMSO-d$_6$) δ 4.38 (d, 2H), 6.9 (t, 1H), 7.05 (d, 1H), 7.19 (t, 1H), 7.35 (dd, 1H), 7.6 (m, 2 H), 8.06 (s, 1H), 8.82 (s, 1H). MS (DCI+) m/z 336 (M+H)$^+$; Anal. Calcd. For C$_{15}$H$_{13}$N$_4$Cl$_2$O: C, 53.75; H, 3.62; N, 16.72. Found: C, 53.84, H, 3.44; N, 16.88.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

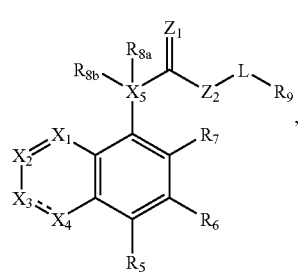

(I)

or a pharmaceutically acceptable salt or prodrug thereof, wherein

- - - is absent or is a single bond;

X$_1$ is CR$_1$;

X$_2$ is selected from the group consisting of N and CR$_2$;

X$_3$ is selected from the group consisting of N and CR$_3$;

X$_4$ is CR$_4$;

X$_5$ is selected from the group consisting of N and C;

provided that only one of X$_2$, and X$_3$ is N;

Z$_1$ is O;

Z$_2$ is a bond or selected from the group consisting of NH and O;

L is selected from the group consisting of alkenylene, alkylene, cycloalkylene,

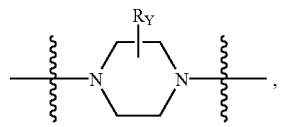

—(CH$_2$)$_m$O(CH$_2$)$_n$—, and N(R$_Y$), wherein the left end of —(CH$_2$)$_m$O(CH$_2$)$_n$— is attached to Z$_2$ and the right end is attached to R$_9$;

m and n are each independently 1–6;

R$_Y$ is selected from the group consisting of hydrogen and alkyl;

R$_1$, R$_3$, R$_5$, R$_6$, and R$_7$ are each independently selected from the group consisting of hydrogen, alkoxy, alkoxyalkoxy, alkoxyalkyl, alkyl, alkylcarbonyloxy, carboxy, carboxyalkyl, cyano, cyanoalkyl, haloalkoxy, haloalkyl, haloalkylthio, halogen, hydroxy, hydroxyalkyl, —NR$_A$S(O)$_2$R$_B$, —S(O)$_2$R$_B$, —NZ$_A$Z$_B$, (NZ$_A$Z$_B$)alkyl, (NZ$_A$Z$_B$)carbonylalkyl and (NZ$_A$Z$_B$)sulfonyl, wherein Z$_A$ and Z$_B$ are each independently selected from the group consisting of hydrogen, alkyl, alkylcarbonyl, aryl, and arylalkyl;

R$_2$ and R$_4$ are each independently selected from the group consisting of hydrogen, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, carboxy, carboxyalkyl, cyano, cyanoalkyl, cycloalkyl, cycloalkylalkyl, haloalkoxy, haloalkyl, haloalkylthio, halogen, hydroxy, hydroxyalkyl, —NR$_A$S(O)$_2$R$_B$, —S(O)$_2$OR$_A$, —S(O)$_2$R$_B$, —NZ$_A$Z$_B$, (NZ$_A$Z$_B$)alkyl, (NZ$_A$Z$_B$)alkylcarbonyl, (NZ$_A$Z$_B$)carbonyl, (NZ$_A$Z$_B$)carbonylalkyl, and (NZ$_A$Z$_B$)sulfonyl;

R$_A$ is selected from the group consisting of hydrogen and alkyl;

R$_B$ is selected from the group consisting of alkyl, aryl, and arylalkyl;

R$_{8a}$ is selected from the group consisting of hydrogen and alkyl;

R$_{8b}$ is absent when X$_5$ is N or R$_{8b}$ is selected from the group consisting of hydrogen, alkoxy, alkoxycarbonylalkyl, alkyl, alkylcarbonyloxy, alkylsulfonyloxy, halogen, and hydroxy when X$_5$ is C; and R$_9$ is selected from the group consisting of hydrogen, aryl, cycloalkyl, and heterocycle.

2. The compound according to claim 1 wherein

- - - is a single bond;

X$_1$ is CR$_1$;

X$_2$ is CR$_2$;

X$_3$ is N; and

X$_4$ is CR$_4$.

3. The compound according to claim 2 wherein $X_5$ is N;

$R_{8b}$ is absent;

$Z_1$ is O;

$Z_2$ is NH;

L is alkylene; and $R_9$ is aryl.

4. The compound according to claim 2 wherein $X_5$ is N;

$R_1$, $R_6$ and $R_7$ are each hydrogen;

$R_2$ and $R_4$ are independently selected from the group consisting of hydrogen, alkyl, halogen, hydroxy, and —$NZ_AZ_B$;

$R_5$ is selected from the group consisting of hydrogen and halogen;

$R_{8a}$ is hydrogen;

$R_{8b}$ is absent;

$Z_1$ is O;

$Z_2$ is NH;

L is alkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$, and $Z_D$ are independently selected from the group consisting of hydrogen and alkyl.

5. The compound according to claim 4 selected from the group consisting of N-[2-(3-fluorophenyl)ethyl]-N'-isoquinolin-5-ylurea;

N-[2-(3-bromophenyl)ethyl]-N'-isoquinolin-5-ylurea;

N-isoquinolin-5-yl-N'-[4-(trifluoromethyl)benzyl]urea;

N-[3-fluoro-5-(trifluoromethyl)benzyl]-N'-isoquinolin-5-ylurea;

N-(2,5-dichlorobenzyl)-N'-isoquinolin-5-ylurea;

N-(1,3-benzodioxol-5-ylmethyl)-N'-isoquinolin-5-ylurea;

N-[2-(4-fluorophenyl)ethyl]-N'-isoquinolin-5-ylurea;

N-(3-bromobenzyl)-N'-isoquinolin-5-ylurea;

N-[2-(3,4-dimethylphenyl)ethyl]-N'-isoquinolin-5-ylurea;

N-[1-(4-bromophenyl)ethyl]-N'-isoquinolin-5-ylurea;

N-isoquinolin-5-yl-N'-[4-(trifluoromethoxy)benzyl]urea;

N-isoquinolin-5-yl-N'-(4-methylbenzyl)urea;

N-(4-fluorobenzyl)-N'-isoquinolin-5-ylurea;

N-[2-(3,4-dichlorophenyl)ethyl]-N'-isoquinolin-5-ylurea;

N-[2-(3,5-dimethoxyphenyl)ethyl]-N'-isoquinolin-5-ylurea;

N-(4-chlorobenzyl)-N'-isoquinolin-5-ylurea;

N-isoquinolin-5-yl-N'-{2-[3-(trifluoromethyl)phenyl]ethyl}urea;

N-[2-(2,6-dichlorophenyl)ethyl]-N'-isoquinolin-5-ylurea;

N-[2-(2,3-dichlorophenyl)ethyl]-N'-isoquinolin-5-ylurea;

N-isoquinolin-5-yl-N'-[3-(trifluoromethoxy)benzyl]urea;

N-[2-(4-ethoxy-3-methoxyphenyl)ethyl]-N'-isoquinolin-5-ylurea;

N-[2-(2,4-dichlorophenyl)ethyl]-N'-isoquinolin-5-ylurea;

N-(3-bromo-4-fluorobenzyl)-N'-isoquinolin-5-ylurea;

N-(3,4-dimethylbenzyl)-N'-isoquinolin-5-ylurea;

N-isoquinolin-5-yl-N'-(3-phenylpropyl)urea;

N-(3,5-dichlorobenzyl)-N'-isoquinolin-5-ylurea;

N-(3-chloro-4-methylbenzyl)-N'-isoquinolin-5-ylurea;

N-(3,4-dichlorobenzyl)-N'-isoquinolin-5-ylurea;

N-(3-fluorobenzyl)-N'-isoquinolin-5-ylurea;

N-(4-tert-butylbenzyl)-N'-isoquinolin-5-ylurea;

N-isoquinolin-5-yl-N'-[2-(3-methylphenyl)ethyl]urea;

N-isoquinolin-5-yl-N'-[2-(4-methylphenyl)ethyl]urea;

N-[2-(2,4-dimethylphenyl)ethyl]-N'-isoquinolin-5-ylurea;

N-isoquinolin-5-yl-N'-[2-(2-methylphenyl)ethyl]urea;

N-isoquinolin-5-yl-N'-{4-[(trifluoromethyl)thio]benzyl}urea;

N-isoquinolin-5-yl-N'-[3-(trifluoromethyl)benzyl]urea;

N-[4-chloro-3-(trifluoromethyl)benzyl]-N'-isoquinolin-5-ylurea;

N-(3,5-dimethylbenzyl)-N'-isoquinolin-5-ylurea;

N-(3,5-difluorobenzyl)-N'-isoquinolin-5-ylurea;

N-(4-bromobenzyl)-N'-isoquinolin-5-ylurea;

N-(3,5-dimethoxybenzyl)-N'-isoquinolin-5-ylurea;

N-isoquinolin-5-yl-N'-(3,4,5-trimethoxybenzyl)urea;

N-isoquinolin-5-yl-N'-[4-(methylsulfonyl)benzyl]urea;

N-(3,4-dimethoxybenzyl)-N'-isoquinolin-5-ylurea;

N-isoquinolin-5-yl-N'-(1-naphthylmethyl)urea;

N-(2,4-dimethylbenzyl)-N'-isoquinolin-5-ylurea;

N-[4-(dimethylamino)benzyl]-N'-isoquinolin-5-ylurea;

N-(4-bromobenzyl)-N'-(3-chloroisoquinolin-5-yl)urea;

N-[(4-cyanophenyl)methyl]-N'-isoquinolin-5-ylurea;

N-[(4-bromophenyl)methyl]-N'-(3-methylisoquinolin-5-yl)urea;

N-[(4-bromophenyl)methyl]-N'-(1-chloroisoquinolin-5-yl)urea;

N-[(4-bromophenyl)methyl]-N'-(1-methylisoquinolin-5-yl)urea;

N-isoquinolin-5-yl-N'-[(4-morpholin-4-ylphenyl)methyl]urea;

N-{[4-(2,6-dimethylmorpholin-4-yl)phenyl]methyl}-N'isoquinolin-5ylurea

N-isoquinolin-5-yl-N'-[(4-thiomorpholin-4-ylphenyl)methyl]urea;

methyl 5-({[(4-bromobenzyl)amino]carbonyl}amino)isoquinoline-3-carboxylate;

methyl 5-({[(2,4-dichlorobenzyl)amino]carbonyl}amino)isoquinoline-3-carboxylate;

N-(8-bromoisoquinolin-5-yl)-N'-(2,4-dichlorobenzyl)urea;

N-(8-bromoisoquinolin-5-yl)-N'-(4-fluorobenzyl)urea;

N-(8-bromoisoquinolin-5-yl)-N'-(3-fluorobenzyl)urea;

N-[1-(4-chlorophenyl)-1-methylethyl]-N'-isoquinolin-5-ylurea;

N-(1,1'-biphenyl-4-ylmethyl)-N'-5-isoquinolinylurea;

N-[3-fluoro-4-(trifluoromethyl)benzyl]-N'-5-isoquinolinylurea;

N-5-isoquinolinyl-N'-(3-methylbenzyl)urea;

N-[4-fluoro-3-(trifluoromethyl)benzyl]-N'-5-isoquinolinylurea;

N-(3-chloro-4-fluorobenzyl)-N'-5-isoquinolinylurea;

N-5-isoquinolinyl-N'-[4-(1-pyrrolidinyl)benzyl]urea;
N-[4-(1-azepanyl)benzyl]-N'-5-isoquinolinylurea;
N-[3-fluoro-4-(1-pyrrolidinyl)benzyl]-N'-5-isoquinolinylurea;
N-[4-(1-azepanyl)-3-fluorobenzyl]-N'-5-isoquinolinylurea;
N-[4-(1-azocanyl)benzyl]-N'-5-isoquinolinylurea;
N-benzhydryl-N'-5-isoquinolinylurea;
N-[(1S)-1-(4-bromophenyl)ethyl]-N'-5-isoquinolinylurea;
N-[(1R)-1-(4-bromophenyl)ethyl]-N'-5-isoquinolinylurea;
N-5-isoquinolinyl-N'-{1-[4-(trifluoromethyl)phenyl]ethyl}urea;
(−) N-5-isoquinolinyl-N'-{(1S)-1-[4-(trifluoromethyl)phenyl]ethyl}urea;
(+) N-5-isoquinolinyl-N'-{(1S)-1-[4-(trifluoromethyl)phenyl]ethyl}urea;
N-[1-(4-tert-butylphenyl)ethyl]-N'-5-isoquinolinylurea;
N-{cyclopropyl[4-(trifluoromethyl)phenyl]methyl}-N'-5-isoquinolinylurea;
N-(3-fluorobenzyl)-N'-(3-methyl-5-isoquinolinyl)urea;
N-(4-bromo-3-fluorobenzyl)-N'-5-isoquinolinylurea;
N-(3-amino-5-isoquinolinyl)-N'-[4-(1-piperidinyl)benzyl]urea;
N-(3-amino-5-isoquinolinyl)-N'-[4-(1-azepanyl)benzyl]urea;
N-(1,1'-biphenyl-3-ylmethyl)-N'-5-isoquinolinylurea;
N-5-isoquinolinyl-N'-[4-(2-pyridinyl)benzyl]urea;
N-(4-bromo-3-fluorobenzyl)-N'-(3-methyl-5-isoquinolinyl)urea;
N-[3-fluoro-4-(4-methyl-1-piperidinyl)benzyl]-N'-(3-methyl-5-isoqinolinyl)urea;
N-(3-methyl-5-isoquinolinyl)-N'-[4-(4-methyl-1-piperidinyl)benzyl]urea;
N-[3-fluoro-4-(1-piperidinyl)benzyl]-N'-(3-methyl-5-isoquinolinyl)urea;
N-(3-methyl-5-isoquinolinyl)-N'-[4-(1-piperidinyl)benzyl]urea;
N-[4-(1-azepanyl)benzyl]-N'-(3-methyl-5-isoquinolinyl)urea;
N-(3-methyl-5-isoquinolinyl)-N'-[4-(1-pyrrolidinyl)benzyl]urea;
N-[3-fluoro-4-(1-pyrrolidinyl)benzyl]-N'-(3-methyl-5-isoquinolinyl)urea;
N-[4-(1-azepanyl)-3-fluorobenzyl]-N'-(3-methyl-5-isoquinolinyl)urea;
N-[4-(1-azocanyl)benzyl]-N'-(3-methyl-5-isoquinolinyl)urea;
N-[4-(1-azocanyl)-3-fluorobenzyl]-N'-(3-methyl-5-isoquinolinyl)urea;
N-[(1S)-1-(4-bromophenyl)ethyl]-N'-(3-methyl-5-isoquinolinyl)urea;
N-{(1S)-1-[4-(1-azepanyl)phenyl]ethyl}-N'-(3-methyl-5-isoquinolinyl)urea;
N-benzyl-N'-(3-chloro-5-isoquinolinyl)urea;
N-(4-bromobenzyl)-N'-(1-chloro-5-isoquinolinyl)urea;
N-(4-cyanobenzyl)-N'-5-isoquinolinylurea;
N-(4-bromobenzyl)-N'-(3-methyl-5-isoquinolinyl)urea;
N-(4-bromobenzyl)-N'-(1-methyl-5-isoquinolinyl)urea;
N-5-isoquinolinyl-N'-[4-(4-morpholinyl)benzyl]urea;
N-[4-(2,6-dimethyl-4-morpholinyl)benzyl]-N'-5-isoquinolinylurea;
N-5-isoquinolinyl-N'-[4-(4-thiomorpholinyl)benzyl]urea;
N-(4-bromobenzyl)-N'-(3-fluoro-5-isoquinolinyl)urea;
N-(3-chloro-5-isoquinolinyl)-N'-[4-(4-morpholinyl)benzyl]urea;
N-[3,5-difluoro-4-(4-morpholinyl)benzyl]-N'-5-isoquinolinylurea;
N-(4-bromobenzyl)-N'-(1,3-dimethyl-5-isoquinolinyl)urea;
N-(3,4-dimethylbenzyl)-N'-(3-methyl-5-isoquinolinyl)urea;
N-[3,5-bis(trifluoromethyl)benzyl]-N'-(3-methyl-5-isoquinolinyl)urea;
N-(3-amino-5-isoquinolinyl)-N'-(4-bromobenzyl)urea;
N-(3-methyl-5-isoquinolinyl)-N'-[4-(trifluoromethyl)benzyl]urea;
N-(4-tert-butylbenzyl)-N'-(3-methyl-5-isoquinolinyl)urea;
N-(4-tert-butylbenzyl)-N'-(1,3-dimethyl-5-isoquinolinyl)urea;
N-(4-tert-butylbenzyl)-N'-(1,3-dimethyl-5-isoquinolinyl)urea;
N-[3-fluoro-4-(trifluoromethyl)benzyl]-N'-(3-methyl-5-isoquinolinyl)urea;
N-[1-(4-bromophenyl)ethyl]-N'-(3-methyl-5-isoquinolinyl)urea;
N-(3,4-dichlorobenzyl)-N'-(3-methyl-5-isoquinolinyl)urea;
N-(2,4-dichlorobenzyl)-N'-(3-methyl-5-isoquinolinyl)urea;
N-(3-chlorobenzyl)-N'-(3-methyl-5-isoquinolinyl)urea;
N-(3-methyl-5-isoquinolinyl)-N'-[4-(trifluoromethoxy)benzyl]urea;
N-[2-(3,4-dichlorophenyl)ethyl]-N'-(3-methyl-5-isoquinolinyl)urea;
N-(4-ethylbenzyl)-N'-(3-methyl-5-isoquinolinyl)urea;
N-(3-methyl-5-isoquinolinyl)-N'-{2-[4-(trifluoromethyl)phenyl]ethyl}urea;
N-(3-methyl-5-isoquinolinyl)-N'-{4-[(trifluoromethyl)thio]benzyl}urea;
N-(4-chlorobenzyl)-N'-(3-methyl-5-isoquinolinyl)urea;
N-(2,4-difluorobenzyl)-N'-(3-methyl-5-isoquinolinyl)urea;
N-(1,3-dimethyl-5-isoquinolinyl)-N'-[3-fluoro-4-(trifluoromethyl)benzyl]urea;
N-(4-isopropylbenzyl)-N'-(3-methyl-5-isoquinolinyl)urea;
N-[4-fluoro-3-(trifluoromethyl)benzyl]-N'-(3-methyl-5-isoquinolinyl)urea;
N-(3-amino-5-isoquinolinyl)-N'-{1-[4-(trifluoromethyl)phenyl]ethyl}urea;
N-(3-amino-5-isoquinolinyl)-N'-[3-fluoro-4-(trifluoromethyl)benzyl]urea;
N-(5-bromo-2-fluorobenzyl)-N'-5-isoquinolinylurea;
N-(4-chloro-2-fluorobenzyl)-N'-5-isoquinolinylurea;
N-(4-tert-butylbenzyl)-N'-5-isoquinolinylurea;
N-(3,4-difluorobenzyl)-N'-5-isoquinolinylurea;
N-{1-[3-fluoro-4-(trifluoromethyl)phenyl]ethyl}-N'-5-isoquinolinylurea;

N-{1-[3-fluoro-4-(trifluoromethyl)phenyl]propyl}-N'-5-isoquinolinylurea;
N-(8-bromo-5-isoquinolinyl)-N'-(2,4-dichlorobenzyl)urea;
N-(8-bromo-5-isoquinolinyl)-N'-(4-fluorobenzyl)urea;
N-(8-bromo-5-isoquinolinyl)-N'-(3-fluorobenzyl)urea;
N-[1-(4-chlorophenyl)-1-methylethyl]-N'-5-isoquinolinylurea;
N-(4-bromo-3-methylbenzyl)-N'-5-isoquinolinylurea;
N-[2-fluoro-4-(trifluoromethyl)benzyl]-N'-5-isoquinolinylurea;
N-(4-bromobenzyl)-N'-(3-hydroxy-5-isoquinolinyl)urea;
N-[3-bromo-4-(trifluoromethyl)benzyl]-N'-5-isoquinolinylurea;
N-[2,4-bis(trifluoromethyl)benzyl]-N'-5-isoquinolinylurea;
N-[2,3-difluoro-4-(trifluoromethyl)benzyl]-N'-5-isoquinolinylurea;
N-[2-chloro-4-(trifluoromethyl)benzyl]-N'-5-isoquinolinylurea;
N-5-isoquinolinyl-N'-{1-methyl-1-[4-(trifluoromethyl)phenyl]ethyl}urea; and
N-[2-(4-bromophenyl)-2-hydroxyethyl]-N'-5-isoquinolinylurea.

6. The compound according to claim 2 wherein
$X_5$ is N;
$R_1$, $R_2$, $R_4$, $R_5$, $R_6$ and $R_7$ are each hydrogen;
$R_{8b}$ is absent;
$Z_1$ is O;
$Z_2$ is NH;
L is alkylene; and
$R_9$ is aryl wherein said aryl is substituted with aryloxy.

7. The compound according to claim 2 wherein
$X_5$ is N;
$R_1$, $R_2$, $R_4$, $R_5$, $R_6$ and $R_7$ are each hydrogen;
$R_{8a}$ is hydrogen;
$R_{8b}$ is absent;
$Z_1$ is O;
$Z_2$ is NH;
L is alkylene;
$R_9$ is aryl wherein said aryl is phenyl substituted with aryloxy wherein said aryloxy is phenoxy substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

8. The compound according to claim 7 selected from the group consisting of
N-isoquinolin-5-yl-N'-(4-phenoxybenzyl)urea; and
N-isoquinolin-5-yl-N'-(3-phenoxybenzyl)urea.

9. The compound according to claim 2 wherein
$X_5$ is N;
$R_1$, $R_2$, $R_4$, $R_5$, $R_6$ and $R_7$ are each hydrogen;
$R_{8a}$ is hydrogen;
$R_{8b}$ is absent;
$Z_1$ is O;
$Z_2$ is NH;
L is alkylene; and
$R_9$ is aryl wherein said aryl is napthyl.

10. The compound according to claim 9 that is N-isoquinolin-5-yl-N'-(1-naphthylmethyl)urea.

11. The compound according to claim 2 wherein
$X_5$ is N;
$R_{8b}$ is absent;
$Z_1$ is O;
$Z_2$ is NH;
L is alkylene; and
$R_9$ is cycloalkyl.

12. The compound according to claim 2 wherein
$X_5$ is N;
$R_1$, $R_6$ and $R_7$ are each hydrogen;
$R_2$ and $R_4$ are independently selected from the group consisting of hydrogen, alkyl, halogen, hydroxy, and —$NZ_AZ_B$;
$R_5$ is selected from the group consisting of hydrogen and alkyl;
$R_{8a}$ is hydrogen;
$R_{8b}$ is absent;
$Z_1$ is O;
$Z_2$ is NH;
L is alkylene;
$R_9$ is cycloalkyl wherein said cycloalkyl is selected from the group consisting of adamantyl, bicyclo[3.1.1]heptyl, and cyclohexyl, wherein the cycloalkyl is substituted with 0, 1 or 2 alkyl groups; and
$Z_A$ and $Z_B$ are independently selected from the group consisting of hydrogen and alkyl.

13. The compound according to claim 12 selected from the group consisting of
N-(1-adamantylmethyl)-N'-5-isoquinolinylurea;
N-(cyclohexylmethyl)-N'-5-isoquinolinylurea;
N-[(6,6-dimethylbicyclo[3.1.1]hept-2-yl)methyl]-N'-5-isoquinolinylurea;
N-[(4-tert-butylcyclohexyl)methyl]-N'-5-isoquinolinylurea; and
N-5-isoquinolinyl-N'-{[4-(trifluoromethyl)cyclohexyl]methyl}urea.

14. The compound according to claim 2 wherein
$X_5$ is N;
$R_{8b}$ is absent;
$Z_1$ is O;
$Z_2$ is NH;
L is alkylene; and
$R_9$ is heterocycle.

15. The compound according to claim 2 wherein
$X_5$ is N;
$R_1$, $R_6$ and $R_7$ are each hydrogen;
$R_2$ and $R_4$ are independently selected from the group consisting of hydrogen, alkyl, halogen, hydroxy, and —$NZ_AZ_B$;
$R_5$ is selected from the group consisting of hydrogen and halogen;
$R_{8a}$ is hydrogen;
$R_{8b}$ is absent;
$Z_1$ is O;

$Z_2$ is NH;

L is alkylene;

$R_9$ is heterocycle wherein said heterocycle is pyridinyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$, and $Z_D$ are independently selected from the group consisting of hydrogen and alkyl.

16. The compound according to claim 15 that is N-5-isoquinolinyl-N'-{[5-(trifluoromethyl)-2-pyridinyl]methyl}urea.

17. The compound according to claim 2 wherein $X_5$ is N;

$Z_1$ is O;

$Z_2$ is NH;

$R_{8b}$ is absent; and $R_9$ is hydrogen.

18. The compound according to claim 2 wherein $X_5$ is N;

$R_1$, $R_2$, $R_4$, $R_5$, $R_6$ and $R_7$ are each hydrogen;

$R_{8a}$ is hydrogen;

$R_{8b}$ is absent;

$Z_1$ is O;

$Z_2$ is NH;

L is alkylene; and $R_9$ is hydrogen.

19. The compound according to claim 18 selected from the group consisting of

N-hexyl-N'-isoquinolin-5-ylurea;

N-5-isoquinolinyl-N'-pentylurea; and

N-5-isoquinolinyl-N'-octylurea.

20. The compound according to claim 2 wherein $X_5$ is N;

$Z_1$ is O;

$Z_2$ is NH;

L is cycloalkylene;

$R_{8b}$ is absent; and $R_9$ is aryl.

21. The compound according to claim 2 wherein $X_5$ is N;

$R_1$, $R_2$, $R_4$, $R_5$, $R_6$ and $R_7$ are each hydrogen;

$R_{8a}$ is hydrogen;

$R_{8b}$ is absent;

$Z_1$ is O;

$Z_2$ is NH;

L is cycloalkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

22. The compound according to claim 21 that is N-isoquinolin-5-yl-N'-[(trans)-2-phenylcyclopropyl]urea.

23. The compound according to claim 2 wherein $X_5$ is N;

$Z_1$ is O;

$Z_2$ is a bond;

L is cycloalkylene;

$R_{8b}$ is absent; and $R_9$ is aryl.

24. The compound according to claim 2 wherein $X_5$ is N;

$R_1$, $R_2$, $R_4$, $R_5$, $R_6$ and $R_7$ are each hydrogen;

$R_{8a}$ is hydrogen;

$R_{8b}$ is absent;

$Z_1$ is O;

$Z_2$ is a bond;

L is cycloalkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

25. The compound according to claim 24 that is N-5-isoquinolinyl-2-phenylcyclopropanecarboxamide.

26. The compound according to claim 2 wherein $X_5$ is N;

$Z_1$ is O;

$Z_2$ is NH;

L is —$(CH_2)_mO(CH_2)_n$— wherein the left end is attached to $Z_2$ and the right end is attached to $R_9$;

$R_{8b}$ is absent; and $R_9$ is aryl.

27. The compound according to claim 2 wherein $X_5$ is N;

$R_1$, $R_2$, $R_4$, $R_5$, $R_6$, $R_7$, and $R_{8a}$ are each hydrogen;

$R_{8b}$ is absent;

$Z_1$ is O;

$Z_2$ is NH;

L is —$(CH_2)_mO(CH_2)_n$— wherein the left end is attached to $Z_2$ and the right end is attached to $R_9$;

m is 1–2;

n is 0–2;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

28. The compound according to claim 27 selected from the group consisting of
N-isoquinolin-5-yl-N'-(2-phenoxyethyl)urea; and
N-[(2,4-dichlorobenzyl)oxy]-N'-5-isoquinolinylurea.

29. The compound according to claim 2 wherein
$X_5$ is N;
$Z_1$ is O;
$Z_2$ is NH;
L is N($R_Y$);
$R_{8b}$ is absent; and
$R_9$ is aryl.

30. The compound according to claim 2 wherein
$X_5$ is N;
$R_1$, $R_2$, $R_4$, $R_5$, $R_6$, $R_7$, and $R_{8a}$ are each hydrogen;
$R_{8b}$ is absent;
$Z_1$ is O;
$Z_2$ is NH;
L is N($R_Y$);
m is 2–4;
n is 0;
$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

31. The compound according to claim 30 that is N-5-isoquinolinyl-2-[4-(trifluoromethyl)phenyl]hydrazinecarboxamide.

32. The compound according to claim 2 wherein
$X_5$ is N;
$Z_1$ is O;
$Z_2$ is a bond;

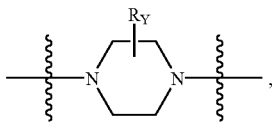

$R_{8b}$ is absent; and
$R_9$ is aryl.

33. The compound according to claim 2 wherein
$X_5$ is N;
$R_1$, $R_5$, $R_6$, $R_7$, and $R_{8a}$ are each hydrogen;
$R_{8b}$ is absent;
$R_2$ is selected from the group consisting of hydrogen and alkyl;
$Z_1$ is O;

$Z_2$ is a bond;

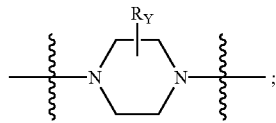

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

34. The compound according to claim 33 that is selected from the group consisting of
4-(3,4-dichlorophenyl)-N-isoquinolin-5-ylpiperazine-1-carboxamide;
4-(3-chlorophenyl)-N-5-isoquinolinyl-1-piperazinecarboxamide;
4-(3,4-dimethylphenyl)-N-5-isoquinolinyl-1-piperazinecarboxamide;
4-(4-chlorophenyl)-N-5-isoquinolinyl-1-piperazinecarboxamide;
N-5-isoquinolinyl-3-methyl-4-(4-methylphenyl)-1-piperazinecarboxamide;
4-(2,3-dimethylphenyl)-N-5-isoquinolinyl-1-piperazinecarboxamide;
4-(2,3-dichlorophenyl)-N-5-isoquinolinyl-1-piperazinecarboxamide;
4-(3,4-dichlorophenyl)-N-(3-methyl-5-isoquinolinyl)-1-piperazinecarboxamide;
N-5-isoquinolinyl-4-[3-(trifluoromethyl)phenyl]-1-piperazinecarboxamide; and
4-(4-bromophenyl)-N-5-isoquinolinyl-1-piperazinecarboxamide.

35. The compound according to claim 2 wherein
$X_5$ is N;
$R_1$, $R_2$, $R_4$, $R_5$ and $R_6$ are each hydrogen;
$R_7$ is $(CF_3)_2(HO)C$—;
$R_{8b}$ is absent;
$Z_1$ is O;
$Z_2$ is NH;
L is alkylene;
$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

36. The compound according to claim 35 that is N-(4-bromobenzyl)-N'-{6-[2,2,2-trifluoro-1-hydroxy-1-(trifluoromethyl)ethyl]isoquinolin-5-yl}urea.

37. The compound according to claim 2 wherein $X_5$ is N;
$Z_1$ is O;
$Z_2$ is O;
L is alkylene;
$R_{8b}$ is absent; and
$R_9$ is aryl.

38. The compound according to claim 2 wherein $X_5$ is N;
$R_1$, $R_2$, $R_4$, $R_5$, $R_6$, $R_7$, and $R_{8a}$ are each hydrogen;
$R_{8b}$ is absent;
$Z_1$ is O;
$Z_2$ is O;
L is alkylene;
$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_C$ and $Z_D$ are independently selected from the group consisting of hydrogen and alkyl.

39. The compound according to claim 38 selected from the group consisting of 4-(trifluoromethyl)benzyl isoquinolin-5-ylcarbamate;
2-(3-bromophenyl)ethyl isoquinolin-5-ylcarbamate;
4-cyanobenzyl isoquinolin-5-ylcarbamate;
4-methylbenzyl 5-isoquinolinylcarbamate;
4-bromobenzyl 5-isoquinolinylcarbamate;
2-(4-chlorophenyl)ethyl 5-isoquinolinylcarbamate; and
2-[2-(trifluoromethyl)phenyl]ethyl 5-isoquinolinylcarbamate.

40. The compound according to claim 2 wherein $X_5$ is N;
$R_1$, $R_2$, $R_4$, $R_5$, $R_6$ and $R_7$ are each hydrogen;
$Z_1$ is O;
$Z_2$ is O;
L is alkylene;
$R_{8b}$ is absent; and
$R_9$ is aryl wherein said aryl is naphthyl.

41. The compound according to claim 40 that is 1-naphthylmethyl isoquinolin-5-ylcarbamate.

42. The compound according to claim 2 wherein $X_5$ is N;
$R_{8b}$ is absent;
$Z_1$ is O;
$Z_2$ is a bond;
L is alkenylene; and
$R_9$ is aryl.

43. The compound according to claim 2 wherein $X_5$ is N;
$R_1$, $R_6$ and $R_7$ are each hydrogen;
$R_2$ and $R_4$ are independently selected from the group consisting of hydrogen, alkyl, halogen, hydroxy, and —$NZ_AZ_B$;
$R_5$ is selected from the group consisting of hydrogen and halogen;
$R_{8a}$ is hydrogen;
$R_{8b}$ is absent;
$Z_1$ is O;
$Z_2$ is a bond;
L is alkenylene;
$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and
$Z_A$, $Z_B$, $Z_C$ and $Z_D$ are independently selected from the group consisting of hydrogen and alkyl.

44. The compound according to claim 43 that is selected from the group consisting of (2E)-N-5-isoquinolinyl-3-[4-(trifluoromethyl)phenyl]-2-butenamide;
N-5-isoquinolinyl-3-[4-(trifluoromethyl)phenyl]-3-butenamide;
(2Z)-N-5-isoquinolinyl-3-[4-(trifluoromethyl)phenyl]-2-butenamide;
(2E)-3-[3-fluoro-4-(trifluoromethyl)phenyl]-N-5-isoquinolinyl-2-butenamide;
3-[3-fluoro-4-(trifluoromethyl)phenyl]-N-5-isoquinolinyl-3-butenamide;
(2E)-N-5-isoquinolinyl-3-[4-(1-piperidinyl)phenyl]-2-butenamide;
N-5-isoquinolinyl-3-[4-(trifluoromethyl)phenyl]acrylamide;
N-5-isoquinolinyl-3-[3-(trifluoromethyl)phenyl]acrylamide;
3-(4-isopropylphenyl)-N-5-isoquinolinylacrylamide;
3-(3,4-dichlorophenyl)-N-5-isoquinolinylacrylamide;
3-(1,1'-biphenyl-4-yl)-N-5-isoquinolinylacrylamide;
3-(3-bromo-4-fluorophenyl)-N-5-isoquinolinylacrylamide;
3-(4-tert-butylphenyl)-N-5-isoquinolinylacrylamide; and
3-[3-fluoro-4-(trifluoromethyl)phenyl]-N-5-isoquinolinylacrylamide.

45. The compound according to claim 2 wherein $X_5$ is C;
$Z_1$ is O;
$Z_2$ is NH;
L is alkylene; and
$R_9$ is heterocycle.

46. The compound according to claim 2 wherein $X_5$ is C;
$R_1$, $R_6$ and $R_7$ are each hydrogen;
$R_2$ and $R_4$ are independently selected from the group consisting of hydrogen, alkyl, halogen, hydroxy, and —$NZ_AZ_B$;
$R_5$ is selected from the group consisting of hydrogen and halogen;
$R_{8a}$ is hydrogen;
$R_{8b}$ is hydrogen;
$Z_1$ is O;
$Z_2$ is NH;
L is alkylene;

R$_9$ is heterocycle wherein said heterocycle is selected from the group consisting of imidazolyl, pyridinyl, pyrrolidinyl, and thienyl, wherein the heterocycle is substituted with 0, 1 or 2 alternative substituents independently selected from the group consisting of alkoxy, alkyl, alkylsulfonyl, 1-azepanyl, 1-azocanyl, cyano, haloalkoxy, haloalkyl, haloalkylthio, halogen, oxo, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —NZ$_C$Z$_D$; and Z$_A$, Z$_B$, Z$_C$ and Z$_D$ are independently selected from the group consisting of hydrogen and alkyl.

47. The compound according to claim 46 selected from the group consisting of 2-(5-isoquinolinyl)-N-[2-(2-thienyl)ethyl]acetamide;

N-[3-(1H-imidazol-1-yl)propyl]-2-(5-isoquinolinyl) acetamide;

2-(5-isoquinolinyl)-N-[3-(2-oxo-1-pyrrolidinyl)propyl] acetamide; and 2-(5-isoquinolinyl)-N-[2-(3-pyridinyl)ethyl]acetamide.

48. The compound according to claim 2 wherein

X$_5$ is C;

Z$_1$ is O;

Z$_2$ is NH;

L is —(CH$_2$)$_m$O(CH$_2$)$_n$— wherein the left end is attached to Z$_2$ and the right end is attached to R$_9$; and R$_9$ is hydrogen.

49. The compound according to claim 2 wherein

X$_5$ is C;

R$_1$, R$_6$ and R$_7$ are each hydrogen;

R$_2$ and R$_4$ are independently selected from the group consisting of hydrogen, alkyl, halogen, hydroxy, and —NZ$_A$Z$_B$;

R$_5$ is selected from the group consisting of hydrogen and halogen;

R$_{8a}$ is hydrogen;

R$_{8b}$ is hydrogen;

Z$_1$ is O;

Z$_2$ is NH;

L is —(CH$_2$)$_m$O(CH$_2$)$_n$— wherein the left end is attached to Z$_2$ and the right end is attached to R$_9$;

m is 1–4;

n is 0–4;

R$_9$ is hydrogen; and

Z$_A$ and Z$_B$ are independently selected from the group consisting of hydrogen and alkyl.

50. The compound according to claim 49 that is N-(3-butoxypropyl)-2-(5-isoquinolinyl)acetamide.

51. The compound according to claim 2 wherein

X$_5$ is C;

Z$_1$ is O;

Z$_2$ is NH;

L is alkylene; and

R$_9$ is aryl.

52. The compound according to claim 2 wherein

X$_5$ is C;

R$_1$, R$_6$, R$_7$, R$_{8a}$ and R$_{8b}$ are each hydrogen;

R$_2$ and R$_4$ are independently selected from the group consisting of hydrogen, alkyl, halogen, hydroxy, and —NZ$_A$Z$_B$;

R$_5$ is selected from the group consisting of hydrogen and halogen;

Z$_1$ is O;

Z$_2$ is NH;

L is alkylene;

R$_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —NZ$_C$Z$_D$; and Z$_A$, Z$_B$, Z$_C$ and Z$_D$ are independently selected from the group consisting of hydrogen and alkyl.

53. The compound according to claim 52 selected from the group consisting of 2-isoquinolin-5-yl-N-[4-(trifluoromethyl)benzyl] acetamide;

N-(4-bromobenzyl)-2-(3-methyl-5-isoquinolinyl) acetamide;

N-(4-bromobenzyl)-2-(5-isoquinolinyl)acetamide;

N-[1-(4-bromophenyl)ethyl]-2-(5-isoquinolinyl) acetamide;

N-[1-(4-bromophenyl)ethyl]-2-(3-methyl-5-isoquinolinyl)acetamide;

2-(5-isoquinolinyl)-N-[4-(trifluoromethoxy)benzyl] acetamide;

N-(4-tert-butylbenzyl)-2-(5-isoquinolinyl)acetamide;

N-[3-fluoro-4-(trifluoromethyl)benzyl]-2-(5-isoquinolinyl)acetamide;

N-{1-[3-fluoro-4-(trifluoromethyl)phenyl]ethyl}-2-(5-isoquinolinyl)acetamide;

N-{1-[3-fluoro-4-(trifluoromethyl)phenyl]propyl}-2-(5-isoquinolinyl)acetamide;

2-(3-methyl-5-isoquinolinyl)-N-[4-(trifluoromethyl) benzyl]acetamide;

N-[3-fluoro-4-(trifluoromethyl)benzyl]-2-(3-methyl-5-isoquinolinyl)acetamide;

2-(5-isoquinolinyl)-N-{2-[3-(trifluoromethyl)phenyl] ethyl}acetamide;

N-(3,3-diphenylpropyl)-2-(5-isoquinolinyl)acetamide;

2-(5-isoquinolinyl)-N-(3-phenylpropyl)acetamide;

N-(2,2-diphenylethyl)-2-(5-isoquinolinyl)acetamide;

N-benzyl-2-(5-isoquinolinyl)acetamide;

2-(5-isoquinolinyl)-N-{4-[(trifluoromethyl)thio] benzyl}acetamide;

2-(5-isoquinolinyl)-N-(2-phenylethyl)acetamide;

N-[3-bromo-4-(trifluoromethyl)benzyl]-2-(5-isoquinolinyl)acetamide;

N-(4-bromo-3-methylbenzyl)-2-(5-isoquinolinyl) acetamide;

N-[2,4-bis(trifluoromethyl)benzyl]-2-(5-isoquinolinyl) acetamide;

N-[2-chloro-4-(trifluoromethyl)benzyl]-2-(5-isoquinolinyl)acetamide;

N-[2,3-difluoro-4-(trifluoromethyl)benzyl]-2-(5-isoquinolinyl)acetamide; and

N-[4-(1-azepanyl)-3-fluorobenzyl]-2-(5-isoquinolinyl) acetamide.

54. The compound according to claim 2 wherein $X_5$ is C;

$R_1$, $R_6$, and $R_7$ are each hydrogen;

$R_2$ and $R_4$ are independently selected from the group consisting of hydrogen, alkyl, halogen, hydroxy, and —$NZ_AZ_B$;

$R_5$ is selected from the group consisting of hydrogen and halogen;

$R_{8a}$ is selected from the group consisting of hydrogen and alkyl;

$R_{8b}$ is alkyl;

$Z_1$ is O;

$Z_2$ is NH;

L is alkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

55. The compound according to claim 54 selected from the group consisting of

N-[3-fluoro-4-(trifluoromethyl)benzyl]-2-(5-isoquinolinyl)propanamide;

2-(5-isoquinolinyl)-N-[4-(trifluoromethyl)benzyl]propanamide;

2-(5-isoquinolinyl)-N-[3-(trifluoromethyl)benzyl]propanamide;

2-(5-isoquinolinyl)-N-{4-[(trifluoromethyl)thio]benzyl}propanamide;

N-(4-bromobenzyl)-2-(5-isoquinolinyl)propanamide;

N-(4-tert-butylbenzyl)-2-(5-isoquinolinyl)propanamide;

N-[3-fluoro-5-(trifluoromethyl)benzyl]-2-(5-isoquinolinyl)propanamide;

2-(5-isoquinolinyl)-N-[4-(trifluoromethoxy)benzyl]propanamide;

2-(5-isoquinolinyl)-N-[3-(trifluoromethoxy)benzyl]propanamide;

N-(2,4-dimethylbenzyl)-2-(5-isoquinolinyl)propanamide;

N-(2,5-dimethylbenzyl)-2-(5-isoquinolinyl)propanamide;

N-(2,3-dichlorobenzyl)-2-(5-isoquinolinyl)propanamide;

N-(2,4-dichlorobenzyl)-2-(5-isoqinolinyl)propanamide;

N-(2,5-dichlorobenzyl)-2-(5-isoquinolinyl)propanamide;

N-(3,4-dichlorobenzyl)-2-(5-isoquinolinyl)propanamide;

N-(3,5-dichlorobenzyl)-2-(5-isoquinolinyl)propanamide;

N-[4-(1-azepanyl)benzyl]-2-(5-isoquinolinyl)propanamide;

N-[4-(1-azepanyl)-3-fluorobenzyl]-2-(5-isoquinolinyl)propanamide;

N-[3-fluoro-4-(trifluoromethyl)benzyl]-2-(5-isoquinolinyl)butanamide;

2-(5-isoquinolinyl)-N-[4-(trifluoromethyl)benzyl]butanamide;

N-(4-bromobenzyl)-2-(5-isoquinolinyl)butanamide;

2-(5-isoquinolinyl)-N-{4-[(trifluoromethyl)thio]benzyl}butanamide;

N-[4-(1-azepanyl)-3-fluorobenzyl]-2-(5-isoquinolinyl)butanamide; and 2-(5-isoquinolinyl)-2-methyl-N-{4-[(trifluoromethyl)thio]benzyl}propanamide.

56. The compound according to claim 2 wherein $X_5$ is C;

$R_1$, $R_6$, and $R_7$ and are each hydrogen;

$R_2$ and $R_4$ are independently selected from the group consisting of hydrogen, alkyl, halogen, hydroxy, and —$NZ_AZ_B$;

$R_5$ is selected from the group consisting of hydrogen and halogen;

$R_{8a}$ is hydrogen;

$R_{8b}$ is selected from the group consisting of alkoxy, alkoxycarbonylalkyl, alkylcarbonyloxy, alkylsulfonyl, halogen, and hydroxy;

$Z_1$ is O;

$Z_2$ is NH;

L is alkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_A$, $Z_B$, $Z_C$ and $Z_D$ are independently selected from the group consisting of hydrogen and alkyl.

57. The compound according to claim 56 selected from the group consisting of

N-(4-tert-butylbenzyl)-2-hydroxy-2-(5-isoquinolinyl)acetamide;

N-(4-tert-butyl-3-fluorobenzyl)-2-hydroxy-2-(5-isoquinolinyl)acetamide;

tert-butyl 4-[(4-tert-butylbenzyl)amino]-3-(5-isoquinolinyl)-4-oxobutanoate;

2-[(4-tert-butylbenzyl)amino]-1-(5-isoquinolinyl)-2-oxoethyl acetate;

2-[(4-tert-butylbenzyl)amino]-1-(5-isoquinolinyl)-2-oxoethyl methanesulfonate;

N-(4-tert-butylbenzyl)-2-(5-isoquinolinyl)-2-methoxyacetamide; and

N-(4-tert-butylbenzyl)-2-chloro-2-(5-isoquinolinyl)acetamide.

58. The compound according to claim 2 wherein $X_5$ is C;

$R_1$, $R_6$, $R_7$, and $R_7$ are each hydrogen;

$R_2$ and $R_4$ are independently selected from the group consisting of hydrogen, alkyl, halogen, hydroxy, and —$NZ_AZ_B$;

$R_5$ is selected from the group consisting of hydrogen and halogen;

$R_{8a}$ is selected from the group consisting of hydrogen and alkyl;

$R_{8b}$ is selected from the group consisting of hydrogen, alkoxycarbonylalkyl, alkyl, and hydroxy;

$Z_1$ is O;

$Z_2$ is O;

L is alkylene;

$R_9$ is hydrogen; and $Z_A$ and $Z_B$ are independently selected from the group consisting of hydrogen and alkyl.

59. The compound according to claim 58 selected from the group consisting of ethyl 5-isoquinolinylacetate;

ethyl 2-(5-isoquinolinyl)propanoate;

ethyl 2-(5-isoquinolinyl)butanoate;

ethyl 2-(5-isoquinolinyl)-2-methylpropanoate;

ethyl hydroxy(5-isoquinolinyl)acetate; and 4-tert-butyl 1-ethyl 2-(5-isoquinolinyl)succinate.

60. The compound according to claim 1 wherein

- - - is a single bond;

$X_1$ is $CR_1$;

$X_2$ is N;

$X_3$ is $CR_3$; and $X_4$ is $CR_4$.

61. The compound according to claim 60 wherein $X_5$ is N;

$R_{8b}$ is absent;

$Z_1$ is O;

$Z_2$ is NH;

L is alkylene; and $R_9$ is aryl.

62. The compound according to claim 60, wherein $X_5$ is N;

$R_1$, $R_3$, $R_4$, $R_5$, $R_6$ and $R_7$ are each hydrogen;

$R_{8b}$ is absent;

$Z_1$ is O;

$Z_2$ is NH;

L is alkylene;

$R_9$ is aryl wherein said aryl is phenyl substituted with 0, 1, 2, or 3 alternative substituents independently selected from the group consisting of alkoxy, alkyl, alkylsulfonyl, 1-azepanyl, 1-azocanyl, cyano, haloalkoxy, haloalkyl, haloalkylthio, halogen, methylenedioxy, 4-morpholinyl, 2,6,-dimethyl-4-morpholinyl, phenyl, 1-piperidinyl, 4-methyl-1-piperidinyl, pyridinyl, 1-pyrrolidinyl, 4-thiomorpholinyl, and —$NZ_CZ_D$; and $Z_C$ and $Z_D$ are independently selected from the group consisting of hydrogen and alkyl.

63. The compound according to claim 62 selected from the group consisting of

N-isoquinolin-8-yl-N'-[4-(trifluoromethyl)benzyl]urea; and

N-(4-bromobenzyl)-N'-isoquinolin-8-ylurea.

64. A pharmaceutical composition comprising a therapeutically effective amount of a compound of formula (I) according to claim 1, or a pharmaceutically acceptable salt thereof, in combination with a pharmaceutically acceptable carrier.

65. A method of treating a disorder wherein the disorder is ameliorated by inhibiting vanilloid receptor subtype 1 (VR1) receptor, and wherein the disorder is selected from the group comprising pain, bladder overactivity, urinary incontinence and inflammatory thermal hyperalgesia in a host mammal in need of such treatment comprising administering a therapeutically effective amount of a compound of formula (I) according to claim 1, or a pharmaceutically acceptable salt thereof.

66. A method of treating bladder overactivity in a host mammal in need of such treatment comprising administering a therapeutically effective amount of a compound of formula (I) according to claim 1, or a pharmaceutically acceptable salt thereof.

67. A method of treating urinary incontinence in a host mammal in need of such treatment comprising administering a therapeutically effective amount of a compound of formula (I) according to claim 1, or a pharmaceutically acceptable salt thereof.

68. A method of treating pain in a host mammal in need of such treatment comprising administering a therapeutically effective amount of a compound of formula (I) according to claim 1, or a pharmaceutically acceptable salt thereof.

69. A method of treating inflammatory thermal hyperalgesia in a host mammal in need of such treatment comprising administering a therapeutically effective amount of a compound of formula (I) according to claim 1, or a pharmaceutically acceptable salt thereof.

* * * * *